US007319009B2

(12) United States Patent
Klein et al.

(10) Patent No.: US 7,319,009 B2
(45) Date of Patent: Jan. 15, 2008

(54) METHODS AND COMPOSITIONS FOR IDENTIFYING RECEPTOR EFFECTORS

(75) Inventors: Christine A. Klein, Ossining, NY (US); Andrew J. Murphy, Croton-on-Hudson, NY (US); Jeremy Paul, Nyack, NY (US)

(73) Assignee: Cadus Technologies, Inc., New York, NY (US)

( * ) Notice: Subject to any disclaimer, the term of this patent is extended or adjusted under 35 U.S.C. 154(b) by 358 days.

(21) Appl. No.: 10/277,607

(22) Filed: Oct. 22, 2002

(65) Prior Publication Data

US 2003/0166143 A1 Sep. 4, 2003

Related U.S. Application Data

(63) Continuation of application No. 09/201,396, filed on Nov. 30, 1998, now abandoned, and a continuation-in-part of application No. PCT/US98/21168, filed on Oct. 7, 1998.

(60) Provisional application No. 60/109,902, filed on Nov. 25, 1998.

(51) Int. Cl.
  *C07K 14/705* (2006.01)
  *G01N 33/554* (2006.01)
  *G01N 33/566* (2006.01)

(52) U.S. Cl. ............... 435/7.1; 435/7.21; 435/69.1; 435/254.2; 436/501

(58) Field of Classification Search ............ 435/7.21, 435/69.1, 254.2
See application file for complete search history.

(56) References Cited

U.S. PATENT DOCUMENTS

| | | | |
|---|---|---|---|
| 4,948,874 A | 8/1990 | Kronvall et al. | 530/350 |
| 5,096,815 A | 3/1992 | Ladner et al. | 435/69.1 |
| 5,283,173 A | 2/1994 | Fields et al. | 435/6 |
| 5,401,629 A | 3/1995 | Harpold et al. | 435/6 |
| 5,436,128 A | 7/1995 | Harpold et al. | 435/6 |
| 5,468,614 A | 11/1995 | Fields et al. | 435/6 |
| 5,580,736 A | 12/1996 | Brent et al. | 435/6 |
| 5,789,184 A | 8/1998 | Fowlkes et al. | 435/7.31 |

FOREIGN PATENT DOCUMENTS

| | | |
|---|---|---|
| EP | 0 568 925 | 11/1993 |
| WO | WO 88/10308 | 12/1988 |
| WO | WO 91/12273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |

OTHER PUBLICATIONS

Alison, M.R. et al. "Growth factors and growth factor receptors" *British Journal of Hospital Medicine* 49(11):774-788 (1993).
Altieri, D.C. "Proteases and protease receptors in modulation of leukocyte effector functions" *Journal of Leukocyte Biology* 58:120-127 (1995).
Bao, L. et al. "Mapping of Genes for the Human C5a Receptor (C5AR), Human FMLP Receptor (FPR), and Two FMLP Receptro Homologue Orphan Receptors (FPRH1, FPRH2) to Chromosome 19" *Genomics* 13:437-440 (1992).
Barak, L.S. et al. "A beta-arrestin/green fluorescent protein biosensor for detecting G protein-coupled receptor activation," *J. Biol. Chem.* 272(44):27497-27500 (Oct. 31, 1997).
Belka, C. et al. "The role of tyrosine kinases and their substrates in signal transmission of hematopoietic growth factors: a short review" *Leukemia* 9:754-761 (1995).
Birnbaumer, L. "Transduction of receptor signal into modulation of effector activity by G proteins: the first 20 years or so . . . " *FASEB Journal* 4:3178-3188 (1990).
Brugarolas, J. et al. "Radiation-induced cell cycle arrest compromised by p21 deficiency" *Nature* 377:552-557 (1995).
Chambers, D.A. et al. "Neuroimmune Modulation: Signal Transduction and Catecholamines" *Neurochem. Int.* 22(2):95-110 (1993).
Chien, Cheng-Ting et al. "The Two-Hybrid System: A Method To Identify and Clone Genes For Proteins That Interact With A Protein of Interest" *Proc. Natl. Acad. Sci. USA*, 88:9578-9582 (1991).
Cwirla, S. et al. "Peptides on Phage: A Vast Library of Peptides for Identifying Ligands" *Proc. Natl. Acad. Sci. USA* 87: 6378-6382 (1990).
Devlin, J. et al. "Random Peptide Libraries: A Source of Specific Protein Binding Molecules" *Science* 249:404-406 (1990).
Dubois, P.M. "Role of the transmembrane and cytoplasmic domains of surface IgM in endocytosis and signal transduction" *Eur. J. Immunol.* 22:851-857 (1992).
Durstin, M. et al. "Differential Expression of Members of the N-Formylpeptide Receptor Gene Cluster in Human Phagocytes" *Biochem. Biophys. Res. Comm.* 201:174-179 (1994).
Erickson, D. "Intercepted Messages: New biotechnology drugs target intracellular communication" *Scientific American* (November):122-123 (1992).

(Continued)

*Primary Examiner*—John Ulm
(74) *Attorney, Agent, or Firm*—Edwards Angell Palmer & Dodge LLP; Peter C. Lauro, Esq.; Melissa Hunter Endsor

(57) ABSTRACT

The present invention makes available rapid, effective assays for screening and identifying pharmaceutically effective compounds that specifically interact with and modulate the activity of a cellular receptor or ion channel. The subject assays enable rapid screening of large numbers of polypeptides in a library to identify those polypeptides which induce or antagonize receptor bioactivity. The subject assays are particularly amenable for identifying agonists and antagonists for orphan receptors. In particular the present invention makes available novel ligand agonists of human formyl peptide receptor like-1 (FPRL-1) receptors. These novel ligand agonists are used in the assays of the invention to identify modulators of FPRL-1 receptor.

38 Claims, 8 Drawing Sheets

OTHER PUBLICATIONS

Fields, Stanley et al. "A Novel Genetic System To Detect Protein-Protein Interactions" *Nature* 340:245-246, (1989).

Fiore, S. et al. "Identification of a Human cDNA Encoding a Functional High Affinity Lipoxin $A_4$ Receptor" *J. Exp. Med.* 180:253-260 (1994).

Funaro, A. et al. "Human CD38 is associated to distinct molecules which mediate transmembrane signaling in different lineages" *Eur. J. Immunol.* 23:2407-2411 (1993).

Gordon, J. "B-cell signalling *via* the C-type lectins CD23 and CD72" *Immunology* 15(9):411-417 (1994).

Gyuris, J. et al. "Cdi1, A Human G1 and S Phase Protein Phosphatase That Assocites With CdK2", *Cell* 75:791-803 (1993).

Hall, M. et al. "Evidence for different modes of action of cyclin-dependent kinase inhibitors: p15 and p16 bind to kinases, p21 and p27 bind to cyclins" *Oncogene* 11:1581-1588 (1995).

Hughes, David et al. "complementation of byr1 in Fission Yeast By Mammalian MAP Kinase Kinase Requires CoExpression of Raf Kinase" *Nature* 364:349-352, (1993).

Imamoto, A. et al. "Genetics of signal transduction: tales from the mouse" *Curr. Opion. Gen. & Dev.* 4:40-46 (1994).

Jakobs, K.H. et al. "Dual regulation of adenylate cyclase. A signal transduction mechanism of membrane receptors" *Basic Res. Cardiol.* 81:1-9 (1986).

Kang, Y-S. et al. "Effects of expression of mammalian $G\alpha$ and hybrid mammalian-yeast $G\alpha$ proteins on the yeast pheromone response signal transduction pathway." *Molecular and Cellular Biology* 10(6):2582-2590 (1990).

King, K. et al. "Control of Yeast Mating Signal Transduction by a Mammalian $\beta_2$-Adrenergic Receptor and $G_s$ $\alpha$ Subunit" *Science* 250:121-123 (1990).

Klein, C. et al. "Identification of surrogate agonists for the human FPRL-1 receptor by autocrine selection in yeast," *Nat Biotechnol.* 16(13):1334-1337 (Dec. 1998).

Koff, Andrew et al. "Human Cyclin E, A New Cyclin That Interacts With Two Members of the CDC2 Gene Family", *Cell* 66:1217-1228 (1991).

Kosugi, S. et al. "Characterization of heterogeneous mutations causing constitutive activation of the luteinizing hormone receptor in familial male precocious puberty" *Human Molecular Genetics* 4(2):183-188 (1995).

Lew, D.J. et al. "Isolation of Three Novel Human Cyclins by Rescue of G1 Cyclin (Cln) Function in Yeast" *Cell.* 66:1197-1206 (1991).

Linder, M.E. and A.G. Gilman "G Proteins" *Scientific American July*:56-65 (1992).

Manfredi, J. et al. "Autocrine stimulation of yeast through human G-coupled receptors," *J. Cell. Biochem.*, 18B:224 (1994).

Manfredi, J.P. et al. "Yeast $\alpha$ Mating Factor Structure-Activity Relationship Derived from Genetically Selected Peptide Agonists and Antagonists of Ste2p" 16:4700-4709 (1996).

Marengere, L.E.M. and T. Pawson "Structure and function of SH2 domains" *J. Cell Science* Suppl. 18:97-104 (1994).

Milburn, M.V. et al. "Molecular Switch for Signal Transduction: Structural Differences Between Active and Inactive Forms of Protooncogenic *ras* Proteins" *Science* 247:939-945 (1990).

Murphy, A.J.M. et al. "Autocrine Stimulation of Yeast Through Human G-Coupled Receptors," *J. Cell Biochem.* 18B:224 (1994).

Murphy, P.M. et al. "A Structural Homologue of the *N*-Formyl Peptide Receptor," *J. Biol. Chem.* 267:7637-7643 (1992).

Murphy, P.M. et al. "A structural homologue of the N-formyl peptide receptor. Characterization and chromosome mapping of a peptide chemoattractant receptor family," *J Biol Chem.* 267(11):7637-7643 (Apr. 15, 1992).

Noelle, R.J. et al. "CD40 and it ligand, an essential ligand-receptor pair for thymus-dependent B-cell activation" *Immunology Today* 13(11):431-433 (1992).

Nye, J.S. and R. Kopan "Vertebrate ligands for Notch" *Current Biology* 5(9):966-969 (1995).

Pausch, M.H. et al. "G-protein-coupled receptors in *Saccharomyces cerevisiae*: high-throughput screening assays for drug discovery," *Trends Biotechnol.* 15(12):487-494 (Dec. 1997).

Ranade, K. et al. "Mutations associated with familial melanoma impair $p16^{INK4}$ funtion" *Nature Genetics* 10:114-116 (1995).

Raymond, M. et al. "Functional Complementation of Yeast ste6 by a Mammalian Multidrug Resistance mdr Gene" *Science* 256:232-234 (1992).

Reed, R.R. "G Protein Diversity and the Regulation of Signaling Pathways" *The New Biologist* 2(11):957-960 (1990).

Scott, J.K. and G.P. Smith "Searching for Peptide Ligands with an Epitope Library" *Science* 249:386-390 (1990).

Stadel, J.M. et al. "Orphan G protein-coupled receptors: a neglected opportunity for pioneer drug discovery," *Trends Pharmacol Sci.* 18(11):430-437 (Nov. 1997).

Suzuki, T. et al. "HTLV-1 Tax protein interacts with cyclin-dependent kinase inhibitor $p16^{INK4A}$ and counteracts its inhibitory activity towards CDK4" *EMBO J.* 15(7):1607-1614 (1996).

Whiteway, M. et al. "Dominant negative selection of heterologous genes: Isolation of *Candida albicans* genes that interfere with *Saccharomyces cerevisiae* mating factor-induced cell cycle arrest" *Proc. Natl. Acad. Sci. USA* 89:9410-9414 (1992).

Wolowiec, D. et al. "Expression of cell cycle regulatory proteins in chronic lymphocytic leukemias. Comparison with non-Hodgkin's lymphomas and non-neoplastic lymphoid tissue" *Leukemia* 9:1382-1388 (1995).

Xiong, Y. et al. "Alteration of Cell Cycle Kinase Complexes in Human Papillomavirus E6- and E7- Expressing Fibroblasts Precedes Neoplastic Transformation" *J. Virol.* 70(2):999-1008, (Feb. 1996).

Xiong, Y. et al. "Human D-Type Cyclin" *Cell* 65:691-699 (1991).

Ye, R.E. et al. "Isolation of a cDNA That Encodes a Novel Granulocyte N-Formyl Peptide Receptor" *Biochem. and Biophys. Res. Comm.* 184:582-589 (1992).

Zervos, Antonis et al. "Mxi1, A Protein That Specifically Interacts With Max to Bind Myc-Max Recognition Sites" *Cell* 72:223-232 (1993).

Lodish, et al., *Molecular Cell Biology*, Chapter 20.1(W. H. Freeman and Company, 2000).

Lodish, et al.. *Molecular Cell Biology*, Chapter 20.3 (W. H. Freeman and Company, 2000).

Strachan, et al., *Human Molecular Genetics*, Chapter 16 (BIOS Scientific Publishers, Ltd, 1999).

Cooper, *The Cell A Molecular Approach*, Chapter 13, 2nd edition (Sinauer, 2000).

METHODS AND COMPOSITIONS FOR IDENTIFYING RECEPTOR EFFECTORS

CROSS REFERENCE TO RELATED APPLICATIONS

This application is a continuation of U.S. application Ser. No. 09/201,396, filed Nov. 30, 1998, now abandoned, which claims priority to U.S. provisional application Ser. No. 60/109,902, filed Nov. 25, 1998, now abandoned. This application is also a Continuation in Part of PCT/US98/21168 filed Oct. 7, 1998, which claims priority to U.S. application Ser. No. 08/946,298, filed Oct. 7, 1997, now abandoned, which is a Continuation in Part of U.S. application Ser. No. 08/689,172, filed Aug. 6, 1996, now abandoned, which is a Continuation in Part of U.S. application Ser. No. 08/582,333, filed Jan. 17, 1996, now issued as U.S. Pat. No. 6,255,059.

BACKGROUND OF THE INVENTION

A common technique for cloning receptors is to use nucleic acid hybridization technology to identify receptors which are homologous to other, known receptors. For instance, originally the cloning of seven transmembrane domain G protein-coupled receptors (GPCR) depended on the isolation and sequencing of the corresponding protein or the use of expression cloning techniques. However, when sequences for these receptors became available, it was apparent that there were significant sequence homologies between these receptors. Because this technology does not require that the ligand of the receptor be identified, the cloning of a large number of "orphan receptors", which have no known ligand and the biological function of which is often obscure, has resulted. Receptors of all types comprise this large family.

Known orphan receptors include the nuclear receptors COUP-TF1/EAR3, COUP-TF2/ARP1, EAR-1, EAR-2, TR-2, PPAR1, HNF-4, ERR-1, ERR-2, NGFIB/Nur77, ELP/SF-1 and MPL (Parker et al. supra, and Power et al. (1992) TIBS 13:318-323). A large number of orphan receptors has been identified in the EPH family (Hirai et al. (1987) Science 238:1717-1720). HER3 and HER4 are orphan receptors in the epidermal growth factor receptor family (Plowman et al. (1993) Proc. Natl. Acad. Sci. USA 90:1746-1750). ILA is a newly identified member of the human nerve growth factor/tumor necrosis factor receptor family (Schwarz et al. (1993) Gene 134:295-298). IRRR is an orphan insulin receptor-related receptor which is a transmembrane tyrosine kinase (Shier et al. (1989) J. Biol Chem 264:14606-14608). Several orphan tyrosine kinase receptors have been found in Drosophila (Perrimon (1994) Curr. Opin. Cell Biol. 6:260-266). The identification of ligands for orphan receptors is important to drug discovery.

One large subgroup of orphan receptors, as alluded to above, is found in the G protein coupled receptor (GPCR) family. Approximately 100 such receptors have been identified as mediators of transmembrane signaling from external stimuli (vision, taste and smell), endocrine function (pituitary and adrenal), exocrine function (pancreas), heart rate, lipolysis, and carbohydrate metabolism. Structural similarities suggest that the G protein-coupled receptors of animals can be subclassified into three distinct groups: (i) the largest class including monoamine, cytokine, lipid, neuropeptide etc. receptors; (ii) the class represented by calcitonin, secretin and VIP receptors but also containing orphan receptors like emr-1 (Baud V. et al., 1995 Genomics 26: 334-44) and methuselah (Lin Y. J. et al., 1998 Science 282: 943-6); and (iii) the metabotropic glutamate and calcium-sensing receptors.

Formyl peptide receptor like-1 receptor (FPRL-1) was identified as an orphan GPCR through low stringency hybridization of a human formyl peptide receptor (FPR1)-specific cDNA probe to a cDHA library derived from HL-60 cells (Murphy, et al. (1992) J. Biol. Chem. 267:7637-7643; Ye, R. D., et al. (1992) Biochem. Biophys. Res. Comm. 184:582-589). FPRL-1-specific RNA is expressed in neutrophils and monocytes (Durstin, et al. (1994) Biochem. Biophys. Res. Comm. 201:174-179). The receptor exhibits 69% amino acid identity to FPR1 and maps to the locus on human chromosome 19 that contains the genes for the C5a receptor, FPR1 and for a second FPR1-related orphan, FPRL-2 (Bao, et al. (1992) Genomics 13:437-440). FPR1 is also expressed in neutrophils and monocytes and is stimulated by N-formylated peptides of bacterial origin. Specific binding of the ligand fMLP to FPR1 on neutrophils stimulates calcium mobilization and results in a variety of cellular changes including chemotaxis, degranulation and the respiratory burst. FPRL-1 has been characterized as a low affinity receptor for fMLP (Ye, et al. (1992) Biochem. Biophys. Res. Comm. 184:582-589) and a high affinity receptor for lipoxin $A_4$ (Fiore, et al. (1994) J. Exp. Med. 180:253-260). However, treatment of cells expressing FPRL-1 with lipoxin A4 results in a limited biological response (Fiore, et al. (1994) J. Exp. Med. 180:253-260), so the role of this receptor in the normal functioning of neutrophils and monocytes remains unresolved.

Previous work describes the expression of recombinant mammalian G protein-coupled receptors as a means of studying receptor function in order to identify agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidyinositol hydrolysis and intracellular $Ca^{2+}$ mobilization in Chinese hamster ovary cells upon agonist stimulation (Lolait et al. (1995) Proc Natl. Acad. Sci. USA 92:6783-6787). These types of ectopic expression studies have enabled researchers to study receptor signaling mechanisms and to perform mutagenesis studies which have been useful in identifying portions of receptors that are critical for ligand binding or signal transduction.

Experiments have also been undertaken to express functional G protein coupled receptors in yeast cells. For example, U.S. Pat. No. 5,482,835 to King et al. describes a transformed yeast cell which is incapable of producing a yeast G protein α subunit, but which has been engineered to produce both a mammalian G protein α-subunit and a mammalian receptor which is "coupled to" (i.e., interacts with) the aforementioned mammalian G protein α-subunit. Specifically, U.S. Pat. No. 5,482,835 discloses expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast α-factor receptor). King et al. found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 also describes co-expression of a rat G protein α-subunit in the same cells, yeast strain 8C, which lacks the cognate yeast protein. Ligand binding resulted in G protein-mediated signal transduction. U.S. Pat. No. 5,482,835 further teaches that these cells may be used in screening compounds for the ability to affect the rate of dissociation of Gα from Gβγ in a cell. For this purpose, the cell further contains a pheromone-responsive promoter (e.g., BAR1 or FUS1), linked to an indicator gene (e.g. HIS3 or LacZ). The cells are placed in multi-titer plates, and different compounds are placed in each well. The colonies are then scored for expression of the indicator gene.

Genome sequencing efforts and homology-based cloning have revealed a large number of human genes encoding G protein-coupled receptors (GPCRs) of unknown function. Elucidation of the function of these orphan receptors has been difficult, relying primarily on homology to known receptors, circumstantial inference from expression patterns or identification of the natural ligand for the receptor. This latter process, although successful in identifying anadamide as a potential endogenous ligand of the cannabinoid receptor (Devane, et al. (1992) *Science* 258:1946-1949) and the pituitary neuropeptide nociceptin as an agonist of the opioid-like GPCR, ORL 1 (Meunier, et al. (1995) *Nature* 377:532-535), is inherently inefficient, involving methodical searches through extracts of likely tissue sources.

SUMMARY OF THE INVENTION

The present invention relates to a rapid, reliable and effective assay for screening and identifying pharmaceutically effective compounds that specifically interact with and modulate the activity of a cellular receptor or ion channel. The subject assay enables rapid screening of large numbers of compounds (e.g., peptidic or non-peptidic) to identify those compounds which agonize or antagonize receptor bioactivity.

In one aspect, the assay is characterized by the use of recombinant cells which include (i) a target FPRL-1 receptor protein whose signal transduction activity can be modulated by interaction with an extracellular signal, the transduction activity generating a detectable signal as a result of the interaction, (ii) a ligand agonist of the target FPRL-1 receptor protein which is expressed in the recombinant cell, and (iii) a test compound expressed by the recombinant cell that antagonizes or agonizes the interaction between the target FPRL-1 receptor protein and the ligand agonist.

In another aspect, the assay is characterized by the use of recombinant cells which include (i) a target FPRL-1 receptor protein whose signal transduction activity can be modulated by interaction with an extracellular signal, the transduction activity generating a detectable signal as a result of the interaction, and (ii) a ligand agonist of the target FPRL-1 receptor protein expressed in the recombinant cell. Test compounds that antagonize or agonize the interaction between the target FPRL-1 receptor protein and the ligand agonist can be identified by contacting the recombinant cells with a test compound, or a library of test compounds.

In another aspect, the assay is characterized by the use of recombinant cells which include (i) a target FPRL-1 receptor protein whose signal transduction activity can be modulated by interaction with an extracellular signal, the transduction activity generating a detectable signal as a result of the interaction, and (ii) a test compound expressed by the recombinant cell. The test compound so expressed is contacted with an exogenous ligand agonist of the target FPRL-1 receptor protein to identify a test compound that antagonizes or agonizes the interaction between the target FPRL-1 receptor protein and the ligand agonist.

In another aspect, the invention is characterized by the use of a mixture of recombinant cells, each cell of which expresses a target FPRL-1 receptor and a test compound. Collectively, the mixture of cells expresses a library of test compounds such that a member of the library antagonizes or agonizes interaction between the target FPRL-1 receptor and a ligand agonist of the invention.

In certain embodiments, the test compounds are members of a library of polypeptides including at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library. In other embodiments, the test compounds are members of a library of non-peptidic compounds including at least $10^3$ different non-peptidic compounds, though more preferably at least $10^5$, $10^6$, or $10^7$ different non-peptidic compounds.

The ability of particular constituents of the test library (peptide or non-peptidic compounds) to modulate the signal transduction activity of the target FPRL-1 receptor can be scored for by detecting up- or down-regulation of the detection signal. For example, second messenger generation via the receptor can be measured directly. Alternatively, the use of a reporter gene can provide a convenient readout. In any event, a statistically significant change in the detection signal can be used to facilitate isolation of those cells from the mixture which contain a nucleic acid encoding a test polypeptide which is an effector of the target FPRL-1 receptor.

By the methods of the invention, test polypeptides or non-peptidic compounds which induce receptor signaling can be identified. In one embodiment, the test compound is assayed for its ability to antagonize, e.g., inhibit or block the activity of the ligand agonists of the invention. Alternatively, the assay can score for test compounds which potentiate the induction response generated by interaction of the FPRL-1 receptor and the ligand agonists of the invention. As used herein, "agonist" refers to agents which either induce activation of receptor signaling pathways, e.g., such as by mimicking a ligand for the receptor, as well as agents which potentiate the sensitivity of the receptor to a ligand, e.g., lower the concentrations of ligand required to induce a particular level of receptor-dependent signaling.

In the method of the invention, the recombinant cells, e.g., yeast cells, are engineered to express a heterologous target FPRL-1 receptor protein. To express heterologous target FPRL-1 receptor protein, it may be desirable to inactivate one or more endogenous genes of the host cells. For example, certain preferred embodiments in which a heterologous receptor is provided utilize host cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein coupled receptor. Other complementations include, for example, expression of heterologous MAP kinases or erk kinases, MEKs or MKKs (MAP kinase kinases), MEKKs (MEK kinases), ras, raf, STATs, JAKs and the like.

In certain embodiments, it may be desirable for the polypeptides in the library to express a signal sequence to ensure that they are processed in the appropriate secretory pathway and thus are available to interact with the FPRL-1 receptor on the cell surface. Similarly, it may be desirable for the ligand agonists expressed by the host cells to also express a signal sequence.

With respect to a detection signal generated by signal transduction, certain embodiments of the invention comprises measuring the production of second messengers to determine changes in ligand engagement by the receptor. In other embodiments, changes in GTP hydrolysis, calcium mobilization, or phospholipid hydrolysis can be measured. In still other embodiments, the detectable signal can be a growth signal, an optical signal or intracellular calcium mobilization.

In still other embodiments, the host cells harbor a reporter construct containing a reporter gene in operative linkage with one or more transcriptional regulatory elements responsive to the signal transduction activity of the receptor protein. Exemplary reporter genes include enzymes, such as luciferase, phosphatase, or β-galactosidase which can produce a spectrometrically active label, e.g., changes in color, fluorescence or luminescence, or a gene product which alters a cellular phenotype, e.g., cell growth, drug resistance or auxotrophy. In preferred embodiments, the reporter gene encodes a gene product selected from the group consisting of chloramphenicol acetyl transferase, beta-galactosidase and secreted alkaline phosphatase; the reporter gene encodes a gene product which confers a growth signal; or the reporter gene encodes a gene product for growth in media containing aminotriazole or canavanine.

In other embodiments, associated with the FPRL-1 receptor and/or the ligand agonist is an indicator molecule/construct which provides a detectable signal in response to binding of the ligand agonist to the receptor.

The recombinant cells of the present invention can be derived from any prokaryotic or eukaryotic organism. In preferred embodiments the cells are mammalian cells. In more preferred embodiments the cells are yeast cells, with cells from the genera *Saccharomyces* or *Schizosaccharomyces* being more preferred. However, cells from amphibia (such as xenopus), avian or insect sources are also contemplated. The host cells can be derived from primary cells, or from transformed and/or immortalized cell lines.

Accordingly, in one aspect, the invention features a ligand agonist of formyl peptide receptor like-1 (FPRL-1) receptor comprising a polypeptide or analog thereof wherein the ligand agonist binds to and activates the FPRL-1 receptor. Preferably, the polypeptide comprises from 3 to 80 amino acid residues, more preferably from 3 to 40 amino acid residues, more preferably from 3 to 20 amino acid residues, and still more preferably from 3 to 13 amino acid residues. In general, the $EC_{50}$ values for the ligand agonists range from about $2 \times 10^{-9}$ M to about $20 \times 10^{-6}$ M. Preferably, the ligand agonist has an $EC_{50}$ of $2 \times 10^{-5}$ M or less. In a preferred embodiment, the ligand agonist has an $EC_{50}$ of $3 \times 10^{-6}$ M. In one embodiment, the $EC_{50}$ of the ligand agonist is determined by a calcium mobilization assay.

In another aspect the invention features a ligand agonist of formyl peptide receptor like-1 receptor comprising the amino acid sequence of SEQ ID NO: 1, or an analog thereof.

In another aspect the invention features a ligand agonist of formyl peptide receptor like-1 receptor comprising the amino acid sequence of SEQ ID NO: 2, or an analog thereof.

In another aspect the invention features a ligand agonist of formyl peptide receptor like-1 receptor comprising the amino acid sequence of SEQ ID NO: 3, or an analog thereof.

In another aspect the invention features a ligand agonist of formyl peptide receptor like-1 receptor comprising the amino acid sequence of SEQ ID NO: 4, or an analog thereof.

In another aspect the invention features a ligand agonist of formyl peptide receptor like-1 receptor comprising the amino acid sequence of SEQ ID NO: 5, or an analog thereof.

In another aspect the invention features a ligand agonist of formyl peptide receptor like-1 receptor comprising the amino acid sequence of SEQ ID NO: 6, or an analog thereof.

In an embodiment, the ligand agonist is a chemically synthesized polypeptide or analog thereof. In a preferred embodiment, the ligand agonist comprises an amino acid sequence selected from the group consisting of SEQ ID NO: 1, SEQ ID NO: 2, SEQ ID NO: 3, SEQ ID NO: 4, SEQ ID NO: 5, and SEQ ID NO: 6, or an analog thereof.

In another aspect, the invention features a recombinant cell which comprises a heterologous formyl peptide receptor like-1 (FPRL-1) receptor expressed in the cell membrane of the cell such that signal transduction activity via the receptor is modulated by interaction of an extracellular region of the receptor with an extracellular signal; and a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby causing a detectable signal to be generated.

The ligand agonist is as hereinbefore defined. In one embodiment, the ligand agonist has an $EC_{50}$ of $2 \times 10^{-5}$ M or less and comprises a polypeptide comprising from 3 to 80 amino acid residues, more preferably from 3 to 40 amino acid residues, more preferably from 3 to 20 amino acid residues, and still more preferably from 3 to 13 amino acid residues. In a preferred embodiment, the ligand agonist comprises an amino acid sequence selected from the group consisting of SEQ ID NO: 1, SEQ ID NO: 2, SEQ ID NO: 3, SEQ ID NO: 4, SEQ ID NO: 5, and SEQ ID NO: 6, or an analog thereof.

In another embodiment, the heterologous FPRL-1 receptor is coupled to a signal transduction pathway. In yet another embodiment, the heterologous FPRL-1 receptor acts as a surrogate for an endogenous cell receptor in a signal transduction pathway of the cell and wherein binding of said ligand agonist to said receptor activates the signal transduction activity of said receptor thereby generating a detectable signal.

In yet another embodiment, the FPRL-1 receptor is associated with an indicator molecule which provides a detectable signal upon binding of the ligand agonist to the receptor. In still another embodiment, the ligand agonist is associated with an indicator molecule which provides a detectable signal upon binding of the ligand agonist to the receptor. In a preferred embodiment, the indicator molecule comprises GFP or a β-arrestin-GFP conjugate.

In one embodiment, the recombinant cell further comprises a heterologous test polypeptide, wherein the heterologous test polypeptide is transported to a location allowing interaction with the extracellular region of the FPRL-1 receptor expressed in the cell membrane; and wherein the heterologous test polypeptide is expressed at a sufficient level such that modulation of the signal transduction activity of the receptor by the heterologous polypeptide alters the detectable signal. In another embodiment, the heterologous test polypeptide includes a signal sequence that facilitates transport of the polypeptide to a location allowing interaction with the extracellular region of the receptor.

In another embodiment, the recombinant cell further comprises a reporter construct that is activated by the signal transduction pathway, wherein the detectable signal provided by the ligand agonist is mediated by the reporter construct.

In yet another embodiment, the detectable signal is selected from the group consisting of a growth signal, intracellular calcium mobilization, an optical signal, second messenger production, changes in GTP hydrolysis and phospholipid hydrolysis.

In a preferred embodiment, the heterologous FPRL-1 is human FPRL-1. In one embodiment, the recombinant cell is a prokaryotic cell. In a preferred embodiment, the recombinant cell is a eukaryotic cell. In another preferred embodiment, the recombinant cell is a yeast cell, and the heterologous FPRL-1 receptor acts as a surrogate for an endogenous yeast pheromone receptor in a pheromone response pathway of the yeast cell. In a particularly preferred embodiment, the yeast cell belongs to the species Saccharomyces cerevisiae.

In another aspect, the invention features a recombinant yeast cell which comprises a heterologous formyl peptide receptor like-1 (FPRL-1) receptor expressed in the cell membrane of the yeast cell such that signal transduction activity via the receptor is modulated by interaction of an extracellular region of the receptor with an extracellular signal; and a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby causing a detectable signal to be generated. The ligand agonist is as hereinbefore defined.

In one embodiment, the yeast cell further comprises a heterologous test polypeptide, wherein the heterologous test polypeptide is transported to a location allowing interaction with the extracellular region of the FPRL-1 receptor expressed in the cell membrane; and wherein the heterologous test polypeptide is expressed at a sufficient level such that modulation of the signal transduction activity of the receptor by the heterologous test polypeptide alters the detectable signal.

In another embodiment, the heterologous polypeptide includes a signal sequence that facilitates transport of the polypeptide to a location allowing interaction with the extracellular region of the receptor. In a preferred embodiment, the signal sequence corresponds to a leader peptide of the Saccharomyces cerevisiae α factor or a-factor.

In another embodiment, the heterologous FPRL-1 receptor acts as a surrogate for an endogenous yeast pheromone receptor in a pheromone response pathway of the yeast cell, and wherein binding of the ligand agonist to the receptor activates the signal transduction activity of the receptor to thereby generate a detectable signal.

In a preferred embodiment, the yeast cell further comprises a mutation in at least one gene selected from the group consisting of STP22, VPS1, KRE1, CAV1, STE50, SGV1, PIK1, AFR1, FAR1, SST2, BAR1, SVG1, STE2, STE3, STE14, MFa1, MFa2, MFa1 and MFa2.

In yet another embodiment, the yeast cell further comprises a reporter construct that is activated by the pheromone response pathway, wherein the detectable signal provided by the ligand agonist is mediated by the reporter construct.

In another embodiment, the reporter construct comprises a pheromone-responsive promoter operably linked to a selectable gene. In a preferred embodiment, the pheromone-responsive promoter is the FUS1 promoter. In a more preferred embodiment, the selectable gene is selected from the group consisting of LACZ, URA3, LYS2, HIS3, LEU2, TRP1, ADE1, ADE2, ADE3, ADE4, ADE5, ADE7, ADE8, ARG1, ARG3, ARG4, ARG5, ARG6, ARG8, HIS1, HIS4, HIS5 ILV1, ILV2, ILV5, THR1, THR4, TRP2, TRP3, TRP4, TRP5, LEU1, LEU4, MET2, MET3, MET4, MET8, MET9, MET14, MET16, MET19, URA1, URA2, URA4, URA5, URA10, H0M3, H0M6, ASP3, CHO1, ARO2, ARO7, CYS3, OLE1, IN01, IN02, IN04, PR01, and PR03.

In a preferred embodiment, the yeast cell is a mutant strain of a yeast cell having a pheromone system pathway that is desensitized at slower rate than a wild type strain under the same conditions of continuous stimulation of the pheromone system pathway. In a preferred embodiment, the yeast cell has a ste14 mutation. In another preferred embodiment, the yeast cell has a ste2 or ste3 mutation.

The recombinant cells of the invention, particularly the recombinant yeast cells, described hereinabove, are useful in methods for identifying modulators of a heterologous formyl peptide receptor like-1 (FPRL-1) receptor. Thus, in one aspect, the invention features a method for identifying a modulator of a heterologous formyl peptide receptor like-1 (FPRL-1) receptor expressed by a cell, comprising:

providing a recombinant cell comprising:
   a heterologous FPRL-1 receptor expressed in the cell membrane of the cell such that signal transduction activity via the receptor is modulated by interaction of an extracellular region of the receptor with an extracellular signal, the heterologous FPRL-1 receptor acting as a surrogate for an endogenous cell receptor in a signal transduction pathway of the cell; and
   a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby activating the signal transduction activity of the FPRL-1 receptor and generating a detectable signal;
contacting the cell with a test compound; and
detecting an alteration in the signal generated by the ligand agonist to thereby identify a modulator of the receptor.

In one embodiment, the test compound is a non-peptidic compound. In another embodiment, the test compound is a heterologous polypeptide. In another embodiment, the test compound is a heterologous test polypeptide expressed by the yeast cell.

In another embodiment, the modulator is an agonist of the FPRL-1 receptor. In another embodiment, the modulator is an antagonist of the FPRL-1 receptor.

In one embodiment, the invention features a method for identifying a modulator of a heterologous formyl peptide receptor like-1 (FPRL-1) receptor expressed by a cell, comprising:

providing a recombinant cell comprising:
   a heterologous FPRL-1 receptor expressed in the cell membrane of the host cell such that signal transduction activity via the receptor is modulated by interaction of an extracellular region of the receptor with an extracellular signal, the heterologous FPRL-1 receptor acting as a surrogate for an endogenous cell receptor in a signal transduction pathway of the cell; and a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby activating the signal transduction activity of the FPRL-1 receptor and generating a detectable signal;

contacting the cell with each member of a library of test compounds; and detecting an alteration in the signal generated by the ligand agonist to thereby identify a modulator of the receptor.

In a preferred embodiment, the library of test compounds is a library of heterologous polypeptides and the library is expressed by the cell. Preferably, the library of test compounds includes more than 1000 different compounds. In another embodiment, the library of test compounds is a library of non-peptidic compounds.

In yet another embodiment, the invention features a method for identifying a modulator of a heterologous formyl peptide receptor like-1 (FPRL-1) receptor expressed by a cell, comprising:

providing a mixture of recombinant cells, each cell of which has a cell membrane and comprises:

a heterologous formyl peptide receptor like-1 (FPRL-1) receptor expressed in the cell membrane of the yeast cell such that signal transduction activity via the receptor is modulated by interaction of an extracellular region of the receptor with an extracellular signal, the heterologous FPRL-1 receptor acting as a surrogate for an endogenous cell receptor in a signal transduction pathway of the cell;

a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby activating the signal transduction activity of the FPRL-1 receptor and generating a detectable signal; and a heterologous test polypeptide, wherein the heterologous polypeptide is transported to a location allowing interaction with the extracellular region of the receptor expressed in the cell membrane;

wherein collectively the mixture of cells expresses a library of the heterologous test polypeptides, the library being expressible at a sufficient level such that modulation of the signal transduction activity of the receptor by a heterologous polypeptide within the library alters the detectable signal generated by the ligand agonist; and detecting an alteration in the signal generated by the ligand agonist to thereby identify a modulator of the receptor.

In still another embodiment, the invention features a method for identifying a modulator of a heterologous formyl peptide receptor like-1 (FPRL-1) receptor expressed by a cell, comprising:

providing a first mixture of recombinant cells, each cell of which has a cell membrane and comprises:

a heterologous formyl peptide receptor like-1 (FPRL-1) receptor expressed in the cell membrane of the yeast cell such that signal transduction activity via the receptor is modulated by interaction of an extracellular region of the receptor with an extracellular signal, the heterologous FPRL-1 receptor acting as a surrogate for an endogenous cell receptor in a signal transduction pathway of the cell; and a ligand agonist of the FPRL-1 receptor comprising a polypeptide or analog thereof, wherein the ligand agonist is transported to a location allowing interaction with the extracellular region of the FPRL-1 receptor expressed in the cell membrane, and is expressed at a level sufficient for the ligand agonist to bind to and activate the FPRL-1 receptor, thereby activating the signal transduction activity of the FPRL-1 receptor and generating a detectable signal;

contacting the first mixture with a second mixture of cells, wherein collectively the second mixture of cells expresses a library of heterologous test polypeptides that are transported to a location allowing interaction with the extracellular region of the FPRL-1 receptor expressed in the cell membrane of the cells of the first mixture; and detecting an alteration by a heterologous test polypeptide of the signal generated by the ligand agonist to thereby identify a modulator of the receptor.

In another embodiment, the invention features a method for identifying a modulator of a heterologous formyl peptide receptor like-1 (FPRL-1) receptor expressed by a cell, comprising:

providing a recombinant cell comprising a heterologous FPRL-1 receptor expressed in the cell membrane of the yeast cell such that signal transduction activity via the receptor is modulated by interaction of an extracellular region of the receptor with an extracellular signal; and contacting the recombinant cell with a ligand agonist of the FPRL-1 receptor, the ligand agonist comprising a polypeptide or analog thereof, to permit the ligand agonist to bind to and activate the FPRL-1 receptor, thereby activating the signal transduction activity of the FPRL-1 receptor and generating a detectable signal;

contacting the cell with a test compound; and detecting an alteration in the signal generated by the ligand agonist to thereby identify a modulator of the receptor.

In another embodiment, the heterologous FPRL-1 receptor is coupled to a signal transduction pathway. In yet another embodiment, the heterologous FPRL-1 receptor acts as a surrogate for an endogenous cell receptor in a signal transduction pathway of the cell and wherein binding of said ligand agonist to said receptor activates the signal transduction activity of said receptor thereby generating a detectable signal.

In yet another embodiment, the FPRL-1 receptor is associated with an indicator molecule which provides a detectable signal upon binding of the ligand agonist to the receptor. In still another embodiment, the ligand agonist is associated with an indicator molecule which provides a detectable signal upon binding of the ligand agonist to the receptor. In a preferred embodiment, the indicator molecule comprises GFP or a β-arrestin-GFP conjugate.

In another embodiment, the FPRL-1 receptor and the ligand agonist are associated with first and second indicator molecules, respectively. In a preferred embodiment, the first and second indicator molecules comprise fluorescent indicator molecules. In another preferred embodiment, the detectable signal comprises fluorescent resonance energy transfer between the first and second fluorescent indicator molecules.

In another embodiment, the invention provides a method for identifying a modulator of a heterologous formyl peptide receptor like-1 (FPRL-1) receptor expressed in the membrane of a cell, the method comprising:

contacting the cell with a a ligand agonist of the FPRL-1 receptor, the ligand agonist comprising a polypeptide, or analog thereof, in the presence of a test compound under conditions to permit binding of the ligand agonist to the receptor; and determining the inhibition by the test compound of binding of the ligand agonist to the receptor, by assessing the amount of the ligand agonist bound to the receptor, such that reduction of binding of the ligand agonist to the receptor identifies the test compound as a modulator of the receptor.

In one embodiment, the heterologous FPRL-1 receptor is coupled to a signal transduction pathway. In another embodiment, the heterologous FPRL-1 receptor acts as a surrogate for an endogenous cell receptor in a signal transduction pathway of the cell and wherein binding of the ligand agonist to the receptor activates the signal transduction activity of the receptor thereby generating a detectable signal.

In yet another embodiment, the FPRL-1 receptor is associated with an indicator molecule which provides a detectable signal upon binding of the ligand agonist to the receptor. In still another embodiment, the ligand agonist is associated with an indicator molecule which provides a detectable signal upon binding of the ligand agonist to the receptor. In a preferred embodiment, the indicator molecule comprises GFP or a β-arrestin-GFP conjugate.

In another embodiment, the FPRL-1 receptor and the ligand agonist are associated with first and second indicator molecules, respectively. In a preferred embodiment, the first and second indicator molecules comprise fluorescent indicator molecules. In another preferred embodiment, the detectable signal comprises fluorescent resonance energy transfer between the first and second fluorescent indicator molecules.

In another embodiment, the invention features a method for identifying a modulator of a heterologous formyl peptide receptor like-1 (FPRL-1) receptor expressed by a cell, comprising:

providing a first mixture of recombinant cells, each cell of which has a cell membrane and comprises;
a heterologous FPRL-1 receptor expressed in the cell membrane of the cell such that signal transduction activity via the receptor is modulated by interaction of an extracellular region of the receptor with an extracellular signal, the heterologous FPRL-1 receptor acting as a surrogate for an endogenous cell receptor in a signal transduction pathway of the cell; and
contacting the recombinant cell with a ligand agonist of the FPRL-1 receptor comprising a polypeptide, or analog thereof, to permit the ligand agonist to bind to and activate the FPRL-1 receptor, thereby activating the signal transduction activity of the FPRL-1 receptor and generating a detectable signal;
contacting the first mixture with a second mixture of cells, wherein collectively the second mixture of cells expresses a library of heterologous test polypeptides that are transported to a location allowing interaction with the extracellular region of the FPRL-1 receptor expressed in the cell membrane of the host cells of the first mixture; and
detecting an alteration in the signal generated by the ligand agonist to thereby identify a modulator of the receptor.

DETAILED DESCRIPTION OF THE INVENTION

Figure 1:
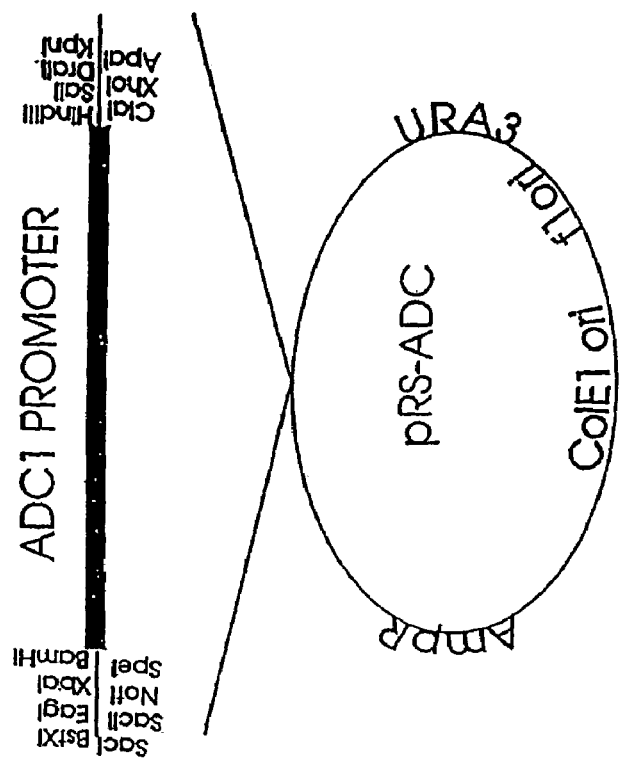
FIG. 1 depicts the structures of pAAH5 and pRS-ADC.
Figure 1:
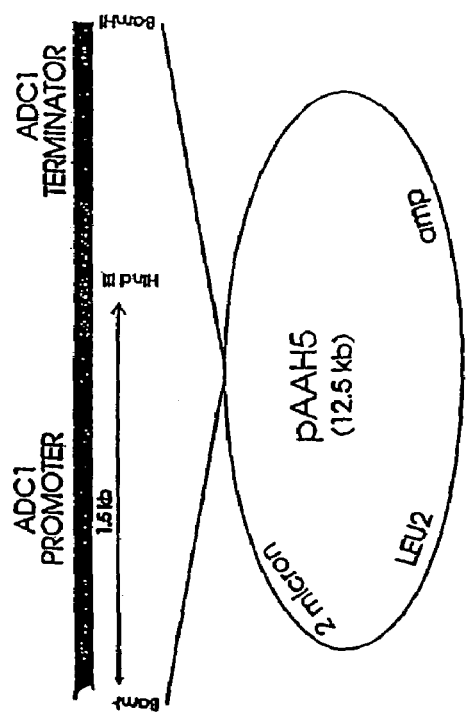

Proliferation, differentiation and death of eukaryotic cells are controlled by hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds. However, the rate at which receptors have been cloned has recently increased dramatically—existing families have been extended and new families recognized. In particular, the application of advanced cloning approaches has allowed the isolation of many receptors for which ligands are initially unknown. These are commonly referred to in the art as "orphan" receptors, and several have subsequently proved to be important pharmacological targets.

The present invention makes available a rapid, effective assay for screening and identifying pharmaceutically effective compounds that specifically interact with and modulate the activity of a cellular receptor or ion channel. The subject assay enables rapid screening of large numbers of polypeptides in a library to identifying those polypeptides which induce or antagonize receptor bioactivity. The library of polypeptides can be expressed within recombinant cells, or can be produced by standard peptide synthetic techniques and contacted with recombinant cells. The assay may also be used to screen large numbers of non-peptidic compounds that are contacted with recombinant cells.

The present invention also provides novel ligand agonists of human formyl peptide receptor like-1 (FPRL-1) receptor. The ligand agonists are useful in the assays of the invention to identify modulators of FPRL-1 receptor.

In general, the assay is characterized by the use of a mixture of recombinant cells to sample a variegated polypeptide library for receptor agonists or antagonists. As described with greater detail below, the reagent cells express both a target receptor protein capable of transducing a detectable signal in the reagent cell, and a test polypeptide for which interaction with the receptor is to be ascertained. Collectively, a culture of such reagent cells will provide a variegated library of potential receptor effectors and those members of the library which either agonize or antagonize the receptor function can be selected and identified by sequence.

One salient feature of the subject assay is the enhanced sensitivity resulting from expression of the test polypeptide in a cell which also serves as a reporter for the desired receptor-ligand interaction. To illustrate, where the detectable signal resulting from receptor engagement by an agonist provides a growth signal or drug resistance, individual cells expressing polypeptides which agonize receptor function can be amplified and isolated from a library culture.

Accordingly, the present invention provides a convenient format for discovering drugs which can be useful to modulate cellular function, as well as to understand the pharmacology of compounds that specifically interact with cellular receptors or ion channels. Moreover, the subject assay is particularly amenable to identifying ligands, natural or surrogate, for the FPRL-1 receptor.

I. Definitions

Before further description of the invention, certain terms employed in the specification, examples and appended claims are, for convenience, collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express the reporter gene construct, receptor or test polypeptide.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, "heterologous DNA" or "heterologous nucleic acid" includes DNA that does not occur naturally as part of the genome in which it is present, or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes test polypeptides, receptors, reporter genes, transcriptional and translational regulatory sequences, selectable or traceable marker proteins, such as a protein that confers drug resistance.

As used herein, "cell surface receptor" refers to molecules that occur on the surface of cells, interact with the extracellular environment, and transmit or transduce the information regarding the environment intracellularly in a manner that ultimately modulates transcription of specific promoters, resulting in transcription of specific genes.

As used herein, "extracellular signals" include a molecule or a change in the environment that is transduced intracellularly via cell surface proteins that interact, directly or indirectly, with the signal. An extracellular signal or effector molecule includes any compound or substance that in some manner specifically alters the activity of a cell surface protein. Examples of such signals include, but are not limited to, molecules such as acetylcholine, growth factors and hormones that bind to cell surface and/or intracellular receptors and ion channels and modulate the activity of such receptors and channels.

As used herein, "extracellular signals" also include as yet unidentified substances that modulate the activity of a cellular receptor, and thereby influence intracellular functions. Such extracellular signals are potential pharmacological agents that may be used to treat specific diseases by modulating the activity of specific cell surface receptors.

"Orphan receptor" is a designation given to a receptor for which no specific natural ligand has been described.

The terms "operatively linked", "operably linked", and "associated with" are used herein interchangeably and are intended to mean that molecules are functionally coupled to each other. In the case of polypeptides, these are connected in a manner such that each polypeptide can serve its intended function. Typically, two polypeptides are covalently attached through peptide bonds.

As used herein, a "reporter gene construct" is a nucleic acid that includes a "reporter gene" operatively linked to transcriptional regulatory sequences. Transcription of the reporter gene is controlled by these sequences. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences that are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter translation of the resulting mRNA, thereby altering the amount of reporter gene product.

"Signal transduction" is the processing of chemical signals from the cellular environment through the cell membrane, and may occur through one or more of several mechanisms, such as phosphorylation, activation of ion channels, effector enzyme activation via guanine nucleotide binding protein intermediates, formation of inositol phosphate, activation of adenylyl cyclase, and/or direct activation (or inhibition) of a transcriptional factor.

The term "modulation of a signal transduction activity of a receptor protein" in its various grammatical forms, as used herein, designates induction and/or potentiation, as well as inhibition of one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand. Receptor effectors can modulate signal transduction when used alone, i.e., can be surrogate ligands, or can alter signal transduction in the presence of the natural ligand, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

The term "autocrine cell", as used herein, refers to a cell which produces a substance which can stimulate a receptor located on or within the same cell as produces the substance. For example, wild-type yeast α and a cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) expressing the receptor are called "autocrine cells", though it might be more precise to call them "putative autocrine cells". Of course, in a library of such cells, in which a multitude of different peptides are produced, it is likely that one or more of the cells will be "autocrine" in the stricter sense of the term.

The term "amino acid" as used herein, refers to an amino acid residue and is also intended to include analogs, derivatives and congeners of any specific amino acid residue.

The terms "protein", and "polypeptide" and "peptide" are used interchangeably herein.

The term "peptide" is used herein to refer to a chain of two or more amino acids or amino acid analogs (including non-naturally occurring amino acids), with adjacent amino acids joined by peptide (—NHCO—) bonds. Thus, the peptides of the present invention include oligopeptides, polypeptides, and proteins.

The terms "mimetope" and "peptidomimetic" are used interchangeably herein. A "mimetope" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide (e.g., FPRL-1 agonists). Examples of amino acid mimetics include D-amino acids. Peptides substituted with one or more D-amino acids may be made using well known peptide synthesis procedures. Additional substitutions include amino acid analogs having variant side chains with functional groups, for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine.

As used herein an "analog" of a compound X refers to a compound which retains chemical structures of X necessary for functional activity of X, yet which also contains certain chemical structures which differ from X. An example of an analog of a naturally-occurring peptide is a peptide which includes one or more non-naturally-occurring amino acids. The term "analog" is also intended to include modified mimetopes and/or peptidomimetics, modified peptides and polypeptides, and allelic variants of peptides and polypeptides. Analogs of a peptide will therefore produce a peptide analog that is substantially homologous to the original peptide.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

Sequence percent homology can be determined as described by Murphy et al. (1992) *J. Biol Chem.* 267:7637-7643 and Ye et al. (1992) *Biochem Biophys Res. Comm.* 184:582-589. Generally, to determine the percent homology of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The term "yeast", as used herein, includes not only yeast in a strictly taxonomic sense, i.e., unicellular organisms, but also yeast-like multicellular fungi or filamentous fungi.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of an inactivated gene of the host cell is supplied by an exogenous nucleic acid.

The term "receptor," as used herein, encompasses both naturally occurring and mutant receptors.

The "exogenous receptors" of the present invention may be any G protein-coupled receptor which is exogenous to the cell which is to be genetically engineered for the purpose of the present invention.

As used herein, the term "contacting" (i.e., contacting a cell, e.g., a yeast cell, with a test compound) is intended to include incubating the test compound and the yeast cell together in vitro (e.g., adding the compound to cells in culture).

As used herein, the term "test compound" is intended to refer to a compound that has not previously been identified as, or recognized to be, a modulator of a recombinant cell activity, e.g., yeast cell activity. The term "test compound" is also intended to refer to a compound not previously identified as a modulator of activity produced by cells engineered to express the library of test compounds, e.g., polypeptides or analogs thereof. The library of test compounds can be produced by the same cell that expresses the heterologous receptor. The library of test compounds can be produced by a different cell than the one which expresses the heterologous receptor and is contacted with the cell that expresses the heterologous receptor. The term "test compound" is also intended to refer to polypeptides or analogs thereof that are not expressed in the cell but are added exogenously to the cell. The term "test compound" is also intended to refer to one or more non-peptidic compounds not previously identified as a modulators of activity.

The term "library of test compounds" can refer to a panel comprising a multiplicity of test compounds. The term "library of test compounds" can also refer to a single cell expressing a single compound, wherein collectively a mixture of such cells expresses a library of compounds.

II. Overview of Assay

The present invention relates to a rapid, reliable and effective assay for screening and identifying pharmaceutically effective compounds that specifically interact with and modulate the activity of a cellular receptor or ion channel. The subject assay enables rapid screening of large numbers of polypeptides in a library to identify those polypeptides which agonize or antagonize receptor bioactivity. There are multiple methods of characterizing the assay. In one aspect, the assay is characterized by the use of recombinant cells, each cell of which includes (i) a target FPRL-1 receptor protein whose signal transduction activity can be modulated by interaction with an extracellular signal, the transduction activity being able to generate a detectable signal, (ii) a ligand agonist of the target FPRL-1 receptor protein expressed in the recombinant cell, and (iii) test compound expressed in the recombinant cell that antagonizes or agonizes the interaction between the target FPRL-1 receptor protein and the ligand agonist. In preferred embodiments, the test compounds are a library of polypeptides and includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another aspect, the assay is characterized by the use of recombinant cells, each cell of which includes (i) a target FPRL-1 receptor protein whose signal transduction activity can be modulated by interaction with an extracellular signal, the transduction activity being able to generate a detectable signal and, (ii) a ligand agonist of the target FPRL-1 receptor protein expressed in the recombinant cell. Test compounds that antagonize or agonize the interaction between the target FPRL-1 receptor protein and the ligand agonist, can be identified by contacting the recombinant cells with a test compound, or a library of test compounds. In preferred embodiments, the test compounds are a library of polypeptides and includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library. In other preferred embodiments, the test compound, or library of test compounds are non-peptidic compounds including at least $10^3$ different non-peptidic compounds, though more preferably at least $10^5$, $10^6$, or $10^7$ different non-peptidic compounds.

In another aspect, the assay is characterized by the use of recombinant cells, each cell of which includes (i) a target FPRL-1 receptor protein whose signal transduction activity can be modulated by interaction with an extracellular signal, the transduction activity being able to generate a detectable signal and, (ii) a ligand agonist of the target FPRL-1 receptor protein expressed in the recombinant cell. Test compounds that antagonize or agonize the interaction between the target FPRL-1 receptor protein and the ligand agonist can be identified by contacting the recombinant cells engineered to express the library of test polypeptides. In preferred embodiments, the test compounds are a library of polypeptides and includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another aspect, the assay is characterized by the use of recombinant cells, each cell of which (i) includes a target FPRL-1 receptor protein whose signal transduction activity can be modulated by interaction with an extracellular signal, the transduction activity being able to generate a detectable signal and, (ii) is contacting an exogenous ligand agonist of the target FPRL-1 receptor protein. Test compounds that antagonize or agonize the interaction between the target FPRL-1 receptor protein and the ligand agonist can be identified by contacting the recombinant cells with a test compound, or a library of test compounds. In preferred embodiments, the test compounds are a library of polypeptides and includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library. In other preferred embodiments, the test compound, or library of test compounds are non-peptidic compounds including at least $10^3$ different non-peptidic compounds, though more preferably at least $10^5$, $10^6$, or $10^7$ different non-peptidic compounds.

In another aspect, the assay is characterized by the use of recombinant cells, each cell of which (i) includes a target FPRL-1 receptor protein whose signal transduction activity can be modulated by interaction with an extracellular signal, the transduction activity being able to generate a detectable signal and, (ii) is contacting an exogenous ligand agonist of the target FPRL-1 receptor protein. Test compounds that antagonize or agonize the interaction between the target FPRL-1 receptor protein and the ligand agonist can be identified by contacting the recombinant cells with a test compound, or a library of test compounds. Test compounds that antagonize or agonize the interaction between the target FPRL-1 receptor protein and the ligand agonist can also be identified by contacting the recombinant cells with cells engineered to express the library of test polypeptides. In preferred embodiments, the test compounds are a library of polypeptides and includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

The ability of particular constituents of the peptide library to modulate the signal transduction activity of the target receptor can be scored for by detecting up- or down-regulation of the detection signal. For example, second messenger generation (e.g., GTPase activity, phospholipid hydrolysis, or protein phosphorylation) via the receptor can be measured directly. Alternatively, the use of a reporter gene can provide a convenient readout. In any event, a statistically significant change in the detection signal can be used to facilitate isolation of those cells from the mixture which contain a nucleic acid encoding a test polypeptide which is an effector of the target receptor.

By this method, test polypeptides which induce the receptor's signaling can be screened. If the test polypeptide does not appear to induce the activity of the receptor protein, the assay may be repeated and modified by the introduction of a step in which the recombinant cell is first contacted with a known activator of the target receptor to induce signal transduction from the receptor, and the test polypeptide is assayed for its ability to inhibit the activity of the receptor, e.g., to identify receptor antagonists. In yet other embodiments, the peptide library can be screened for members which potentiate the response to a known activator of the receptor. In this respect, surrogate ligands identified by the present assay for orphan receptors can be used as the exogenous activator, and further peptide libraries screened for members which potentiate or inhibit the activating peptide. Alternatively, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though it is preferably produced by the reagent cell, thereby providing an autocrine cell.

In developing the recombinant cell assays, it was recognized that a frequent result of receptor-mediated responses to extracellular signals was the transcriptional activation or inactivation of specific genes after exposure of the cognate receptor to an extracellular signal that induces such activity. Thus, transcription of genes controlled by receptor-responsive transcriptional elements often reflects the activity of the surface protein by virtue of transduction of an intracellular signal.

To illustrate, the intracellular signal that is transduced can be initiated by the specific interaction of an extracellular signal, particularly a ligand, with a cell surface receptor on the cell. This interaction sets in motion a cascade of intracellular events, the ultimate consequence of which is a rapid and detectable change in the transcription or translation of a gene. By selecting transcriptional regulatory sequences that are responsive to the transduced intracellular signals and operatively linking the selected promoters to reporter genes, whose transcription, translation or ultimate activity is readily detectable and measurable, the transcription based assay provides a rapid indication of whether a specific receptor or ion channel interacts with a test peptide in any way that influences intracellular transduction. Expression of the reporter gene, thus, provides a valuable screening tool for the development of compounds that act as agonists or antagonists of a cell receptor or ion channel.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of the test compound or it may be compared with the amount of transcription in a substantially identical cell that lacks the specific receptors. A control cell may be derived from the same cells from which the recombinant cell was prepared but which had not been modified by introduction of heterologous DNA, e.g., that encoding the test polypeptide. Alternatively, it may be a cell in which the specific receptors are removed. Any statistically or otherwise significant difference in the amount of transcription indicates that the test polypeptide has in some manner altered the activity of the specific receptor.

In other preferred embodiments, the reporter or marker gene provides a selection method such that cells in which the peptide is a ligand for the receptor have a growth advantage. For example the reporter could enhance cell viability, relieve a cell nutritional requirement, and/or provide resistance to a drug.

With respect to the target receptor, it may be endogenously expressed by the host cell, or it may be expressed from a heterologous gene that has been introduced into the cell. Methods for introducing heterologous DNA into eukaryotic cells are of course well known in the art and any such method may be used. In addition, DNA encoding various receptor proteins is known to those of skill in the art, or it may be cloned by any method known to those of skill in the art. In certain embodiments, such as when an exogenous receptor is expressed, it may be desirable to inactivate, such as by deletion, a homologous receptor present in the cell.

The subject assay is useful for identifying polypeptides that interact with any receptor protein whose activity ultimately induces a signal transduction cascade in the host cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone receptors. In preferred embodiments the method described herein is used for identifying ligands for "orphan receptors" for which no ligand is known.

In preferred embodiments, the method described herein is used to identify modulators of FPRL-1 receptor by detecting alterations in signals generated by the novel FPRL-1 ligand agonists of the invention. Thus, the method can be used to identify agonists and antagonists of the FPRL-1 receptor.

In embodiments in which cell surface receptors are the assay targets, it will be desirable for each of the peptides of the peptide library to include a signal sequence for secretion, e.g., which will ensure appropriate transport of the peptide to the endoplasmic reticulum, the golgi, and ultimately to the cell surface so that it is able to interact with cell surface receptors. In the case of yeast cells, the signal sequence will transport peptides to the periplasmic space.

Any transfectable cell that can express the desired cell surface protein in a manner such that the protein functions to transduce intracellularly an extracellular signal may be used. The cells may be selected such that they endogenously express the target receptor protein or may be genetically engineered to do so.

Interactions between the target FPRL-1 receptor protein and ligand agonists of the FPRL-1 receptor (e.g., binding of a ligand agonist to the FPRL-1 receptor) can be detected using an indicator molecule or construct that provides a detectable signal. Such indicator molecules/constructs can be associated with the FPRL-1 receptor and/or a ligand agonist of the receptor, such that a detectable signal is generated when the receptor is activated as a result of ligand binding to the receptor. Indicator molecules/constructs that are useful in accordance with the invention will be readily apparent to the skilled artisan. These include, for example, phospholipase C, phospholipase D, and radioisotope labels, among others.

An example of an indicator molecule/construct that provides a detectable signal is a fluorescent reporter molecule, for example green fluorescent protein (GFP) (See e.g., Cubitt et al., WO 98/06737, U.S. Pat. Nos. 5,777,079 and 5,625,048, to Tsien et al.). A real time, single cell-based assay using a fluorescent reporter molecule is described in L. S. Barat et. al. *J. Biol. Chem.* (1997) 272(44):27497-27500. In accordance with this assay, the interaction of GPCR with β-arrestin-GFP conjugate is used to monitor GPCR activation (e.g., binding of a ligand to the GPCR) or GPCR-β-arrestin-GFP conjugate interactions.

In one embodiment of the invention, the target FPRL-1 receptor protein is associated with (e.g., labeled with) an indicator molecule, for example, GFP. The interaction of the GFP labeled FPRL-1 receptor protein with the ligand agonist of FPRL-1 receptor can be detected by standard techniques used to monitor fluorescent molecules, for example, by confocal microscopy. Thus, the invention provides a method for identifying a test compound that antagonizes the interaction between the GFP labeled FPRL-1 receptor protein and the ligand agonist, by measuring reduction of the fluorescent signal that would otherwise be generated by interaction (binding) of the ligand agonist to the receptor in the absence of an antagonist.

Alternatively, the ligand agonist of the FPRL-1 receptor can be associated with (e.g., labeled with) an indicator molecule, for example, GFP to provide a ligand agonist-GFP conjugate. The interaction of target FPRL-1 receptor protein with the ligand agonist-GFP conjugate can be detected by, for example, confocal microscopy. By so labeling the ligand agonist, the invention provides a method of identifying a test compound that antagonizes the interaction between the target FPRL-1 receptor protein and the ligand agonist-GFP conjugate, by measuring reduction of the fluorescent signal that would otherwise be generated by interaction (binding) of the ligand agonist to the receptor in the absence of an antagonist.

In yet another embodiment, the target FPRL-1 receptor protein is labeled with a first fluorescent indicator molecule, and the ligand agonist of the FPRL-1 receptor is labeled with a second fluorescent indicator molecule. Fluorescence resonance energy transfer (FRET) can then occur when the first and second indicator molecules are in close proximity to each other. Assays using FRET are known to one of skilled in the art and are described in, for example, U.S. Pat. No. 5,342,789 to Chick et al., Thus, in accordance with the invention, a FRET-based assay can be used to detect signal transduction activity when a ligand agonist of the FPRL-1 receptor, labeled with the second fluorescent indicator molecule, binds to and activates the target FPRL-1 receptor protein labeled with the first fluorescent indicator molecule. Detection is achieved by measuring the fluorescence resonance transfer between the first and second indicator molecules when these come into close proximity as a result of binding of the ligand to the receptor. The target FPRL-1 receptor protein and the ligand agonist of the FPRL-1 receptor so labeled may be exogenous components of an in vitro assay, or may be expressed within a recombinant host cell.

In yet another embodiment of the invention, a test compound that antagonizes the interaction between a target FPRL-1 receptor protein labeled with a first fluorescent indicator molecule, and a ligand agonist of the FPRL-1 receptor labeled with a second fluorescent indicator molecule can also be detected using FRET. Thus, if the compound is an antagonist of the FPRL-receptor, it will alter the fluorescence resonance transfer between the first and second indicator molecules that otherwise occurs when these come into close proximity as a result of binding of the ligand to the receptor in the absence of the antagonist. This alteration can be measured by methods well known in the art.

In still another embodiment, competition between a ligand agonist of the invention and a test compound for binding to the FPRL-1 receptor can form the basis for an assay to identify the compound as a modulator of the receptor. Thus, the invention provides a method for identifying a modulator of a heterologous FPRL-1 receptor expressed in the membrane of a cell. The cell or a cell membrane containing the receptor is contacted with a ligand agonist of the invention in the presence of a test compound under conditions that permit binding of the ligand agonist to the receptor. Inhibition by the test compound of binding of the ligand agonist to the receptor is determined by detecting the amount of ligand agonist actually bound to the receptor as compared to the amount of ligand bound to the receptor in the absence of the compound. A test compound that reduces binding of the ligand to the receptor is thereby identified as a modulator of the receptor.

The preparation of cells which express the FPRL-1 receptor, a peptide library, and a reporter gene expression construct, are described. These cells have been used to identify novel ligands for this receptor. The cells for the identification of receptor ligands can be used in drug screening assays to discover agents capable of modulating receptor activity.

Any cell surface protein that is known to those of skill in the art or that may be identified by those of skill in the art may be used in the assay. The cell surface protein may be endogenously expressed on the selected cell or it may be expressed from cloned DNA.

III. Host Cells

Suitable host cells for generating the subject assay include prokaryotes, yeast, or higher eukaryotic cells, especially mammalian cells. Prokaryotes include gram negative or gram positive organisms. Examples of suitable mammalian host cell lines include the COS-7 line of monkey kidney cells (ATCC CRL 1651) (Gluzman (1981) *Cell* 23:175) CV-1 cells (ATCC CCL 70), L cells, C127, 3T3, Chinese hamster ovary (CHO), HeLa and BHK cell lines.

If yeast cells are used, the yeast may be of any species which are cultivable and in which an exogenous receptor can be made to engage the appropriate signal transduction machinery of the host cell. Suitable species include *Kluyverei lactis, Schizosaccharomyces pombe*, and *Ustilaqo maydis; Saccharomyces cerevisiae* is preferred. Other yeast which can be used in practicing the present invention are *Neurospora crassa, Aspergillus niger, Aspergillus nidulans, Pichia pastoris, Candida tropicalis*, and *Hansenula polymorpha*.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The reporter gene may be an unmodified gene already in the host cell pathway, such as the genes responsible for growth arrest in yeast. It may be a host cell gene that has been operably linked to a "receptor-responsive" promoter. Alternatively, it may be a heterologous gene that has been so linked. Suitable genes and promoters are discussed below. In other embodiments, second messenger generation can be measured directly in the detection step, such as mobilization of intracellular calcium or phospholipid metabolism are quantitated. Accordingly, it will be understood that to achieve selection or screening, the host cell must have an appropriate phenotype. For example, introducing a pheromone-responsive chimeric HIS3 gene into a yeast that has a wild-type HIS3 gene would frustrate genetic selection. Thus, to achieve nutritional selection, an auxotrophic strain is wanted.

To further illustrate, in a preferred embodiment of the subject assay using a yeast host cell, the yeast cells possess one or more of the following characteristics: (a) the endogenous FUS1 gene has been inactivated; (b) the endogenous SST2 gene, and/or other genes involve in desensitization, has been inactivated; (c) if there is a homologous, endogenous receptor gene it has been inactivated; and (d) if the yeast produces an endogenous ligand to the exogenous receptor, the genes encoding for the ligand been inactivated.

Other complementations for use in the subject assay can be constructed without any undue experimentation. Indeed, many genetic complementations between yeast and mammalian signal transduction proteins have been described in the art. For example, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

IV. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be a DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, New York, 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

Preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

The transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al. (1978) *Nature* 273:111). Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (1983, *Mol. Cell Biol.* 3:280). A useful system for stable high level expression of mammalian receptor cDNAs in C127 murine mammary epithelial cells can be constructed substantially as described by Cosman et al. (1986, *Mol. Immunol.* 23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs into *Saccharomyces cerevisiae* (see, for example, Broach et al. (1983) in *Experimental Manipulation of Gene Expression*, ed. M. Inouye Academic Press, p. 83, incorporated by reference herein). These vectors can replicate in *E. coli* because of the presence of the pBR322 ori, and in *Saccharomyces cerevisiae* due to the replication determinant of the yeast 2 micron plasmid. In addition, drug resistance markers such as ampicillin can be used.

Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., (1980) *J. Biol. Chem.* 255, 2073 or other glycolytic enzymes (Hess et al., (1968) *J. Adv. Enzyme Req.* 7, 149; and Holland et al. (1978) *Biochemistry* 17, 4900, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Promoters that are active in only one of the two haploid mating types may be appropriate in certain circumstances. Among these haploid-specific promoters, the pheromone promoters MFa1 and MFα1 are of particular interest.

In some instances, it may be desirable to derive the host cell using insect cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Libraries of random peptides or cDNA fragments may be expressed in a multiplicity of ways, including as portions of chimeric proteins. As described below, where secretion of the peptide library is desired, the peptide library can be engineered for secretion or transport to the extracellular space via the yeast pheromone system.

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

V. Periplasmic Secretion

If yeast cells are used as the host cell it will be noted that the yeast cell is bounded by a lipid bilayer called the plasma membrane. Between this plasma membrane and the cell wall is the periplasmic space. Peptides are secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist. In an alternative mechanism, the expressed ligand agonist may secreted into the periplasm yeast cells to enter into the periplasmic space and interact with the receptor.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

VI. G Protein-Coupled Receptors.

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein.

The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to receptor, the receptor changes conformation and this alters its interaction with the G protein. This spurs the α subunit to release GDP, and the more abundant nucleotide guanosine triphosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, several different G protein-dependent effectors.

Most G protein-coupled receptors are comprised of a single protein chain that is threaded through the plasma membrane seven times. Such receptors are often referred to as seven-transmembrane domain receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993) 321, 173; Birkenbach et al. (1993) *J. Virol.* 67, 2209.

The "exogenous receptors" of the present invention may be any G protein-coupled receptor which is exogenous to the cell which is to be genetically engineered for the purpose of the present invention. This receptor may be a plant or animal cell receptor. Screening for binding to plant cell receptors may be useful in the development of, e.g., herbicides and fungicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline., histamine, noradrenaline, noradrenaline, noradrenaline., tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (1 h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Suitable examples of G-protein coupled receptors include, but are not limited to, dopaminergic, muscarinic cholinergic, α-adrenergic, β-adrenergic, opioid (including delta and mu), cannabinoid, serotoninergic, and GABAergic receptors. Preferred receptors include the 5HT family of receptors, dopamine receptors, C5a receptor and FPRL-1 receptor, cyclo-histidyl-proline-diketoplperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Y1 or galanin. Other suitable receptors are listed in the art.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include Ste2, Ste3, and gal10. Suitable signal sequences include those of Ste2, Ste3 and of other genes which encode proteins secreted by yeast cells. Preferably, when a yeast cell is used, the codons of the gene would be optimized for expression in yeast. See Hoekema et al., (1987) *Mol. Cell. Biol.,* 7:2914-24; Sharp, et al., (1986)14:5125-43.

The homology of STRs is discussed in Dohlman et al., *Ann. Rev. Biochem.,* (1991) 60:653-88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that a foreign receptor which is expressed in yeast will functionally integrate into the yeast membrane, and there interact with the endogenous yeast G protein. More likely, either the receptor will need to be modified (e.g., by replacing its V-VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

Preferably, the yeast genome is modified so that it is unable to produce the yeast receptors which are homologous to the exogenous receptors in functional form. Otherwise, a positive assay score might reflect the ability of a peptide to activate the endogenous G protein-coupled receptor, and not the receptor of interest.

A. Chemoattractant Receptors

Chemoattractants are important mediators of inflammation, by functioning to recruit phagocytic cells at the site of injury or infection. They also mediate granule secretion, superoxide generation and upregulation of cell surface adhesion molecules, for example MAC-1. Exemplary chemoattractants include the complement component C5a, interleukin 8, leukotriene B4 and platelet activating factor. Many of these substances participate in pathophysiological conditions such as anaphylaxis and septic shock.

The N-formyl peptide receptor is a classic example of a calcium mobilizing G protein-coupled receptor expressed by neutrophils and other phagocytic cells of the mammalian immune system (Snyderman et al. (1988) *In Inflammation: Basic Principles and Clinical Correlates,* pp. 309-323). N-formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyrogenic infections. Similar signal transduction occurs in response to the inflammatory peptides C5a and IL-8.

Two other formyl peptide receptor like (FPRL) genes have been cloned based on their ability to hybridize to a fragment of the NFPR cDNA coding sequence. These have been named FPRL-1 (Murphy et al. (1992) *J. Biol Chem.* 267:7637-7643) and FPRL-2 (Ye et al. (1992) *Biochem Biophys Res. Comm.* 184:582-589). FPRL2 was found to mediate calcium mobilization in mouse fibroblasts transfected with the gene and exposed to formyl peptide. In contrast, although FPRL-1 was found to be 69% identical in amino acid sequence to NFPR, it did not bind prototype N-formyl peptide ligands when expressed in heterologous cell types. This led to the hypothesis of the existence of an as yet unidentified ligand for the FPRL1 orphan receptor (Murphy et al. supra).

The identification of ligands for the orphan FPRL1 receptor provides new opportunities for discovery of receptor agonists, that could potentially serve to enhance lymphocyte recruitment in immunocompromised patients, and for the discovery of receptor antagonists (described infra) that could prevent undesirable consequences of immune activation such as anaphylactic or septic shock. Thus, in accordance with the invention, ligands have been cloned for these orphan receptors (see Examples 6 and 7).

B. G Proteins

In the case of an exogenous G-protein coupled receptor, the yeast cell must be able to produce a G protein which is activated by the exogenous receptor, and which can in turn activate the yeast effector(s). The art suggests that the endogenous yeast Gα subunit (e.g., GPA) will be often be sufficiently homologous to the "cognate" Gα subunit which is natively associated with the exogenous receptor for coupling to occur. More likely, it will be necessary to genetically engineer the yeast cell to produce a foreign Gα subunit which can properly interact with the exogenous receptor. For example, the Gα subunit of the yeast G protein may be replaced by the Gα subunit natively associated with the exogenous receptor.

Dietzel and Kurjan, (1987) Cell, 50:1001) demonstrated that rat Gαs functionally coupled to the yeast Gβγ complex. However, rat Gαi2 complemented only when substantially overexpressed, while Gα0 did not complement at all. Kang, et al., Mol. Cell. Biol., (1990)10:2582). Consequently, with some foreign Gα subunits, it is not feasible to simply replace the yeast Gα.

If the exogenous G protein coupled receptor is not adequately coupled to yeast Gβγ by the Gα subunit natively associated with the receptor, the Gα subunit may be modified to improve coupling. These modifications often will take the form of mutations which increase the resemblance of the Gα subunit to the yeast Gα while decreasing its resemblance to the receptor-associated Gα. For example, a residue may be changed so as to become identical to the corresponding yeast Gα residue, or to at least belong to the same exchange group of that residue. After modification, the modified Gα subunit might or might not be "substantially homologous" to the foreign and/or the yeast Gα subunit.

The modifications are preferably concentrated in regions of the Gα which are likely to be involved in Gβγ binding. In some embodiments, the modifications will take the form of replacing one or more segments of the receptor-associated Gα with the corresponding yeast Gα segment(s), thereby forming a chimeric Gα subunit. (For the purpose of the appended claims, the term "segment" refers to three or more consecutive amino acids.) In other embodiments, point mutations may be sufficient.

This chimeric Gα subunit will interact with the exogenous receptor and the yeast Gβγ complex, thereby permitting signal transduction. While use of the endogenous yeast Gβγ is preferred, if a foreign or chimeric Gβγ is capable of transducing the signal to the yeast effector, it may be used instead.

C. Gα Structure

Some aspects of Gα structure are relevant to the design of modified Gα subunits. The amino terminal 66 residues of GPA1 are aligned with the cognate domains of human Gαs, Gαi2, Gαi3, Gα16 and transducin. In the GPA41Gα hybrids, the amino terminal 41 residues (derived from GPA1) are identical, end with the sequence-LEKQRDKNE- and are underlined for emphasis. All residues following the glutamate (E) residue at position 41 are contributed by the human Gα subunits, including the consensus nucleotide binding motif -GxGxxG-. Periods in the sequences indicate gaps that have been introduced to maximize alignments in this region. Codon bias is mammalian. For alignments of the entire coding regions of GPA1 with Gαs, Gαi, and GαO, Gαq and Gαz, see Dietzel and Kurjan (1987, Cell 50:573) and Lambright, et al. (1994, Nature 369:621-628). Additional sequence information is provided by Mattera, et al. (1986, FEBS Lett 206:36-41), Bray, et al. (1986, Proc. Natl. Acad. Sci USA 83:8893-8897) and Bray, et al. (1987, Proc Natl. Acad Sci USA 84:5115-5119).

The gene encoding a G protein homolog of Saccharomyces cerevisiae was cloned independently by Dietzel and Kurjan (supra) (SCG1) and by Nakafuku, et al. (1987 Proc Natl Acad Sci 84:2140-2144) (GPA1). Sequence analysis revealed a high degree of homology between the protein encoded by this gene and mammalian Gα. GPA1 encodes a protein of 472 amino acids, as compared with approximately 340-350 a.a. for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to GQS (33% identity, or 51% with conservative substitutions) (Nakafuku, et al., supra).

D. Construction of Chimeric Gα Subunits.

In designing Gα subunits capable of transmitting, in yeast, signals originating at mammalian G protein-coupled receptors, two general desiderata were recognized. First, the subunits should retain as much of the sequence of the native mammalian proteins as possible. Second, the level of expression for the heterologous components should approach, as closely as possible, the level of their endogenous counterparts. The results described by King, et al. (1990, Science 250:121-123) for expression of the human β2-adrenergic receptor and Gαs in yeast, taken together with negative results obtained by Kang, et al. (supra) with full-length mammalian Gα subunits other than Gαs, led us to the following preferences for the development of yeast strains in which mammalian G protein-coupled receptors could be linked to the pheromone response pathway.

1. Mammalian Gα subunits will be expressed using the native sequence of each subunit or, alternatively, as minimal gene fusions with sequences from the amino-terminus of GPA1 replacing the homologous residues from the mammalian Gα subunits.

2. Mammalian Gα subunits will be expressed from the GPA1 promoter either on low copy plasmids or after integration into the yeast genome as a single copy gene.

3. Endogenous Gβγ subunits will be provided by the yeast STE4 and STE18 loci.

E. Expression of Gα

Kang et al. supra reported that several classes of native mammalian G~subunits were able to interact functionally with yeast α subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not desirable for uses like those described in this application. Reconstruction of G protein-coupled receptor signal transduction in yeast requires the signaling component of the heterotrimeric complex (Gβγ) to be present stoichiometrically with Gα subunits. An excess of Gα subunits (as was required for coupling of mammalian Gαi2 and Gαo to yeast Gβγ in Kang et al.) would dampen the signal in systems where Gβγ subunits transduce the signal. An excess of Gα subunits raises the background level of signaling in the system to unacceptably high levels. Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpa1 genotype when expressed from the GPA1 promoter on low copy plasmids or from an integrated, single copy gene. In the work described in this application, all heterologous Gα subunits have been assayed in two biological systems. In the first assay heterologous Gα subunits are tested for an ability to functionally complement the growth arrest phenotype of gpa1 strains. In the second assay the transcription of a fus1-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

VII. Peptide Libraries

Yeast cells have been engineered to facilitate screening of exogenous drugs as receptor agonists and antagonists, although the cells did not themselves produce both the drugs and the receptors. Yeast cells engineered to produce the receptor, but not the drugs themselves, are inefficient because a sufficient concentration of each drug must be brought into contact with a number of cells in order to detect whether or not the drug has an action. Therefore, a microtiter plate well or test tube must be used for each drug, and the drug must be synthesized in advance and be sufficiently pure to judge its action on the yeast cells. When the yeast cell produces the drug, the effective concentration is higher.

Peptide libraries are systems which simultaneously display, in a form which permits interaction with a target, a highly diverse and numerous collection of peptides. These peptides may be presented in solution, or on beads, chips, bacteria, spores, plasmids or phage by methods known in the art. Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

U.S. Pat. No. 5,096,815, Ladner et al. describes a method of identifying novel proteins or polypeptides with a desired DNA binding activity in which semi-random ("variegated") DNA encoding a large number of different potential binding proteins is introduced, in expressible form, into suitable host cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA.

The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO 94/02502). The combinatorial peptide can be attached to one the termini of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3-100 amino acids in length, more preferably at least 5-50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library are semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007-16010; Griffths et al. (1993) *EMBO J* 12:725-734; Clackson et al. (1991) *Nature* 352:624-628; and Barbas et al. (1992) *PNAS* 89:4457-4461.

Accordingly, polypeptide(s) which are known ligands for a target receptor can be mutagenized by standard techniques to derive a variegated library of polypeptide sequences which can further be screened for agonists and/or antagonists. For example, the surrogate ligand Ser-Leu-Leu-Trp-Leu-Thr-Cys-Arg-Pro-Trp-Glu-Ala-Met (SEQ ID NO: 1) peptide, identified for FPRL-1, can be mutagenized to generate a library of peptides with some relationship to the original tridecapeptide. This library can be expressed in a reagent cell of the present invention, and other receptor activators can be isolated from the library. This may permit the identification of even more potent FPRL-1 surrogate ligands.

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter of course will identify potential antagonists of chemoattractant receptors. In still other embodiments, the surrogate ligand can be used to screen exogenous compound libraries (peptide and non-peptide) which, by modulating the activity of the identified surrogate, will presumably also similarly affect the native ligand's effect on the target receptor. In such embodiments, the surrogate ligand can be applied to the cells, though it is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In the present invention, the peptides of the library are encoded by a mixture of DNA molecules of different sequence. Each peptide-encoding DNA molecule is ligated with a vector DNA molecule and the resulting recombinant DNA molecule is introduced into a host cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

It is convenient to speak of the peptides of the library as being composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

VIII. Screening and Selection: Assays of Second Messenger Generation

When screening for bioactivity of peptides, intracellular second messenger generation can be measured directly. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{2+}$ transients, as well as stimulating cardiac $K^+$ channels.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When receptors that modulate cAMP are tested, it will be possible to use standard techniques for cAMP detection, such as competitive assays which quantitate [$^3$H]cAMP in the presence of unlabeled cAMP.

Certain receptors stimulate the activity of phospholipase C which stimulates the breakdown of phosphatidylinositol 4,5, bisphosphate to 1,4,5-IP3 (which mobilizes intracellular $Ca^{2+}$) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabeling techniques or HPLC.

The mobilization of intracellular calcium or the influx of calcium from outside the cell can be measured using standard techniques. The choice of the appropriate calcium indicator, fluorescent, bioluminescent, metallochromic, or $Ca^{2+}$-sensitive microelectrodes depends on the cell type and the magnitude and time constant of the event under study (Borle (1990) *Environ Health Perspect* 84:45-56). As an exemplary method of $Ca^{2+}$ detection, cells could be loaded with the $Ca^{2+}$ sensitive fluorescent dye fura-2 or indo-1, using standard methods, and any change in $Ca^{2+}$ measured using a fluorometer.

The other product of PIP2 breakdown, DAG can also be produced from phosphatidyl choline. The breakdown of this phospholipid in response to receptor-mediated signaling can also be measured using a variety of radiolabeling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons et al. (1984) *Proc. Natl. Acad. Sci. USA* 81:7426-7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

Modified methods for detecting receptor-mediated signal transduction exist and one of skill in the art will recognize suitable methods that may be used to substitute for the example methods listed.

IX. Screening and Selection Using Reporter Gene Constructs

In addition to measuring second messenger production, reporter gene constructs can be used. Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), *Nature* 282: 864-869) luciferase, and other enzyme detection systems, such as beta-galactosidase; firefly luciferase (deWet et al. (1987), *Mol. Cell. Biol.* 7:725-737); bacterial luciferase (Engebrecht and Silverman (1984), *Proc. Natl. Acad. Sci.* 1: 4154-4158; Baldwin et al. (1984), *Biochemistry* 23: 3663-3667); alkaline phosphatase (Toh et al. (1989) *Eur. J. Biochem.* 182: 231-238, Hall et al. (1983) *J. Mol. Appl. Gen.* 2: 101), human placental secreted alkaline phosphatase (Cullen and Malim (1992) *Methods in Enzymol.* 216:362-368).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) *Neuron* 4: 477-485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In the most preferred constructs, the transcriptional regulatory elements are derived from the c-fos gene.

The c-fos proto oncogene is the cellular homolog of the transforming gene of FBJ osteosarcoma virus. It encodes a nuclear protein that most likely involved in normal cellular growth and differentiation. Transcription of c-fos is transiently and rapidly activated by growth factors and by other inducers of other cell surface proteins, including hormones, differentiation-specific agents, stress, mitogens and other known inducers of cell surface proteins. Activation is protein synthesis independent. The c-fos regulatory elements include (see, Verma et al. (1987) *Cell* 51: a TATA box that is required for transcription initiation; two upstream elements for basal transcription, and an enhancer, which includes an element with dyad symmetry and which is required for induction by TPA, serum, EGF, and PMA.

The 20 bp transcriptional enhancer element located between −317 and −298 bp upstream from the c-fos mRNA cap site, which is essential for serum induction in serum starved NIH 3T3 cells. One of the two upstream elements is located at −63−−57 and it resembles the consensus sequence for cAMP regulation.

Other promoters and transcriptional control elements, in addition to those described above, include the vasoactive intestinal peptide (VIP) gene promoter (cAMP responsive; Fink et al. (1988), *Proc. Natl. Acad. Sci.* 85:6662-6666); the somatostatin gene promoter (cAMP responsive; Montminy et al. (1986), *Proc. Natl. Acad. Sci.* 8.3:6682-6686); the proenkephalin promoter (responsive to cAMP, nicotinic agonists, and phorbol esters; Comb et al. (1986), *Nature* 323:353-356); the phosphoenolpyruvate carboxy-kinase gene promoter (cAMP responsive; Short et al. (1986), *J. Biol. Chem.* 261:9721-9726); the NGFI-A gene promoter (responsive to NGF, cAMP, and serum; Changelian et al. (1989). *Proc. Natl. Acad. Sci.* 86:377-381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

However, when searching for peptides which can function as agonists of G protein-coupled receptors, or other pheromone system proteins, the growth arrest consequent to activation of the pheromone response pathway is an undesirable effect since cells that bind peptide agonists stop growing while surrounding cells that fail to bind peptides will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

It is, of course, desirable that the exogenous receptor be exposed on a continuing basis to the peptides. Unfortunately, this is likely to result in desensitization of the pheromone pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, (1993) *Mol. Cell. Biol.* 13:6876-6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1, bar1, ste2, ste3, pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

If the endogenous homolog of the receptor is produced by the yeast cell, the assay will not be able to distinguish between peptides which interact with the endogenous receptor and those which interact with the exogenous receptor. It is therefore desirable that the endogenous gene be deleted or otherwise rendered nonfunctional.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promoters known to be responsive to elevated cAMP levels. Upon binding of phosphorylated CREB to a CRE, transcription from this promoter is increased.

Phosphorylation of CREB is seen in response to both increased cAMP levels and increased intracellular $Ca^{2+}$ levels. Increased cAMP levels result in activation of PKA, which in turn phosphorylates CREB and leads to binding to CRE and transcriptional activation. Increased intracellular calcium levels results in activation of calcium/calmodulin responsive kinase IV (CaM kinase IV). Phosphorylation of CREB by CaM kinase IV is effectively the same as phosphorylation of CREB by PKA, and results in transcriptional activation of CRE containing promoters.

Therefore, a transcriptional-based readout can be constructed in cells containing a reporter gene whose expression is driven by a basal promoter containing one or more CRE. Changes in the intracellular concentration of $Ca^{2+}$ (a result of alterations in the activity of the receptor upon engagement with a ligand) will result in changes in the level of expression of the reporter gene if: a) CREB is also co-expressed in the cell, and b) either the endogenous yeast CaM kinase will phosphorylate CREB in response to increases in calcium or if an exogenously expressed CaM kinase IV is present in the same cell. In other words, stimulation of PLC activity will result in phosphorylation of CREB and increased transcription from the CRE-construct, while inhibition of PLC activity will result in decreased transcription from the CRE-responsive construct.

As described in Bonni et al. (1993) *Science* 262:1575-1579, the observation that CNTF treatment of SK-N-MC cells leads to the enhanced interaction of STAT/p91 and STAT related proteins with specific DNA sequences suggested that these proteins might be key regulators of changes in gene expression that are triggered by CNTF. Consistent with this possibility is the finding that DNA sequence elements similar to the consensus DNA sequence required for STAT/p91 binding are present upstream of a number of genes previously found to be induced by CNTF (e.g., Human c-fos, Mouse c-fos, Mouse tis11, Rat junB, Rat SOD-1, and CNTF). Those authors demonstrated the ability of STAT/p91 binding sites to confer CNTF responsiveness to a non-responsive reporter gene. Accordingly, a reporter construct for use in the present invention for detecting signal transduction through STAT proteins, such as from cytokine receptors, can be generated by using −71 to +109 of the mouse c-fos gene fused to the bacterial chloramphenicol acetyltransferase gene (−71fosCAT) or other detectable marker gene. Induction by a cytokine receptor induces the tyrosine phosphorylation of STAT and STAT-related proteins, with subsequent translocation and binding of these proteins to the STAT-RE. This then leads to activation of transcription of genes containing this DNA element within their promoters.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not. Selection is preferable to screening in that it can provide a means for amplifying from the cell culture those cells which express a test polypeptide which is a receptor effector.

The marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, suitable positively selectable (beneficial) genes include the following: LACZ, URA3, LYS2, HIS3, LEU2, TRP1, ADE1, ADE2, ADE3, ADE4, ADE5, ADE7, ADE8, ARG1, ARG3, ARG4, ARG5, ARG6, ARG8, HIS1, HIS4, HIS5 ILV1, ILV2, ILV5, THR1, THR4, TRP2, TRP3, TRP4, TRP5, LEU1, LEU4, MET2, MET3, MET4, MET8, MET9, MET14, MET16, MET19, URA1, URA2, URA4, URA5, URA10, H0M3, H0M6, ASP3, CHO1, ARO 2, ARO7, CYS3, OLE1, IN01, IN02, IN04, PR01, and PR03.

Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanine), and other recessive drug-resistant markers.

In one example, the marker gene effects yeast cell growth. The natural response to signal transduction via the yeast pheromone system response pathway is for cells to undergo growth arrest. This is the preferred way to select for antagonists to a ligand/receptor pair that induces the pathway. An autocrine peptide antagonist would inhibit the activation of the pathway; hence, the cell would be able to grow. Thus, the FAR1 gene may be considered an endogenous counterselectable marker. The FAR1 gene is preferably inactivated when screening for agonist activity.

The marker gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

X. Genetic Markers in Yeast Strains

Yeast strains that are auxotrophic for histidine (HIS3) are known, see Struhl and Hill, (1987) *Mol. Cell. Biol.*, 7:104; Fasullo and Davis, *Mol. Cell. Biol.,* (1988) 8:4370. The HIS3 (imidazoleglycerol phosphate dehydratase) gene has been used as a selective marker in yeast. See Sikorski and Heiter, (1989) *Genetics,* 122:19; Struhl, et al., *Proc. Natl. Acad. Sci.* (1979) 76:1035; and, for FUS1-HIS3 fusions, see Stevenson, et al., (1992) *Genes Dev.,* 6:1293.

XI. Novel FPRL-1 Ligands

Figure 6:
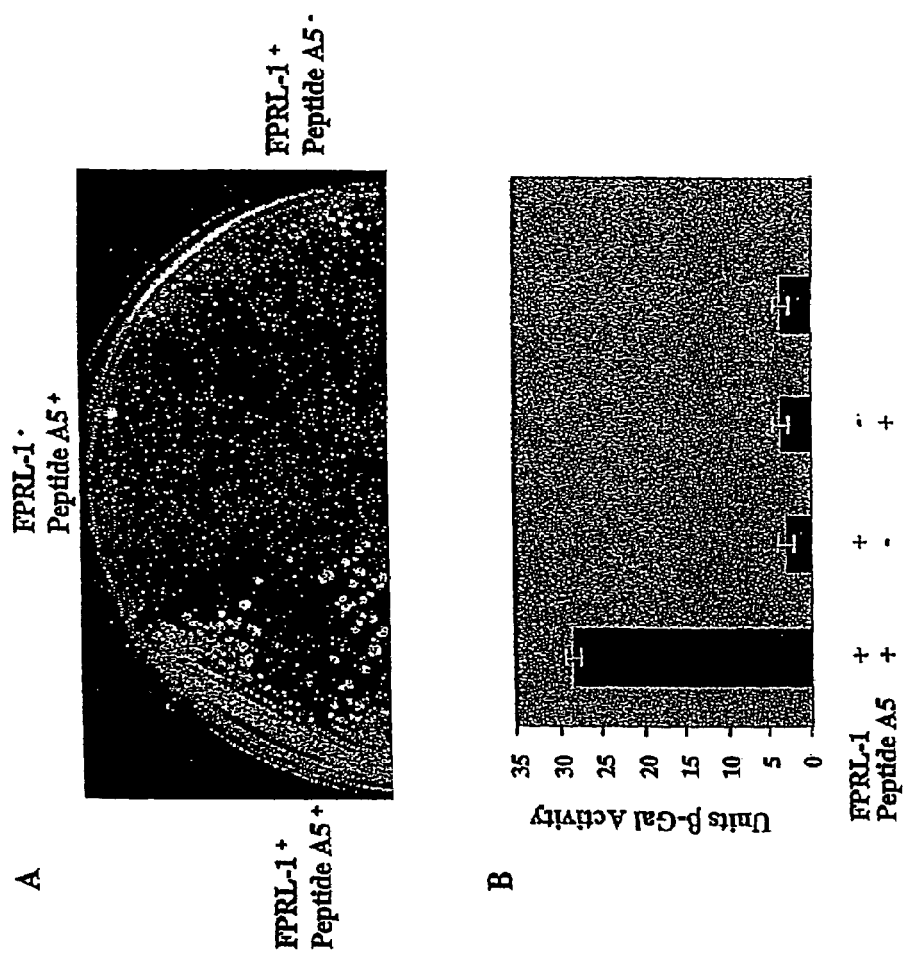
FIG. 6a is a photograph showing strain CY1141 expressing both FPRL-1 and the A5 peptide. The A5 peptide alone or the receptor alone were streaked on LUH-AT plates. Growth signifies activation of the pheromone signaling pathway.
FIG. 6b is a graph depicting levels of β-galactosidase activity from yeast strains containing a pheromone-responsive FUSI-lacZ gene. Yeast strains that express either FPRL-1 or peptide A5 alone, exhibit a low β-galactosidase activity. In contrast, yeast cells that express both FPRL-1 and peptide A5, exhibit a 7-fold induction of β-galactosidase activity compared to control strains

Yet another aspect of the invention pertains to identification of novel ligands for the orphan receptor, FPRL-1. As described in Example 6, a tridecapeptide having the sequence Ser-Leu-Leu-Trp-Leu-Thr-Cys-Arg-Pro-Trp-Glu-Ala-Met (SEQ ID NO: 1) was identified from a polypeptide library on the basis of its ability to act as a surrogate ligand for FPRL-1. Five additional peptides were also identified as surrogate ligands for FPRL-1, from random peptide libraries, as described in Example 7. The identification of peptides as FPRL-1 ligands was based on the evidence that growth of the autocrine strain CY6571 (which carries the FUS1-HIS3 gene) in the absence of histidine depends on the expression of both the FPRL-1 receptor and the peptide (see Examples 6 and 7 and FIG. 6a). Furthermore, transformation of the CY6565 yeast strain (which carries the FUSI-lacz fusion gene and a plasmid carrying the FPRL-1 receptor) with a plasmid encoding the peptide, resulted in activation of the pheromone pathway, determined by induction of β-galactosidase synthesis. Levels of β-galactosidase were higher in transformants carrying both the FPRL-1- and the peptide-expressing plasmids compared with transformants carrying either plasmid alone (FIG. 6b).

To clarify further that the six identified peptides were agonists of FPRL-1, chemically synthesized peptides corresponding to the identified peptide agonists were added exogenously to the CY6565 strain. Peptides were synthesized using standard peptide synthesis techniques. The synthetic peptides produced a dose-dependent induction of β-galactosidase activity, thereby confirming that the peptides identified by the autocrine procedure are authentic agonists for FPRL-1 (see Example 7).

Figure 7:
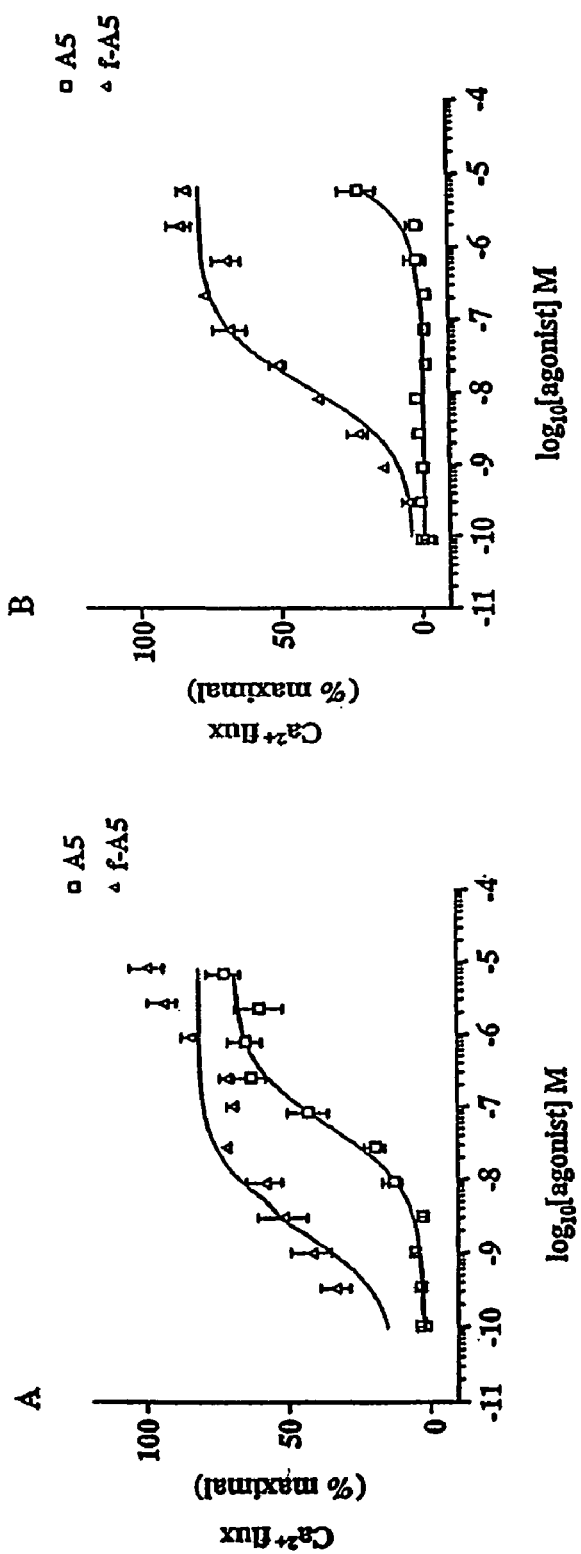
FIG. 7a is a graph depicting changes in intracellular $Ca^{2+}$ in HEK293/Gal6 cells stably expressing FPRL-1 upon exposure to increasing concentrations of peptides A5 and formylated A5 (f-A5). Flux is expressed as the percent of the maximal change in $Ca^{2+}$ concentration attained with each peptide.
FIG. 7b is a graph depicting changes in intracellular $Ca^{2+}$ in HEK293/Gal6 cells stably expressing FPR1 upon exposure to increasing concentrations of peptides A5 and formylated A5 (f-A5). Flux is expressed as the percent of the maximal change in $Ca^{2+}$ concentration attained with each peptide.

To test the specificity of responses of the peptides, human cell lines stably expressing either FPR1 or FPRL-1 were established from HEK293 clones expressing human α 16. Activity was determined by measuring transient $Ca^{2+}$ flux in cells as a function of peptide concentration. Addition of synthetic peptides A5 and fA5 (see Table 1 below) to cells expressing FPRL-1 yielded a dose-dependent activation of calcium mobilization with $EC_{50}$ values ranging from $2 \times 10^{-9}$ M to $2.4 \times 10^{-6}$ M (FIG. 7a). In contrast, significantly higher concentration of peptides A5 and fA5 were required to induce calcium mobilization in cells expressing FPR1. Preferred peptide agonists for FPRL-1 comprise the sequences A5, Ser-Leu-Leu-Trp-Leu-Thr-Cys-Arg-Pro-Trp-Glu-Ala-Met (SEQ ID NO: 1) MMk-1, Leu-Glu-Ser-Ile-Phe-Arg-Ser-Leu-Leu-Phe-Arg-Val-Met (SEQ ID NO: 2); AF-1, Cys- Pro-Ala-Ala-Val-Leu-Trp-Arg-Trp-Val-Pro-Met (SEQ ID NO: 3); AF-2, Ser-Met-Cys-Pro-Thr-Ala-Ser-Ala-Trp-Val-Trp-Leu-Met (SEQ ID NO: 4); AF-3, Arg-Phe-Pro-Lys-Asn-Cys-His-Leu-Arg-Pro-Pro-Arg-Met-Ile-Leu-Phe-Thr-Ala-Leu-Val (SEQ ID NO: 5); and DM-1, Pro-Pro-Phe-Phe-Phe-Arg-Pro-Val-Gly-Met-Phe (SEQ ID NO: 6).

Preferably, the peptides of the present invention include all or a portion of the FPRL-1 agonist peptides, or a homologs thereof. The peptide (or peptidomimetic) is preferably at least 3 amino acid residues in length, though peptides of up to 80 amino acids, such as 4, 5, 7, 10, 11, 12, 13, 20, 30, 40, 50, 60, 70, 80 or more residues in length, are preferred. Preferably the peptides are 3-40 residues in length. Peptides may be part of longer peptides or proteins. Peptides may also be provided as fusion proteins, with fusion either at the N terminal of the peptide, the C-terminal of the peptide, or at both the N- and C-termini. Longer naturally occurring polypeptides are also within the scope of the invention, for example, IL-8, a 72 amino acid polypeptide that interacts with the heterologous receptor. Longer peptides which include the FPRL ligand are also contemplated. For example, the sequence derived from the FPRL-1 surrogate ligand can be provided as part of a fusion protein. The minimum peptide length is chiefly dictated by the need to obtain sufficient potency as an activator or inhibitor. Given the size of the peptide isolated in subject assay, smaller fragments of the tridecapeptide which retain receptor binding activity will be easily identified, e.g., by chemical synthesis of different fragments. The maximum peptide length will only be a function of synthetic convenience once an active peptide is identified.

The invention also provides for the generation of mimetics, e.g., peptide or non-peptide agents. Moreover, the present invention also contemplates variants of the subject polypeptides which may themselves be either agonistic or antagonistic of, for example, the Ser-Leu-Leu-Trp-Leu-Thr-Cys-Arg-Pro-Trp-Glu-Ala-Met (SEQ ID NO: 1) peptide. Thus, using mutagenic techniques known in the art, the determinants of Ser-Leu-Leu-Trp-Leu-Thr-Cys-Arg-Pro-Trp-Glu-Ala-Met (SEQ ID NO: 1) polypeptide which participate in FPRL-1 interactions can be elucidated. To illustrate, the critical residues of a subject polypeptide which are involved in molecular recognition of an FPRL-1 receptor can be determined and used to generate variant polypeptides which competitively inhibit binding of the authentic Ser-Leu-Leu-Trp-Leu-Thr-Cys-Arg-Pro-Trp-Glu-Ala-Met (SEQ ID NO: 1) peptide with that receptor. By employing, for example, scanning mutagenesis to map the amino acid residues of the polypeptide involved in binding the FPRL-1 receptor, peptide and peptidomimetic compounds can be generated which mimic those residues in binding to the receptor and which consequently can inhibit binding of an authentic ligand for the FPRL-1 receptor and interfere with the function of that receptor.

Moreover, as is apparent from the present and parent disclosures, mimetopes of the subject polypeptide, for example, Ser-Leu-Leu-Trp-Leu-Thr-Cys-Arg-Pro-Trp-Glu-Ala-Met (SEQ ID NO: 1) peptide can be provided as non-hydrolyzable peptide analogs. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: *Chemistry and Biology*, G. R. Marshall ed., ESCOM Publisher: Leiden, Netherlands, 1988, p. 105), keto-methylene pseudopeptides (Ewenson et al. (1986) *J. Med. Chem.* 29:295; and Ewenson et al. in Peptides: *Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J. Chem. Soc. Perkin. Trans.* 1:1231), β-aminoalcohols (Gordon et al. (1985) *Biochem. Biophys. Res. Commun.* 126:419; and Dann et al. (1986) *Biochem. Biophys. Res. Commun.* 134:71), diaminoketones (Natarajan et al. (1984) *Biochem. Biophys. Res. Commun.* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988)

In an exemplary embodiment, the peptidomimetic can be derived as a retro-inverso analog of the peptide. To illustrate, the Ser-Leu-Leu-Trp-Leu-Thr-Cys-Arg-Pro-Trp-Glu-Ala-Met (SEQ ID NO: 1) peptide can be generated as the retro-inverso analog:

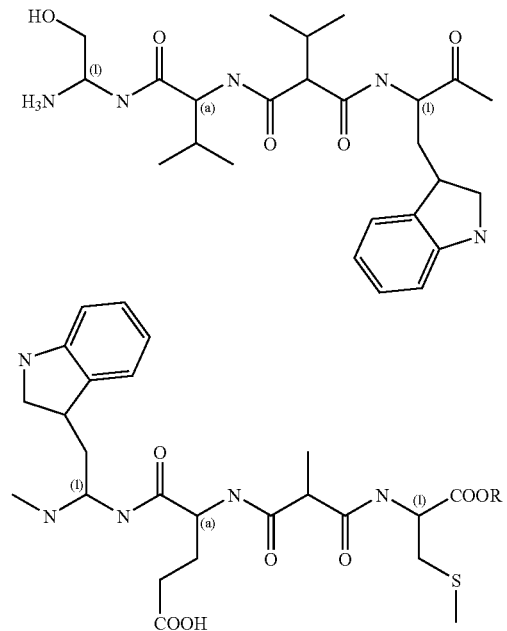

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the serine analog is synthesized by treating a protected serine with ammonia under HOBT-DCC coupling conditions to yield the N-Boc amide, and then effecting a Hofmann-type rearrangement with I,I-bis-(trifluoroacetoxy) iodobenzene (TIB), as described in Radhakrishna et al. (1979) *J. Org. Chem.* 44:1746. The product amine salt is then coupled to a side-chain protected (e.g., as the benzyl ester) N-Fmoc D-Leu residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S.

Pat. No. 5,061,811 to Pinori et al., to yield the retro-inverso tripeptide analog S-L-L. The pseudotripeptide is then coupled with L-Trp under standard conditions to give the protected tetrapeptide analog. The protecting groups are removed to release the product, and the steps repeated to elongate the tetrapeptide to the full length peptide. It will be understood that a mixed peptide, e.g. including some normal peptide linkages, can be generated. As a general guide, sites which are most susceptible to proteolysis are typically altered, with less susceptible amide linkages being optional for mimetic switching The final product, or intermediates thereof, can be purified by HPLC.

In another illustrative embodiment, the peptidomimetic can be derived as a retro-enatio analog of the peptide, such as the exemplary retro-enatio peptide analog derived for the illustrative Ser-Leu-Leu-Trp-Leu-Thr-Cys-Arg-Pro-Trp-Glu-Ala-Met (SEQ ID NO: 1) peptide:

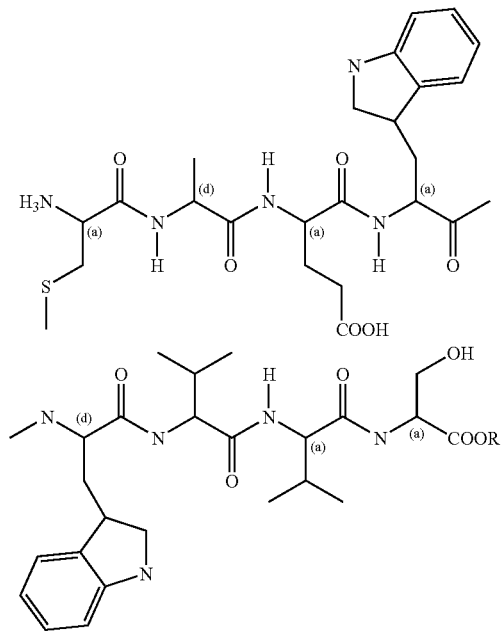

NH$_3$-(d) Met-(d) Ala-(d) Glu-(d)Trp . . . (d) Trp-(d) Leu-(d)-Leu-(d) Ser

Retro-enantio analogs such as this can be synthesized using commercially available D-amino acids and standard solid- or solution-phase peptide-synthesis techniques. For example, in a preferred solid-phase synthesis method, a suitably amino-protected (t-butyloxycarbonyl, Boc) D-Serine residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (D-Leu) is introduced by coupling with diisopropylcarbodiimide. The resin is again washed, and the cycle repeated for each of the remaining amino acids in turn (D-Leu, D-Trp, etc.). When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for the subject polypeptide. For example, an exemplary olefin analog is derived for the illustrative Ser-Leu-Leu-Trp-Leu-Thr-Cys-Arg-Pro-Trp-Glu-Ala-Met (SEQ ID NO: 1) peptide:

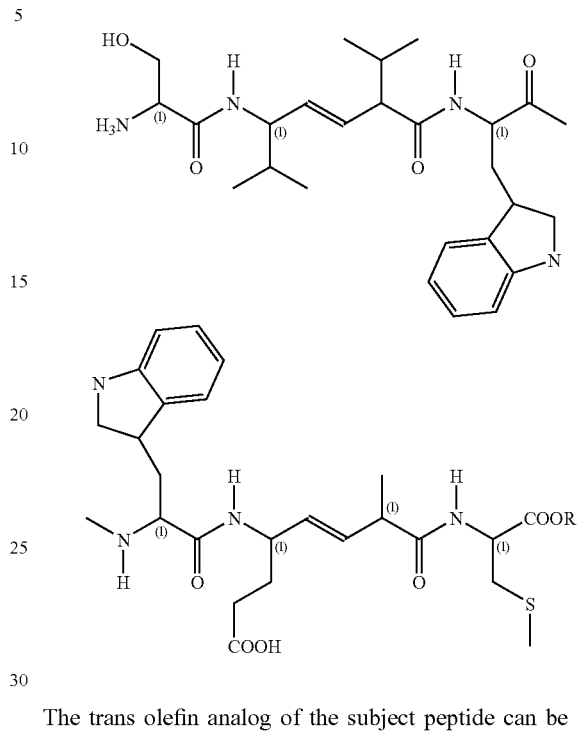

The trans olefin analog of the subject peptide can be synthesized according to the method of Y. K. Shue et al. (1987) Tetrahedron Letters 28:3225.

Still another class of peptidomimetic derivatives include the phosphonate derivatives, such as the partially phosphonate derivatived Ser-Leu-Leu-Trp-Leu-Thr-Cys-Arg-Pro-Trp-Glu-Ala-Met (SEQ ID NO: 1) peptide:

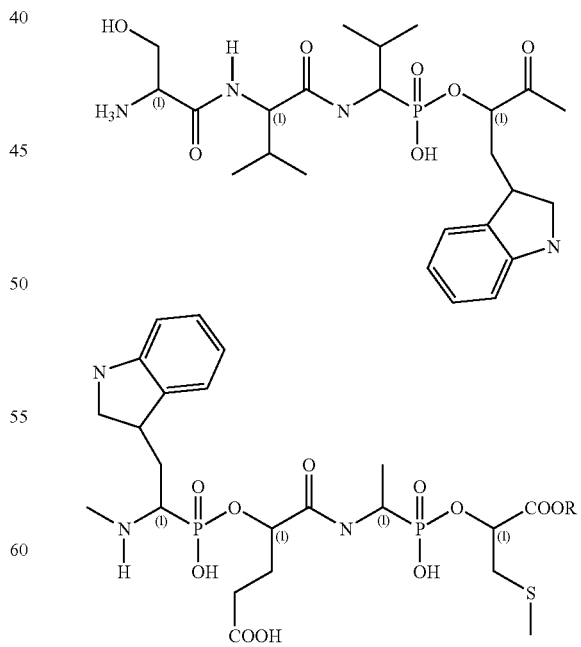

The synthesis of such phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

XII. Further Manipulation of Peptide Ligands

The above examples provide guidance for a variety of techniques for manipulating peptide ligands identified in the present screening assay in order to develop more specific and/or potent agonists or antagonists. In addition, a variety of combinatorial techniques are known in the art and will be useful for further optimization of the peptide leads coming off the instant assay. For example, alanine scanning mutagenesis and the like (Lowman et al. (1991) *Biochemistry* 30:10832-10838; and Cunningham et al. (1989) *Science* 244:1081-1085), by linker scanning mutagenesis (Brown et al. (1992) *Mol. Cell Biol.* 12:2644-2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11-19); or by random mutagenesis (Miller et al. (1992) *A Short Course in Bacterial Genetics*, CSHL Press, Cold Spring Harbor, N.Y.) can be used to create libraries of variants which can be further screened, even by simple receptor binding assays, for receptor binding activity. To further illustrate the state of the art, it is noted that the review article of Gallop et al. (1994) *J Med Chem* 37:1233 describe the general state of the art of combinatorial libraries. In particular, Gallop et al. state at page 1239 "[s]creening the analog libraries aids in determining the minimum size of the active sequence and in identifying those residues critical for binding and intolerant of substitution".

For the most part, the amino acids used in the subject receptor agonists and antagonists of this invention will be those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

However, the term amino acid residue further includes analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptidomimetic can include an amino acid analog as for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Also included are the D and L stereoisomers of such amino acids when the structure of the amino acid admits of stereoisomeric forms. The configuration of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis. For the purposes of this application, unless expressly noted to the contrary, a named amino acid shall be construed to include both the D or L stereoisomers, preferably the L stereo isomer.

XIII. Pharmaceutical Compositions of Identified Compounds

In another aspect, the invention features pharmaceutical compositions of the identified surrogate ligands, or receptor antagonists. The practitioner of a subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

All patents, published patent applications and other references disclosed herein are hereby expressly incorporated herein by reference.

EXEMPLIFICATION

The invention now being generally described will be more readily understood by reference to the following examples, which are included merely for purposes of illustration of certain aspects and embodiments of the present invention and are not intended to limit the invention.

Example 1

Development of Autocrine Yeast Strains

This example describes a pilot experiment in which haploid cells were engineered to be responsive to their own pheromones. (Note that in the examples, functional genes are capitalized and inactivated genes are in lower case.) For this purpose, recombinant DNA molecules designed, and constructed, to:

i. place the coding region of STE2 under the transcriptional control of elements which normally direct the transcription of STE3. This is done in a plasmid that allows the replacement of genomic STE3 of *S. cerevisiae* with sequences wherein the coding sequence of STE2 is driven by STE3 transcriptional control elements; and ii. place the coding region of STE3 under the transcriptional control of elements which normally direct the transcription of STE2. This is done in a plasmid which will allow the replacement of genomic STE2 of *S. cerevisiae* with sequences wherein the coding sequence of STE3 is driven by STE2 transcriptional control elements.

The sequence of the STE2 gene is known see Burkholder A. C. and Hartwell L. H. (1985), *Nuc. Acids Res.* 13, 8463; Nakayama N., Miyajima A., Arai K. (1985) *EMBO J.* 4, 2643.

A 4.3 kb BamHI fragment that contains the entire STE2 gene was excised from plasmid YEp24-STE2 (obtained from J. Thorner, Univ. of California) and cloned into pAL-TER (Protocols and Applications Guide, 1991, Promega Corporation, Madison, Wis.). An SpeI site was introduced 7 nucleotides (nts) upstream of the ATG of STE2 with the following mutagenic oligonucleotide, using the STE2 minus strand as template:5'-GTTAAGAACCATATACTAGTAT-CAAAAATGTCTG 3'(SEQ ID NO: 9)

A second SpeI site was simultaneously introduced just downstream of the STE2 stop codon with the following mutagenic oligonucleotide: 5'-TGATCAAAATTTAC-TAGTTTGAAAAAGTAATTTCG 3' (SEQ ID NO: 10)

The BamHI fragment of the resulting plasmid (Cadus 1096) containing STE2 with SpeI sites immediately flanking the coding region, was then subcloned into the yeast integrating vector YIp19 to yield Cadus 1143.

The STE3 sequence is also known (Nakayama N., Miyajima A., Arai K. (1985), *EMBO J.* 4, 2643; (Hagen et al. (1986), *Proc. Natl. Acad. Sci.* 83, 1418. STE3 was made available by Dr. J. Broach as a 3.1 kb fragment cloned into pBLUESCRIPT-KS II (Stratagene, 11011 North Torrey Pines Road, La Jolla, Calif. 92037). STE3 was subcloned as a KpnI-XbaI fragment into both M13mp18 RF (to yield Cadus 1105 and pUC19 (to yield Cadus 1107). The two SpeI sites in Cadus 1107 were removed by digestion with SpeI, fill-in with DNA polymerase I Klenow fragment, and recircularization by blunt-end ligation. Single-stranded DNA containing the minus strand of STE3 was obtained using Cadus 1105 and SpeI sites were introduced 9 nts upstream of the start codon and 3 nts downstream of the stop codon of STE3 with the following mutagenic oligonucleotides, respectively:
5'-GGCAAAATACTAGTAAAATTTTCATGTC-3' (SEQ ID NO: 11)
5'-GGCCCTTAACACACTAGTGTCGCATTATATTTAC-3'(SEQ ID NO: 12)

The mutagenesis was accomplished using the T7-GEN protocol of United States Biochemical (T7-GEN In Vitro Mutagenesis Kit, Descriptions and Protocols, 1991, United States Biochemical, P.O. Box 22400, Cleveland, Ohio 44122). The replicative form of the resulting Cadus 1141 was digested with AflII and KpnI, and the approximately 2 kb fragment containing the entire coding region of STE3 flanked by the two newly introduced Spe I sites was isolated and ligated with the approximately 3.7 kb vector fragment of AflII- and KpnI-digested Cadus 1107, to yield Cadus 1138. Cadus 1138 was then digested with XbaI and KpnI, and the STE3-containing 2.8 kb fragment was ligated into the XbaI- and KpnI-digested yeast integrating plasmid pRS406 (Sikorski, et al. (1989), *Genetics* 122:19-27) to yield Cadus 1145.

The SpeI fragment of Cadus 1143 was replaced with the SpeI fragment of Cadus 1145 to yield Cadus 1147, in which the coding sequences of STE3 are under the control of STE2 expression elements. Similarly, the SpeI fragment of Cadus 1145 was replaced with the SpeI fragment of Cadus 1143 to yield Cadus 1148, in which the coding sequences of STE2 are under the control of STE3 expression elements. Using the method of pop-in/pop-out replacement (Rothstein, (1991) *Methods in Enzymology*, 194:281 301), Cadus 1147 was used to replace genomic STE2 with the ste2-STE3 hybrid in a MATa cell and Cadus 1148 was used to-replace genomic STE3 with the ste3-STE2 hybrid in a MATα cell. Cadus 1147 and 1148 contain the selectable marker URA3.

Haploid yeast of mating type a which had been engineered to express HIS3 under the control of the pheromone-inducible FUS1 promoter were transformed with CADUS 1147, and transformants expressing URA3 were selected. These transformants, which express both Ste2p and Ste3p, were plated on 5-fluoroorotic acid to allow the selection of clones which had lost the endogenous STE2, leaving in its place the heterologous, integrated STE3. Such cells exhibited the ability to grow on media deficient in histidine, indicating autocrine stimulation of the pheromone response pathway.

Similarly, haploids of mating type α that can express HIS3 under the control of the pheromone-inducible FUS1 promoter were transformed with CADUS 1148 and selected for replacement of their endogenous STE3 with the integrated STE2. Such cells showed, by their ability to grow on histidine-deficient media, autocrine stimulation of the pheromone response pathway.

Example 2

Strain Development

In this example, yeast strains are constructed which will facilitate selection of clones which exhibit autocrine activation of the pheromone response pathway. To construct appropriate yeast strains, we will use: The YIp-STE3 and pRS-STE2 knockout plasmids described above, plasmids available for the knockout of FAR1, SST2, and HIS3, and mutant strains that are commonly available in the research community. The following haploid strains will be constructed, using one-step or two-step knockout protocols described in *Meth. Enzymol* 194:281-301, 1991:

| | | | | | | | |
|---|---|---|---|---|---|---|---|
| 1. | MATα | ste3::STE2::ste3 | | far1 | sst2 | FUS1::HIS3 | |
| 2. | MATα | ste2::STE3::ste2 | | far1 | sst2 | FUS1::HIS3 | |
| 3. | MATα | ste3::STE2::ste3 | | far1 | sst2 | mfα1 mfα2 | FUS1::HIS3 |
| 4. | MATa | ste2::STE3::ste2 | | far1 | sst2 | mfa1 mfa2 | FUS1::HIS3 |
| 5. | MATa | bar1 | far1-1 | fus1-HIS3 | ste14::TRP1 | ura3 trp1 | leu2 his3 |
| 6. | MATa | mfa1 mfa2 | far1-1 | his3::fus1-HIS3 | ste2-STE3 | ura3 met1 | ade1 leu2 |

Strains 1 and 2 will be tested for their ability to grow on histidine-deficient media as a result of autocrine stimulation of their pheromone response pathways by the pheromones which they secrete. If these tests prove successful, strain 1 will be modified to inactivate endogenous MFα1 and MFα2. The resulting strain 3, MATα far1 sst2 ste3::STE2::ste3 FUS1::HIS3 mfa1 mfa2, should no longer display the selectable phenotype (i.e., the strain should be auxotrophic for histidine). Similarly, strain 2 will be modified to inactivate endogenous MFa1 and MFa2. The resulting strain 4, MATa far1 sst2 ste2::STE3::ste2 FUS1::HIS3 mfa1 mfa2, should be auxotrophic for histidine. The uses of strains 5 and 6 are outlined in Examples 3 and 4 below.

Example 3

Peptide Library

In this example, a synthetic oligonucleotide encoding a peptide is expressed so that the peptide is secreted or transported into the periplasm.

i. The region of MFα1 which encodes mature α-factor has been replaced via single-stranded mutagenesis with restriction sites that can accept oligonucleotides with AflII and BglII ends. Insertion of oligonucleotides with AflII and BglII ends will yield plasmids which encode proteins containing the MFα1 signal and leader sequences upstream of the sequence encoded by the oligonucleotides. The MFα1 signal and leader sequences should direct the processing of these precursor proteins through the pathway normally used for the transport of mature α-factor.

The MFα1 gene, obtained as a 1.8 kb EcoRI fragment from pDA6300 (J. Thorner, Univ. of California) was cloned into pALTER in preparation for oligonucleotide-directed mutagenesis to remove the coding region of mature α-factor while constructing sites for acceptance of oligonucleotides with AflII and BclI ends. The mutagenesis was accomplished using the minus strand as template and the following mutagenic oligonucleotide:
5'-CTAAAGAAGAAGGGGTATCTTTGCT-
TAAGCTCGAGATCTCGACTGATA- ACAACAGTG-
TAG-3' (SEQ ID NO: 13)

A HindIII site was simultaneously introduced 7 nts upstream of the MFα1 start codon with the oligonucleotide:
5'-CATACACAATATAAAGCTTTAAAAGAATGAG-3'
(SEQ ID NO: 14)

The resulting plasmid, Cadus 1214, contains a HindIII site 7 nts upstream of the MFα1 initiation codon, an AflII site at the positions which encode the KEX2 processing site in the MFα1 leader peptide, and XhoI and BglII sites in place of all sequences from the leader-encoding sequences up to and including the normal stop codon. The 1.5 kb HindIII fragment of Cadus 1214 therefore provides a cloning site for oligonucleotides to be expressed in yeast and secreted through the pathway normally traveled by endogenous α-factor.

Figure 2:
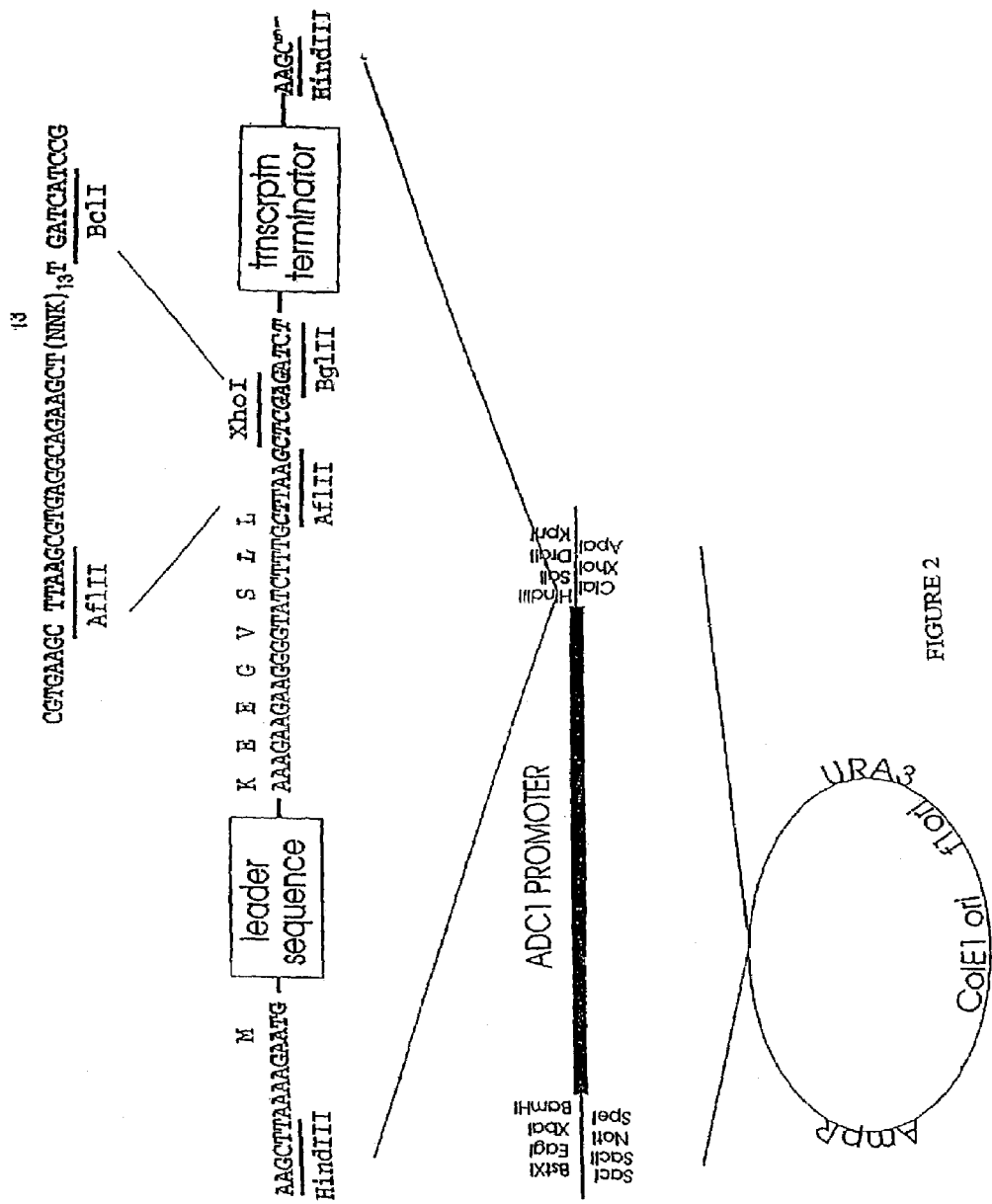
FIG. 2 is a schematic diagram of the structure of the plasmid resulting from insertion of random oligonucleotides into pADC-MF alpha. This plasmid expresses random peptides in the context of the MF alpha 1 signal and leader peptide.

A sequence comprising the ADC1 promoter and 5' flanking sequence was obtained as a 1.5 kb BamHI-HindIII fragment from pAAH5 (Ammerer, G. (1983) Academic Press, Inc., Meth. Enzymol. 101, 192-201 and ligated into the high copy yeast plasmid pRS426 (Christianson, et al. (1992) Gene 110:119-122) (see FIG. 1). The unique XhoI site in the resulting plasmid was eliminated to yield Cadus 1186. The 1.5 Kb HindIII fragment of Cadus 1214 was inserted into HindIII-digested Cadus 1186; expression of sequences cloned into this cassette initiates from the ADHI promoter. The resulting plasmid, designated Cadus 1215, can be prepared to accept oligonucleotides with AflII and BclI ends by digestion with those restriction endonucleases. The oligonucleotides will be expressed in the context of MFα1 signal and leader peptides (FIG. 2).

Modified versions of Cadus 1215 were also constructed. To improve the efficiency of ligation of oligonucleotides into the expression vector, Cadus 1215 was restricted with KpnI and relegated to yield Cadus 1337. This resulted in removal of one of two HindIII sites. Cadus 1337 was linearized with HindIII, filled-in, and recircularized to generate Cadus 1338. To further tailor the vector for library construction, the following double-stranded oligonucleotide was cloned into AflII- and BglII-digested Cadus 1338:
5'-TTAAGCGTGAGGCAGAAGCTTATCGATA-3' (SEQ ID NO: 15) oligo 062
3'-CGCACTCCGTCTTCGAATAGCTATCTAG-5' (SEQ ID NO: 16) oligo 063

The ClaI site is unique in the resulting vector, Cadus 1373. In Cadus 1373, the HindIII site that exists at the junction between the MFα pro sequence and the mature peptide to be expressed by this vector was made unique. Therefore the HindIII site and the downstream BglII site can be used to insert oligo-nucleotides encoding peptides of interest. These modifications of Cadus 1215 provide an alternative to the use of the AflII site in the cloning of oligonucleotides into the expressions vector.

Cadus 1373 was altered further to permit elimination from restricted vector preparations of contaminating singly-cut plasmid. Such contamination could result in unacceptably high background transformation. To eliminate this possibility, approximately 1.1 kb of dispensable ADH1 sequence at the 5' side of the promoter region was deleted. This was accomplished by restriction of Cadus 1373 with SphI and BamHI, fill-in, and ligation; this maneuver regenerates the BamHI site. The resulting vector, Cadus 1624, was then restricted with HindIII and ClaI and an approximately 1.4 kb HindIII and ClaI fragment encoding 25 lacZ was inserted to generate Cadus 1625. Use of HindIII- and BglII-restricted Cadus 1625 for acceptance of oligonucleotides results in a low background upon transformation of the ligation product into bacteria.

Two single-stranded oligonucleotide sequences (see below) are synthesized, annealed, and repetitively filled in, denatured, and reannealed to form double-stranded oligonucleotides that, when digested with AflII and BclI, can be ligated into the polylinker of the expression vector, Cadus 1215. The two single-stranded oligonucleotides have the following sequences:
5'-GCTACTTAAGCGTGAGGCAGAAGCT-3' (SEQ ID NO: 17) and
5'-CGGATGATCA(NNN)$_n$AGCTTCTGCCTCACGCT-TAAG TAGC-3' (SEQ ID NO: 18)

where N is any chosen nucleotide and n is any chosen integer. Yeast transformed with the resulting plasmids will secrete—through the α-factor secretory pathway—peptides whose amino acid sequence is determined by the particular choice of N and n). Alternatively, the following single stranded oligonucleotides are used:

MFαNNK (76 mer):
5'-CTGGATGCGAAGACAGCTNNKNNKNN-KNNKNNKNNKNNKNNKNNKNNKNNK NKNNK TGATCAGTCTGTGACGC-3' (SEQ ID NO: 19)

and MFαMbo (17 mer):
5'-GCGTCACAGACTGATCA-3' (SEQ ID NO: 20)

When annealed the double stranded region is:
TG*AT*CAGTCTGTGACGC (SEQ ID NO: 21)
AC*TA*GTCAGACACTGCG (SEQ ID NO: 22)

After fill-in using Taq DNA polymerase (Promega Corporation, Madison, Wis.), the double stranded product is restricted with BbsI and MboI and ligated to HindIII- and BglII-restricted Cadus 1373.

ii. The region of MFa1 which encodes mature a-factor will be replaced via single stranded mutagenesis with restriction sites that can accept oligonucleotides with XhoI and AflII ends. Insertion of oligonucleotides with XhoI and AflII ends will yield plasmids which encode proteins containing the MFa1 leader sequences upstream of the sequence encoded by the oligonucleotides. The MFa1 leader sequences should direct the processing of these precursor proteins through the pathway normally used for the transport of mature a-factor.

MFA1, obtained as a BamHI fragment from pKK1 (provided by J. 30 Thorner and K. Kuchler), was ligated into the BamHI site of pALTER (Promega). Using the minus strand of MFA1 as template, a HindIII site was inserted by oligonucleotide-directed mutagenesis just 5' to the MFA1 start codon using the following oligonucleotide:
5'-CCAAAATAAGTACAAAGCTTTCGAATA-GAAATGCAACCATC-3' (SEQ ID NO: 23)

A second oligonucleotide was used simultaneously to introduce a short polylinker for later cloning of synthetic oligonucleotides in place of MFA1 sequences. These MFA1 sequences encode the C-terminal 5 amino acids of the 21 amino acid leader peptide through to the stop codon:
5'GCCGCTGGAAAAGAAAAGACCTC-GAGCTCGCTTAAGTTCTGCGTACAAAA ACG-TTGTTC-3' (SEQ ID NO: 24)

Figure 3:
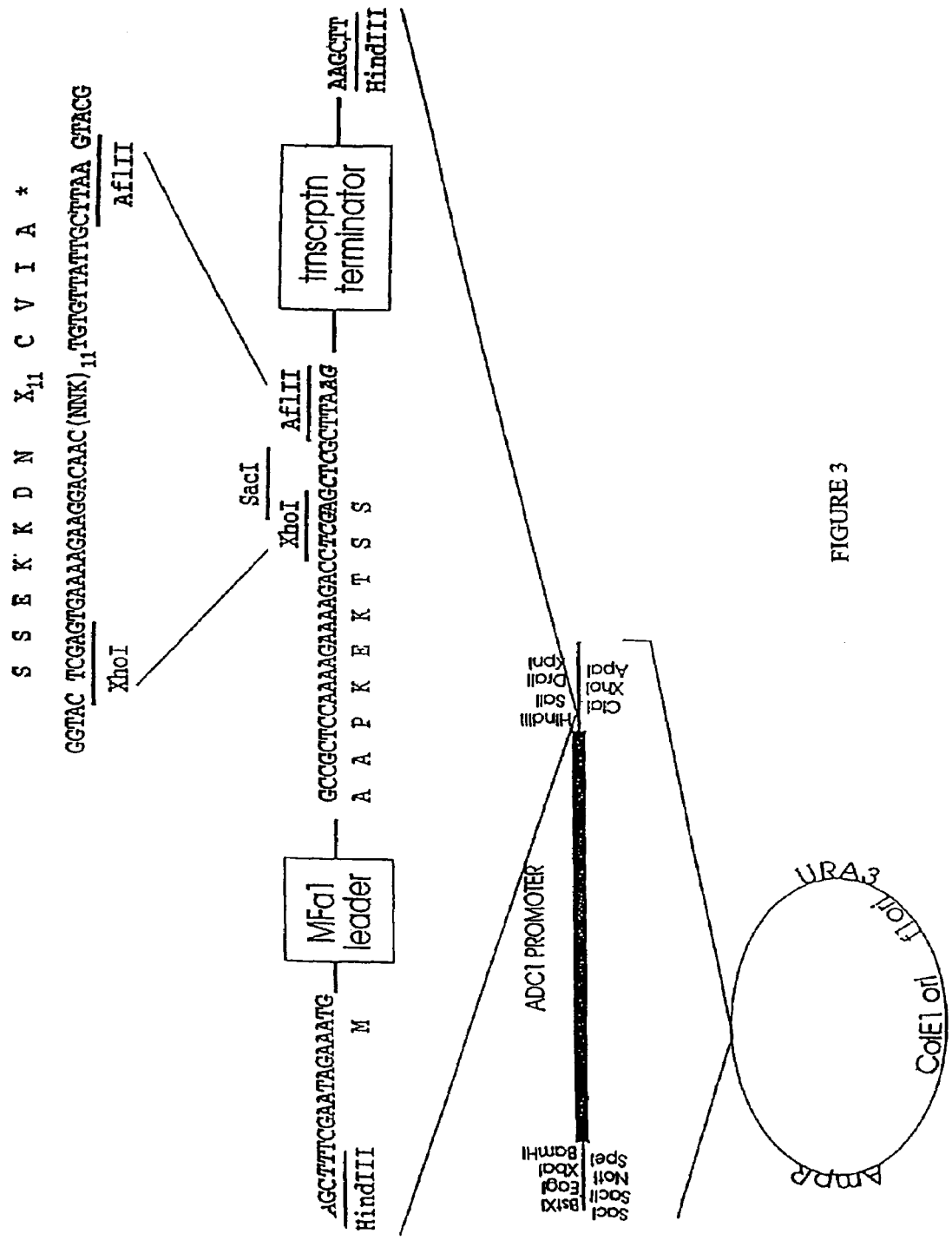
FIG. 3 is a schematic diagram of the structure of the plasmid resulting from insertion of random oligonucleotides into pADC-MFa. This plasmid expresses random peptides in the context of the MFa1 leader and C-terminal CVIA tetrapeptide.

The 1.6 kb HindIII fragment of the resulting plasmid, Cadus 1172, contains sequences encoding the MFA1 start codon and the N-terminal 16 amino acids of the leader peptide, followed by a short polylinker containing XhoI, SacI, and AflII sites for insertion of oligonucleotides. The 1.6 kb HindIII fragment of Cadus 1172 was ligated into HindIII-digested Cadus 1186 (see above) to place expression of sequences cloned into this cassette under the control of the ADH1 promoter. The SacI site in the polylinker was made unique by eliminating a second SacI site present in the vector. The resulting plasmid, designated Cadus 1239, can be prepared to accept oligonucleotides with XhoI and AflII ends by digestion with those restriction endonucleases for expression in the context of MFa1 leader peptides (FIG. 3).

Two single-stranded oligonucleotide sequences (see below) are synthesized, annealed, and repetitively filled in, denatured, and reannealed to form double-stranded oligonucleotides that, when digested with AflII and BglII, can be cloned into the polylinker of the expression vector, Cadus 1239. The two single-stranded oligonucleotides used for the cloning have the following sequences: 5'-GGTACTCGAGT-GAAAAGAAGGACAAC-3' (SEQ ID NO: 25) 5'-CG-TACTTAAGCAATAACACA(NNN)$_n$ GTTGTCCT-TCTTTTCACT CGAGTACC-3' (SEQ ID NO: 26) where N is any chosen nucleotide and n is any chosen integer. Yeast transformed with the resulting plasmids will transport—through the pathway normally used for the export of a-factor—farnesylated, carboxymethylated peptides whose amino acid sequence is determined by the particular choice of N and n (FIG. 3).

Example 4

Peptide Secretion/Transport.

This example demonstrates the ability to engineer yeast such that they secrete or transport oligonucleotide-encoded peptides (in this case their pheromones) through the pathways normally used for the secretion or transport of endogenous pheromones.

Autocrine MATa strain CY588:

A MATa strain designed for the expression of peptides in the context of MFα1 (i.e., using the MFα1 expression vector, Cadus 1215) has been constructed. The genotype of this strain, designated CY588, is MATa bar1 far1-1 fus1-HIS3 ste14::TRP1 ura3 trp1 leu2 his3. The bar1 mutation eliminates the strain's ability to produce a protease that degrades α-factor and that may degrade some peptides encoded by the cloned oligonucleotides; the far1 mutation abrogates the arrest of growth which normally follows stimulation of the pheromone response pathway; an integrated FUS1-HIS3 hybrid gene provides a selectable signal of activation of the pheromone response pathway; and, finally, the ste14 mutation lowers background of the FUS1-HIS3 readout. The enzymes responsible for processing of the MFa1 precursor in MATα cells are also expressed in MATa cells (Sprague and Thorner, in *The Molecular and Cellular Biology of the Yeast Saccharomyces: Gene Expression*, 1992, Cold Spring Harbor Press), therefore, CY588 cells should be able to secrete peptides encoded by oligonucleotides expressed from plasmid Cadus 1215.

A high transforming version (tbt1-1) of CY588 was obtained by crossing CY1013 (CY588 containing an episomal copy of the STE14 gene) (MATa bar1::hisGfar1-1 fus1-HIS3 ste14::TRP1 ura3 trp1 leu2 his3 [STE14 URA3 CEN4) to CY793 (MATα~tbt1-1 ura3 leu2 trp1 his3fus1-HIS2 can1 ste114::TRP1 [FUS1 LEU2 2μ]) and selecting from the resultant spores a strain possessing the same salient genotype described for CY588 (see above), and in addition the tb1-1 allele, which confers the capacity for very high efficiency transformation by electroporation. The selected strain is CY1455 (MATabar1::hisGfar1-1 fus1-HIS3 ste14::TRP1 tbt-1 ura3 trp1 leu2 his3).

Secretion of Peptides in the Context of Yeast α-factor:

Experiments were performed to test: (1.) the ability of Cadus 1215 to function as a vector for the expression of peptides encoded by synthetic oligonucleotides; (2.) the suitability of the oligonucleotides, as designed, to direct the secretion of peptides through the α-factor secretory pathway; (3.) the capacity of CY588 to secrete those peptides; and (4.) the ability of CY588 to respond to those peptides that stimulate the pheromone response pathway by growing on selective media. These experiments were performed using an oligonucleotide which encodes the 13 amino acid α-factor; i.e., the degenerate sequence $(NNN)_n$ in the oligonucleotide cloned into Cadus 1215 (see above) was specified (n=13) to encode this pheromone. CY588 was transformed with the resulting plasmid (Cadus 1219), and transformants selected on uracil-deficient medium were transferred to histidine-deficient medium supplemented with a range of concentrations of aminotriazole (an inhibitor of the HIS3 gene product that serves to reduce background growth). The results demonstrate that the synthetic oligo-nucleotide, expressed in the context of MFα1 by Cadus 1215, conferred upon CY588 an ability to grow on histidine-deficient media supplemented with aminotriazole. In summation, these data indicate that: (1.) CY588 is competent for the secretion of a peptide encoded by the $(NNN)_n$ sequence of the synthetic oligonucleotide cloned into and expressed from Cadus 1215; and (2.) CY588 can, in an autocrine fashion, respond to a secreted peptide which stimulates its pheromone response pathway, in this case by α-factor binding to STE2.

Autocrine Mata Strain CY599:

A MATa strain designed for the expression of peptides in the context of MFA1 (i.e., using the MFA1 expression vector, Cadus 1239) has been constructed. The genotype of this strain, designated CY599, is MATa mfa1 mfa2 far1-1 his3::fus1-HIS3 ste2-STE3 ura3 met1 ade1 leu2. In this strain, Cadus 1147 (see above) was used to replace STE2 with a hybrid gene in which the STE3 coding region is under the control of expression elements which normally drive the expression of STE2. As a result, the a-factor receptor replaces the α-factor receptor. The genes which encode a-factor are deleted from this strain; the far1 mutation abrogates the arrest of growth which normally follows stimulation of the pheromone response pathway; and the FUS1-HIS3 hybrid gene (integrated at the HIS3 locus) provides a selectable signal of activation of the pheromone response pathway. CY599 cells were expected to be capable of the transport of a-factor or a-factor-like peptides encoded by oligonucleotides expressed from Cadus 1239 by virtue of expression of the endogenous yeast transporter, Ste6.

Transport of Peptides by the Yeast a-factor Pathway:

Experiments were performed to test: (1.) the ability of Cadus 1239 to function as a vector for the expression of peptides encoded by synthetic oligonucleotides; (2.) the suitability of the oligonucleotides, as designed, to direct the export of farnesylated, carboxymethylated peptides through the pathway normally used by a-factor; (3.) the capacity of CY599 to export these peptides; and (4.) the ability of CY599 to respond to those peptides that stimulate the pheromone response pathway by growing on selective media. These tests were performed using an oligonucleotide which encodes the 12 amino acid a-factor; specifically, the degenerate sequence $(NNN)_n$ in the oligonucleotide cloned into Cadus 1239 (see above) (with n=12) encodes the peptide component of a-factor pheromone. CY599 was transformed with the resulting plasmid (Cadus 1220), and transformants selected on uracil-deficient medium were transferred to histidine-deficient medium supplemented with a range of concentrations of aminotriazole. The results demonstrate that the synthetic oligonucleotide, expressed in the context of MFA1 by Cadus 1220, conferred upon CY599 enhanced aminotriazole-resistant growth on histidine-deficient media. In summation, these data indicate: (1.) Cadus 1220 and the designed oligonucleotide are competent to direct the expression and export of a farnesylated, carboxymethylated peptide encoded by the $(NNN)_n$ sequence of the synthetic oligonucleotide; and (2.) CY599 can, in an autocrine fashion, respond to a farnesylated, carboxymethylated peptide that stimulates its pheromone response pathway, in this case signaling initiates as a-factor binds to STE3.

Example 5

Proof of Concept

This example will demonstrate the utility of the autocrine system for the discovery of peptides which behave as functional pheromone analogs. By analogy, this system can be used to discover peptides that productively interact with any pheromone receptor surrogates.

CY588 (see strain 5, Example 2 above) will be transformed with CADUS 1215 containing oligonucleotides encoding random tridecapeptides for the isolation of functional α-factor analogs. CYS99 (see strain 6, Example 2 above) will be transformed with CADUS 1239 containing oligos of random sequence for the isolation of functional a-factor analogs. Colonies of either strain which can grow on histidine-deficient media following transformation will be expanded for the preparation of plasmid DNA, and the oligo-nucleotide cloned into the expression plasmid will be sequenced to determine the amino acid sequence of the peptide which presumably activates the pheromone receptor. This plasmid will then be transfected into an isogenic strain to confirm its ability to encode a peptide which activates the pheromone receptor. Successful completion of these experiments will demonstrate the potential of the system for the discovery of peptides which can activate membrane receptors coupled to the pheromone response pathway.

Random oligonucleotides to be expressed by the expression plasmid CADUS 1215 will encode tridecapeptides constructed as

5'-CGTGAAGCTTAAGCGTGAGGCAGAAGCT$(NNK)_{13}$TGATCATCCG-3' (SEQ ID NO: 27), where N is any nucleotide, K is either T or G at a ratio of 40:60 (see Proc. Natl. Acad. Sci. 87:6378, 1990; ibid. 89:5393, 1992), and the AflII and BclI sites are underlined. This oligonucleotide is designed such that: the AflII and BclI sites permit inserting the oligos into the AflII and BglII site of CADUS 1215, the HindIII site just 5' to the AflII site in the 5' end of the oligo allows future flexibility with cloning of the oligos; the virtual repeat of GAGGCT and the GAGA repeats which are present in the wild-type sequence and which can form triple helixes are changed without altering the encoded amino acids. The random oligonucleotides described above will actually be constructed from the following two oligos:

5'- CGTGAAGCTTAAGCGTGAGGCAGAAGCT-3' (SEQ ID NO: 28) and

5'- CGGATGATCA$(MNN)_{13}$AGCTTCTG-3' (SEQ ID NO: 29), where M is either A or C at a ratio of 40:60. The oligos will be annealed with one another and repetitively filled in, denatured, and reannealed (Kay et al., Gene, 1993). The double-stranded product will be cut with AflII and BclI and ligated into the AflII- and BglII-digested CADUS 1215. The BglII/BclI joint will create a TGA stop codon for termination of translation of the randomers. Because of the TA content of the Afl overhang, the oligos will be ligated to the AflII- and BglII-digested pADC-MFα at 4° C.

Random oligonucleotides to be expressed by the expression plasmid CADUS 1239 will encode monodecapeptides constructed as 5'-GGTACTCGAGTGAAAAGAAGGA-CAAC(NNK)₁₁TGTGTTATTGCTTAAGTACG-3' (SEQ ID NO: 30), where N is any nucleotide, K is either T or G at a ratio of 40:60 (see Proc. Natl. Acad. set 87:6378, 1990; ibid 89:5393, 1992). When cloned into the XhoI and AflII sites of CADUS 1239 the propeptides expressed under the control of the ADH1 promoter will contain the entire leader peptide of MFa1, followed by 11 random amino acids, followed by triplets encoding CVIA (the C-terminal tetrapeptide of wild-type a-factor). Processing of the propeptide should result in the secretion of dodecapeptides which contain 11 random amino acids followed by a C-terminal, farnesylated, carboxymethylated cysteine.

Using the procedure described above, the oligonucleotides for expression in CADUS 1239 will actually be constructed from the following two oligos:
5'-GGTACTCGAGTGAAAAGAAGGACAAC-3' (SEQ ID NO: 31) and
5'-CGTACTTAAGCAATAACAca(MNN)₁₁GTTGTCC-3', (SEQ ID NO: 32)
where M is either A or C at a ratio of 40:60, and the XhoI and AflII sites are underlined.

Discovery of a-factor Analogs from a Random Peptide Library

An optimized version of strain 6 (Example 2 above) was derived. This yeast strain, CY2012 (MATa ste2-STE3 far1Δ1442 mfa1::LEU2 mfa2-lacZ fus1-HIS3 tbt1-1 ura3 leu2 his3 trp1 suc2), was constructed as follows. From a cross of CY570 (MATa mfa1::LEU2 mfa2-lacZ ura3 trp1 his3Δ200 can1 leu2 fus1-HIS3 [MFA1 URA3 2μ] [Fus1 Δ8-73 TRP1 CEN6]) by CY1624 (MATα tbt1-1 fus1-HIS3 trp1 ura3 leu2 his3 lys2-801 SUC+), a spore was selected (CY1877) of the following genotype: MATa mfa1::LEU2 mfa2-lacZ fus1-HIS3 tbt1-1 ura3 leu2 his3 trp1 suc2. This strain lacks both genes (NFA1 and MFA2) encoding a-factor precursors, contains the appropriate pheromone pathway reporter gene fus1-HIS3), and transforms by electroporation at high efficiency (tbt1-1). This strain was altered by deletion of the FAR1 gene (with Cadus 1442; see Example 6), and replacement of STE2 coding sequences with that of STE3 (see Example 1) to yield CY2012.

This strain was transformed with plasmid DNA from a random a-factor library by electroporation and plated on 17 synthetic complete plates lacking uracil (-Ura), yielding approximately 10⁵ Ura+colonies per plate after 2 days at 30° C. These colonies were replica plated to histidine-deficient synthetic complete media (-His) containing 0.2 mM 3-aminotriazole and after three days at 30° C. 35 His+ replicas were streaked to -Ura plates. The resultant colonies, 3 from each isolate, were retested for their His+ phenotype, and streaked to 5-fluoroorotic acid plates to obtain Ura segregants (lacking a library plasmid). Those Ura-segregants were tested for the loss of their His+ phenotype. Ten of the original isolates passed these tests; in two cases only one of the three Ura+ colonies purified from the isolate retained the His+ phenotype, but nevertheless subsequently segregated Ura His- colonies.

A single plasmid (corresponding to a bacterial colony) was obtained from each of the ten isolates, and reintroduced into CY2012. Eight of the ten plasmids passed the test of retaining the ability to confer the His+ phenotype on CY2012 (the two that failed correspond to the two isolates that were mentioned above, suggesting that these isolates contain at least one "irrelevant" plasmid). Sequencing of the randomized insert in the eight plasmids of interest revealed that four contain the sequence:
TAT GCT CTG TTT GTT CAT TTT TTT GAT ATT CCG (SEQ ID NO: 33)
Tyr Ala Leu Phe Val His Phe Phe Asp Ile Pro (SEQ ID NO: 34)
two contain the sequence:
TTT AAG GGT CAG GTG CGT TTT GTG GTT CTT GCT (SEQ ID NO: 35)
Phe Lys Gly Gln Val Arg Phe Val Val Leu Ala, (SEQ ID NO: 36)
and two contain the sequence:
CTT ATG TCT CCG TCT TTT TTT TTT TTG CCT GCG (SEQ ID NO: 37)
Leu Met Ser Pro Ser Phe Phe Phe Leu Pro Ala (SEQ ID NO: 38)

Clearly, these sequences encode novel peptides, as the native a-factor sequence differs considerably:
Tyr Ile Ile Lys Gly Val Phe Trp Asp Pro Ala. (SEQ ID NO: 39)

The a-factor variants identified from random peptide libraries have utility as "improved" substrates of ABC transporters expressed in yeast. For example, identification of a preferred substrate of human MDR, one that retains agonist activity on the pheromone receptor, would permit the establishment of robust yeast screens to be used in the discovery of compounds that affect transporter function.

Example 6

Identification of a surrogate ligand using expression of a random peptide library in yeast expressing an orphan mammalian receptor In this example, experiments detailing the following will be described: (1) establishment of a strain of yeast designed to express the human orphan G protein-coupled receptor FPRL-1; (2) expression of a random peptide library in the aforementioned strain of yeast; and (3) activation of the endogenous yeast pheromone pathway upon stimulation of the FPRL-1 receptor by a peptide encoded by a random library expressed within the same strain of yeast.

Preparation of FPRL-1 Yeast Expression Vector

A plasmid, pFPRL1-L31, containing a 2.6 kb EcoRI-XhoI fragment encoding the FPRL-1 cDNA in the BluescriptI-ISK+ vector was obtained from Philip Murphy (NIH). The sequence encoding FPRL1 was amplified by the polymerase chain reaction using VENT polymerase (New England Biolabs, Inc., Beverly, Mass.) through 20 cycles and the following oligonucleotide primers:
15'-GGCGCCCGGTCTCCCATGGAAACCAACT-TCTCCACT-3' (SEQ ID NO: 40)
25'-GGCGCCCGGTCTCCGATCCCATTGCCTG-TAACTCAGTCTC-3' (SEQ ID NO: )

The PCR product was purified, restricted with BsaI and cloned into Cadus 1651 (plPBX-1), a PGK promoter-driven expression vector, using NcoI and BamHI sites, to yield CADUS 2311. The sequence of the entire insert was determined and found to be identical to the FPRL-1 sequence deposited in GenBank (accession number M84562).

Preparation of Random Oligonucleotides

Library-Recycling Protocol to Identify a Surrogate Ligand

The yeast strain CY1141 (MATalpha far1*1441 tbt1-1 fus1-HIS3 can 1 ste14::trp1:;LYS2 ste3*1156 gpa1(41)-Galphai2 lys2 ura3 leu2 trp1 his3) was used in the experiments that follow. CY1141 contains a pheromone inducible HIS3 gene, fus1-HIS3 integrated at the FUS1 locus and a hybrid gene encoding the first 41 amino acids of GPA1 (yeast G alpha) fused to sequence encoding human G alphai2 (lacking codons encoding the N-terminal 33 amino acids) replacing GPA1 at its chromosomal locus. The yeast STE14 gene is disrupted to lower the basal level of signaling through the pheromone response pathway. The yeast a-factor receptor gene, STE3, is deleted. CY1141 was transformed with Cadus 2311 to yield CY6571, a strain expressing the human orphan receptor, FPRL-1.

CY6571 exhibited LIRMA (ligand independent receptor mediated activation), that is, activation of the yeast pheromone pathway in the absence of ligand. It was determined that the yeast growth on selective media that resulted from LIRMA was eliminated by the additional of 2.5 millimolar concentrations of 3-aminotriazole (AT). AT is an inhibitor of the HIS3 gene product that serves to reduce background growth. Therefore, selection protocols aimed at the identification of surrogate ligands for the FPRL-1 receptor were carried out at this concentration of AT.

CY6571 was inoculated to 10 mls of standard synthetic media (SD) lacking leucine (-Leu) and incubated overnight at 30° C. The 10 ml overnight culture was used to inoculate 50 mls of YEPD; this culture was incubated at 30° C. for 4.5-5 hours at which time the cells were harvested and prepared for transformation with DNA encoding a random peptide library [alpha-NNK (6.24.94)] encoding tridecapeptides of random sequence, by electroporation. Post electroporation (in 0.2 cm cuvettes, 0.25 μF, 200Ω, 1.5 kV) the cells were immediately diluted in 1 ml ice-cold 1M sorbitol and 100 μL aliquots were placed onto 10 synthetic media plates (pH6.8) lacking leucine and uracil (-Leu-Ura). The plates were incubated at 30° C. for 2-4 days at which time two replicas of each original transformation plate were made to synthetic media (pH6.8) lacking leucine, uracil and histidine and supplemented with 2.5 mM AT(-Leu-Ura-His+2.5 mM AT). The replicas were incubated at 30° C. for 3-5 days. Post incubation the colonies present on the replica sets of two were scraped from the plates into a total of 10 mls of $H_2O$ (5 mls each plate). The $OD_{600}$ of each cell suspension was determined and crude plasmid isolations were done on 8-16 OD units of cells for each pool. A total of eight pools resulted, due to lower numbers of yeast colonies present in four sets of plates. The pellets obtained from these crude plasmid isolations (the so called "smash and grab" technique, Methods in Yeast Genetics—A Laboratory Manual, 1990, M. D. Rose, F. Winston and P. Heiler. Cold Spring Harbor Laboratory Press, Cold Spring Harbor, N.Y.), were resuspended in 40 μL of 10 mM Tris, 1 mM EDTA, pH8.0 and 1 μL was used to transform E. coli by electroporation (0.1 cm cuvettes, 0.25 μF, 200Ω, 1.8 kV). Post electroporation the cells were immediately diluted into 1 ml 2XYT media and incubated, with shaking, at 37° C. for 30 minutes after which time the cells were used to inoculate 50 mls of 2xYT supplemented with 100 μg/ml ampicillin. The 10 resulting cultures were incubated at 37° C. overnight. Plasmid DNA was isolated from each of these bacteria cultures using Qiagen columns (Qiagen, Inc., Chatsworth, Calif.)). Each plasmid DNA pellet was resuspended in 50 μL Tris 10 mM, EDTA 1 mM, pH 8.0.

Strain CY6571 was transformed with 1 μL of each plasmid pool by electroporation. Post electroporation the cells were diluted into 400 μL 1M sorbitol. From each electroporated cell suspension, 1 μL and 400 μL of cells were plated on -Leu-Ura synthetic media, pH6.8 to yield "low density" and "high density" platings. The plates were incubated at 30° C. for 3 days, at which time replicas of both the low and high density plates were made to -Leu-Ura-His+2.5 mM AT. For those cases where enrichment for a plasmid capable of conferring a His+ phenotype had occurred, this would be reflected by an amplified number of His+ colonies on both the low and high density plates visible at days 2-3, although the amplification would be most obvious on the plates that had received a high density of cells. In the FPRL-1 experiment ⅛ pools showed amplification of His+ colonies. The cells were scraped from this plate into 5 mls of $H_2O$, the $OD_{600}$ of the cell suspension was determined and a crude plasmid isolation was done on 15 OD units of yeast cells. The pellet obtained was resuspended in 40 μL 10 mM Tris, 1 mM EDTA, pH8.0 and 1 μL was used to transform E. coli. Plasmid DNA was isolated by miniprep from 3 ml 2XYT cultures of single bacterial colonies resulting from this transformation. 10 DNA pellets (A1 through A10) deriving from individual bacterial colonies were resuspended in 20 μL 10 mM Tris 1 mM EDTA, pH8.0 and used to transform CY6571 (containing the FPRL-1 expression vector) and CY6263 (CY1141 containing a control expression vector lacking any receptor sequence) by electroporation. Cadus 1625, a control vector lacking sequences encoding a peptide, was included and used to transform both the receptor+ and receptor– strains of yeast. Transformants were first selected on -Leu-Ura, pH6.8 then three yeast transformants of each type (from 11 CY6571 transformations and 11 CY6263 transformations) were patched to -Leu-Ura, pH6.8 to expand the colonies. Once expanded, streaks of the transformants were made on -Leu-Ura-His+2.5 mM AT to test for growth in the absence of histidine. All plasmids except the one denoted A2 conferred a growth advantage on media lacking histidine to yeast bearing the FPRL-1-encoding plasmid but not to yeast lacking the receptor plasmid. The peptide sequence found to be encoded by plasmids A1 and A3-A10 is: -Ser-Leu-Leu-Trp-Leu-Thr-Cys-Arg-Pro-Trp-Glu-Ala-Met (SEQ ID NO: 1), and is encoded by the nucleotide sequence 5'-TCT CTG CTT TGG CTG ACT TGT CGG CCT TGG GAG GCG ATG-3' (SEQ ID NO: 42).

Activation of the Pheromone Response Pathway in Yeast Expressing the FPRL-1 Receptor and Peptide Agonist.

For verification of pheromone pathway activation and quantification of the stimulation, the activity of the fus1 promoter was determined colorimetrically using a fus1-lacZ fusion in a parallel set of test strains. CY1141, described above, was used as the recipient strain for these experiments. Transformants contained CADUS 1584 (pRS424-fus1-lacZ) in addition to receptor ($R^{+/-}$) and ligand ($L^{+/-}$) plasmids. Four strains (bearing the identical plasmids) were grown overnight in minimal media lacking leucine, uracil, and tryptophan, pH8.6. The overnight cultures were used to inoculate-Leu-Ura-Trp pH6.8 media and these new cultures were grown for approximately 4.5-5 hours to an $OD_{600}$ of less than 0.4. Assay of β-galactosidase activity (Guarente 1983) in cells from these cultures yielded the following results:

| | | |
|---|---|---|
| CY1141/CADUS 2311/peptide A1/CADUS 1584 | R⁺L⁺ | 28 units |
| CY1141/CADUS 2311/CADUS 1625/CADUS 1584 | R⁺L⁻ | 3 units |
| CY1141/CADUS 1289/peptide A1/CADUS 1584 | R⁻L⁺ | 3.5 units |
| CY1141/CADUS 1289/CADUS 1625/CADUS 1584 | R⁻L⁻ | 3.9 units |

The presence of receptor and peptide-encoding plasmids resulted in an average 8-fold stimulation over background levels of β-galactosidase.

Autocrine Activation of the Pheromone Response Pathway in Yeast Expressing by FPRL-1 Agonists or C5a Receptor Agonists.

Figure 4:
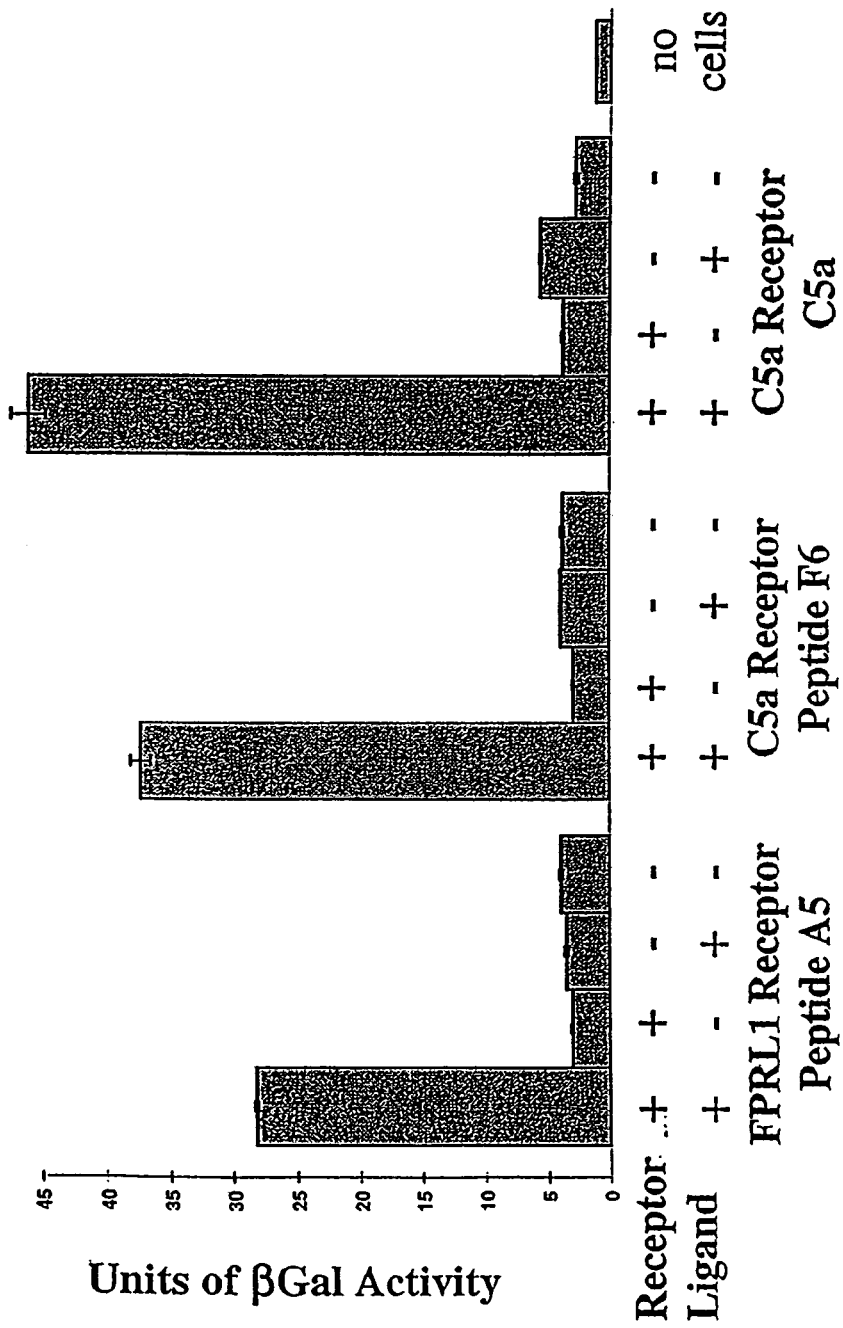
FIG. 4 depicts the autocrine activation of the pheromone response pathway in yeast expressing FPRL-1 agonists or C5a receptor agonists.

The results illustrated in FIG. 4 were obtained using yeast cells engineered to express FPRL-1 or the C5a receptor under conditions wherein the signal transduction from the heterologous receptor was coupled to a fus1:lacZ reporter gene construct described above. FIG. 4 demonstrates the specificity of the surrogate ligand A5 for FPRL-1, and the surrogate ligand F6, as well as that of the native C5a ligand, for the C5a receptor. In each instance, the presence of both the receptor and surrogate peptide result in an 8-12 fold increase in lacZ expression over the level observed in the absence of either the receptor, ligand, or both.

Activation of Human Neutrophils by a Surrogate FPRL Agonist.

Figure 5:
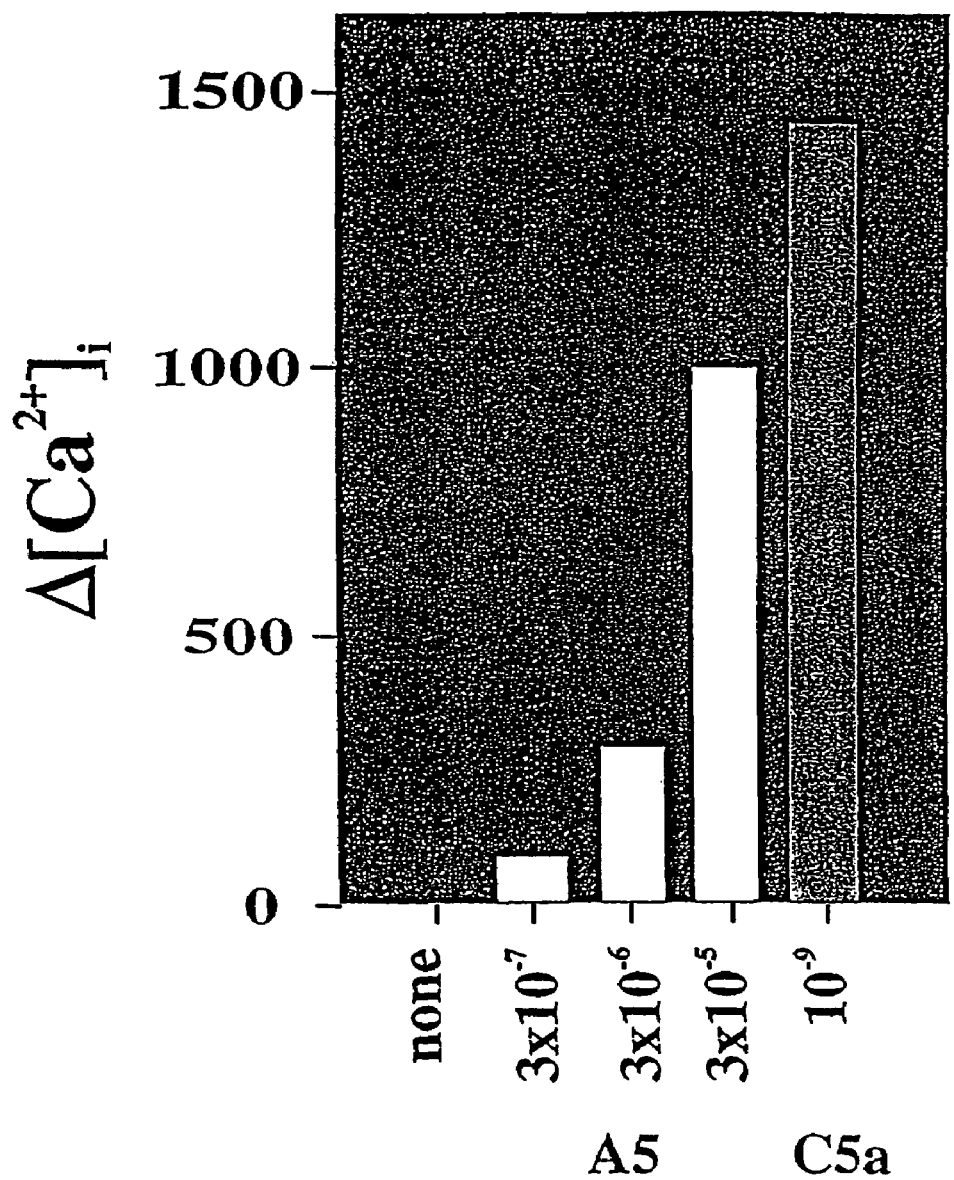
FIG. 5 depicts intracellular $Ca^{2+}$ mobilization in neutrophils as detected by fluorescence activated Cell Sorter analysis using FURA2 dye absorbance ratio. The measurements were performed for the C5a peptide, or no peptide (control), or varying concentrations of the A5 peptide.

Human neutrophils in culture were stimulated with varying concentrations of the FPRL surrogate ligand A5, and intracellular $Ca^{2+}$ mobilization was detected by Fluorescence Activated Cell Sorter (FACS) analysis based on FURA2 dye absorbance ratios. The response of the human neutrophils to the C5a peptide was also measured. As shown in FIG. 5, the A5 peptide produced a dose-dependent increase in intracellular calcium mobilization, indicating that it is capable of activating endogenous FPRL-mediated pathways in human neutrophils.

Preparation of Second Generation FPRL Ligand Libraries.

To improve further the selectivity and/or potency of the agonists identified by the above steps, a surrogate peptide (A5) was selected, and degenerate peptide libraries, based on the sequence of that peptide as a starting point (e.g. a semi-random library) were created as follows:

FPRL-1 peptide A5, Ser-Leu-Leu-Trp-Leu-Thr-Cys-Arg-Pro-Trp-Glu-Ala-Met (SEQ ID NO: 1)

sub-libraries

N-term, Xaa-Xaa-Xaa-Xaa-Xaa-Thr-Cys-Arg-Pro-Trp-Glu-Ala-Met (SEQ ID NO: 44)

mid4, Ser-Leu-Leu-Trp-Leu-Xaa-Xaa-Xaa-Xaa-Trp-Glu-Ala-Met (SEQ ID NO: 44)

C-term, Ser-Leu-Leu-Trp-Leu-Thr-Cys-Arg-Pro-Xaa-Xaa-Xaa-Xaa (SEQ ID NO: 45)

mod2, Xaa-Leu-Xaa-Trp-Xaa-Thr-Xaa-Arg-Xaa-Trp-Xaa-Ala-Xaa (SEQ ID NO: 46)

mod3, Ser-Xaa-Leu-Xaa-Leu-Xaa-Cys-Xaa-Pro-Xaa-Glu-Xaa-Met (SEQ ID NO: 47)

Following the protocols set out above for the first generation peptide library, the second generation peptide library was screened, and individual clones isolated based on their ability to stimulate FPRL receptor dependent transcription.

Example 7

Additional surrogate ligands identified from expression of a random peptide library in yeast cells expressing an orphan mammalian receptor In addition to the peptide ligand for FPRL-1 orphan receptor described in Example 6, six more peptides have been identified from expression of a random peptide library in yeast cells.

I. Material and Methods

Preparation of Plasmids

For expression in yeast, sequences encoding human FPRL-1 receptor were amplified by PCR from plasmid pFPRL1-L31 as described in Example 6. The amplified sequences were cloned into the yeast expression vector Cp1651 (bla LEU2 ARS-2mp PGKlp), placing the gene under the control of the PGKI promoter to yield Cp2311.

For mammalian expression, the Xbal-XhoI fragment from pFPR-D15 spanning FPR1 and its 3' untranslated region was cloned into NheI- and XhoI-digested pCEP4 (In Vitrogen, San Diego, Calif.) to yield Cp3155. Similarly, the MfeI-XhoI fragment spanning FPRL-1 receptor and its 3' untranslated region was excised from pFPRL1-L31 and cloned into PvuII- and XhoI-digested pCEP4 to yield Cp3157. In these vectors containing the selectable marker neo, expression of human FPR1 or FPRL-1 was under the control of a CMV promoter.

Preparation of Peptides

Random peptide expression libraries were generated by synthesizing oligonucleotides with a triplet scheme of $(NNK)_{13}$ or $(NNK)_{20}$ wherein N specifies an equimolar mixture of A, C, G, and T, and K specifies an equimolar mixture of G and T, followed by subcloning the resultant molecules into the yeast expression vector Cp1625 (Manfredi et al. (1996) *Mol. and Cell. Biol.* 16:4700-4709). The libraries, NNK-13 and NNK-20, comprised approximately $10^8$ members each.

Peptides AF-1, AF-2, AF-3, MMK-1, DM-1, A5, formyl-A5, fMLP, MMWLL and fMMWWLL were synthesized and purified to >90% purity, as determined by HPLC. N-MeF-K-P-dCha-Cha-dR and N-MeF-K-P-dChaF-dR were synthesized and purified to ≧95% purity, as determined by HPLC.

Preparation of Yeast Strains

As described in Example 6, strain CY6571 was constructed by transforming plasmid Cp2311 into strain CY1141 (MATα far1Δ1442 fus1-HIS3 ste14::trp1::LYS2 ste3Δ1156 gpa1(41)-Gαi2 lys2 ura3 leu2 trp1 his3). Strain CY1141 contains an integrated copy of a hybrid Gα gene, gpa1 (41)-Gαi2, which encodes the N-terminal 41 amino acids of Gpa1p fused to sequence encoding human Gαi2 (lacking codons for the N-terminal 33 amino acids). Expression of the HIS3 gene is under the control of the FUS1 promoter. Strain CY6565 is equivalent to CY2311 and also carries plasmid Cp1584 (bla LEU2 ARS-2mu FUS1-lacZ).

Cell Lines

Human cells expressing FPR1 or FPRL1 were derived from HEK293 cells constitutively expressing human $G\alpha_{16}$ under the control of a CMV promoter. Cells were transfected with Cp3155 or Cp3157, subjected to selection in the presence of 400 μg/ml hygromycin and 200 μg/ml G418 and individual drug-resistant clones were assayed for receptor expression by Northern blot and functional analysis. Cell lines responsive to ligand were expanded and maintained at 37° C./5% $CO_2$ in DMEM GlutaMax (Gibco-BRL) supplemented with 10% newborn calf serum, 200 µg/ml G418 and 400 µg/ml hygromycin.

Assays of Receptor Activation in Yeast

Receptor activation in yeast strains carrying a fus1-HIS3 construct was evaluated by growth on LUH-AT media (synthetic complete medium lacking leucine, histidine and uracil[16], adjusted to pH 6.8 with KOH and supplemented with 2.5 mM 3-aminotriazole, as previously described in Example 6. Aminotriazole is a competitive inhibitor of IGP dehydratase, the product of HIS3, (Kloptowski T., et al. (1965). Arch. Biochem. Biophys. 112: 562-566; Struhl, et al. (1977) Proc. Natl. Acad. Sci. USA 74:5255-259) and can be used to suppress growth due to background signaling through the pheromone response pathway. Activation of receptor by exogenous peptide addition to strains containing fus1-lacZ was measured in 96-well plates seeded with cells at a concentration of 0.15 $OD_{600}$ units per ml. Serial dilutions of each peptide were added and the plate incubated 5 h at 30° C. At 5 hours, a lysis buffer containing the substrate chlorophenolred-β-D-galactopyranoside (CPRG) was added and activity was determined after incubation at 30° C. for 1 hr by determining optical density at 575 nM.

Assays of Receptor Activation in HEK293 Cells

Activation of receptors in HEK293 cells was measured on a fluorometric imaging plate reader. Cells were loaded with Fluo-3 in the presence of probenecid for one hour at 37° C. Solution containing dye was removed and cells were washed once with HBSS/20mM HEPES/probenecid prior to compound addition and assay.

Receptor Activation of Human Neutrophils Determined by Calcium Mobilization

Receptor activation of human neutrophils was determined by measuring calcium mobilization at the addition of the ligand. Neutrophils were isolated from whole blood obtained from healthy human donors. Cells were loaded with indo-AM (Molecular Probes, Eugene, Oreg.) and were analyzed at room temperature on an Epics Elite flow cytometer equipped with a 20 mW HeCd laser to provide a 325 nm excitation source (Coulter Corp., Hialeah, Fla.). Cells were analyzed with respect to forward low angle light scatter of the UV beam, violet (382 nm) and blue (488 nm) fluorescence emissions using band pass filters, the ratio of violet to blue fluorescence and the fluorescence ratio of the population with respect to time. The files were gated using scatter and dye loading criteria to exclude debris and moribund cells. Samples were analyzed for 5 minutes after addition of ligand and the peak $Ca^{2+}$ response was determined using MTIME software (Phoenix Flow Systems, San Diego, Calif.).

II. Results

Selection of Surrogate Agonists in Yeast.

The yeast strain CY6571 designed to express FPRL-1 and to couple mammalian GPCRs to the endogenous pheromone response pathway, was used to isolate surrogate ligands for FPRL-1. The strain was engineered, so that activation of the pathway permitted growth in the absence of histidine. In addition, the strain contained a mammalian/yeast hybrid Gα subunit that served as a connector between the mammalian receptor and the yeast Gβγ subunits, the initial effectors of the pheromone pathway, so that activation of the receptor would stimulate signal transduction. Similar strains for functional expression of a variety of human GPCRs, have been used. These include human C5a receptor and FPR1, yielding strains whose histidine prototrophy depends on stimulation of the expressed GPCR by endogenous co-expression or exogenous application of the cognate ligand.

To identify surrogate ligands, strain CY6571 was transformed with a plasmid library, NNK-13, designed to express and secrete random tridecapeptides. Transformants (ca $1 \times 10^6$) were selected on plates lacking uracil to recover plasmid-bearing strains and then individual transformation plates (containing ca $1 \times 10^5$ transformants/plate) were replicated to plates lacking histidine to select for autocrine cell growth. This yielded approximately 100 prototrophic colonies per plate. A majority of yeast transformants produced peptides that did not interact with FPRL-1 and failed to grow in the absence of histidine. The prototrophic colonies represented both genetic revertants (Stevenson, et al., (1992) Genes Dev. 6:1293-1304) as well as colonies in which the peptide synthesized by the cells stimulated FPRL-1, rendering the cells capable of growth in the absence of histidine. To identify the true autocrine clones among the background of genetic revertants, all the His+ colonies were pooled, plasmid DNA was extracted and the plasmids were amplified in E. coli. A naive culture of strain CY6571 was transformed to uracil prototrophy with the pool of recovered plasmids and the transformation plates replicated onto plates lacking histidine. As a result of the enrichment for autocrine peptide-expressing clones after the first round of selection, the frequency of histidine prototrophs among transformants in the second round of selection was substantially higher than in the first ($1/10^2$ versus $1/10^4$ His+/Ura+ clones). In addition, plasmids recovered from 9 out of 10 individual histidine prototrophs in one such experiment were identical, yielding a predicted tridecamer sequence that was designated as peptide A5. Five additional peptide-encoding plasmids that promoted growth of the FPRL-1-bearing strain, following independent transformations of CY6571 with NNK-13 or with a library encoding 20-mer peptides were also recovered. The additional five peptides are referred to as MMk-1, AF-1, AF-2, AF-3 and DM-1. (see Table 1).

TABLE 1

Agonist Activity of Surrogate Peptide Ligands on FPRL-1 vs. FPR1.

| Peptide | Sequence | $EC_{50}$ (nM) | |
|---|---|---|---|
| | | FPRL$^{-1}$ | FPR1 |
| MMK-1 | Leu-Glu-Ser-Ile-Phe-Arg-Ser-Leu-Leu-Phe-Arg-Val-Met (SEQ ID NO: 2) | <2 | >10,000 |
| AF-1 | Cys-Pro-Ala-Ala-Val-Leu-Trp-Arg-Trp-Val-Pro-Met (SEQ ID NO: 3) | 16 | 5 000 |
| A5 | Ser-Leu-Leu-Trp-Leu-Thr-Cys-Arg-Pro-Trp-Glu-Ala-Met (SEQ ID NO: 1) | 35 | >10,000 |
| AF-2 | Ser-Met-Cys-Pro-Thr-Ala-Ser-Ala-Trp-Val-Trp-Leu-Met (SEQ ID NO: 4) | 87 | 690 |
| AF-3 | RFPKNCHLRPPRMILFTALV Arg-Phe-Pro-Lys-Asn-Cys-His-Leu-Arg-Pro-Pro-Arg-Met-Ile-Leu-Phe-Thr-Ala-Leu-Val (SEQ ID NO: 5) | 650 | 380 |
| DM-1 | Pro-Pro-Phe-Phe-Phe-Arg-Pro-Val-Gly-Met-Phe (SEQ ID NO: 6) | 2400 | >10,000 |
| MMWLL | Met-Met-Trp-Leu-Leu (SEQ ID NO: 7) | 80 | <0.3 |

TABLE 1-continued

Agonist Activity of Surrogate Peptide Ligands on FPRL-1 vs. FPR1.

| Peptide | Sequence | EC$_{50}$ (nM) FPRL$^{-1}$ | FPR1 |
|---------|----------|---------------------------|------|
| f-A5 | formyl-Ser-Leu-Leu-Trp-Leu-Thr-Cys-Arg-Pro-Trp-Glu-Ala-Met (SEQ ID NO: 8) | 2 | 10 |
| fMLP | formyl-MLF | 40 | <0.3 |

The first six peptides listed were identified as potential FPRL-agonists by autocrine selection. Peptides MMWLL (Chen, et al. (1995). *J. Biol. Chem.* 270:23398-23401) and fMLP (Showell, et al., (1976) *J. Exp. Med.* 143:1154-1169) were identified previously as agonists of FPR1. f-A5 is an N-terminally formylated derivative of peptide A5.

Specificity of Interaction Between FPRL-1 and the Surrogate Ligands.

As illustrated with peptide A5, several lines of evidence confirmed that the six selected peptides function as agonists for FPRL-1 in yeast. First, growth of the autocrine strain in the absence of histidine is absolutely dependent on the expression of both FPRL-1 and the peptide; loss of the plasmid encoding either the receptor or the peptide resulted in histidine auxotrophy (FIG. 6a). Second, the FPRL-1 receptor and the peptide-expressing plasmid were transformed into strain CY6565, which is analogous to CY6571 except that it contains a FUS1-lacZ fusion gene so that activation of the pheromone pathway induces β-galactosidase synthesis. β-galactosidase levels were significantly higher in transformants carrying both FPRL-1- and peptide-expressing plasmids than in transformants carrying either plasmid alone (FIG. 6b). Finally, exogenous addition of chemically synthesized peptide to strain CY6565, which expressed FPRL-1 and carried the pheromone pathway-responsive FUS1-lacZ gene, resulted in a dose-dependent induction of β-galactosidase activity. The apparent EC$_{50}$ for activation by peptide A5 was approximately $5 \times 10^{-6}$ M. Similar results were obtained with chemically synthesized versions of the other identified peptides, each giving a different EC$_{50}$ value (data not shown). Strain CY6565 was unresponsive to the C5a receptor-specific peptide agonists, N-MeF-K-P-dCha-Cha-dR (SEQ ID NO: 49) and N-MeF-K-P-dCha-F-dR (SEQ ID NO: 49) (Konteatis, et al., (1994) *J. Immunol.* 153:4200-4205) or the FPR1 agonist, fMLP. Conversely, neither C5a receptor-expressing yeast nor FPR1-expressing yeast were activated by the FPRL-1-selected peptide agonists, although each strain exhibited a dose-dependent response to its respective receptor specific peptide agonists (data not shown). This last experiment indicated that the peptides identified by the autocrine procedure are authentic, selective agonists for FPRL-1.

In order to test further the specificity of the responses obtained with the six peptide ligands, human cell lines stably expressing either FPR1 or FPRL-1 were established from an HEK293 clone expressing human Gα$_{16}$. Activity was determined by measuring transient Ca$^{2+}$ flux in cells as a function of peptide concentration. EC$_{50}$ values were calculated from the titration data using GraphPad Prism software. Addition of any of the synthetic peptides to cells expressing FPRL-1 yielded a dose-dependent activation of calcium mobilization with EC$_{50}$ values ranging from $2 \times 10^{-9}$ M to $2.4 \times 10^{-6}$ M (FIG. 7a and Table 1). Differences in EC$_{50}$ values obtained with the receptor expressed in yeast cells versus mammalian cells were noted and may reflect partial exclusion of a peptide by, or nonspecific binding of a peptide to, the yeast cell wall. In contrast to the results obtained with the FPRL-1-(FPR1) expressing cell line, none of the peptides induced calcium mobilization in the parental Gα$^{16}$-expressing cells. In addition, most stimulated calcium mobilization in the cell line expressing FPR1 only at concentrations significantly higher than those required to stimulate FPRL-1 (FIG. 7b and Table 1). Reciprocally, fMLP stimulated transient calcium mobilization in the cell line expressing FPR1 with an EC$_{50}$ value less that $3-0 \times^{-10}$ M but only weakly stimulated cells expressing FPRL-1 (EC$_{50}$ of $4 \times 10^{-7}$ M). Thus, most of the identified peptides are potent and selective agonists of the FPRL-1 receptor.

Analysis of several additional potential ligands provided insight into the structural requirements for FPRL-1 receptor activation. Addition of a formyl group to the N-terminus of peptide A5 increased the agonist activity of the molecule on both FPRL-1 and FPR1 approximately 20-100 fold (EC$_{50}$ values of $2 \times 10^{-9}$ M and $1 \times 10^{-10}$ M, respectively), while maintaining the relative activities on the two receptors (Table 1). Peptide MMWLL, an FPR1 agonist identified from a tethered ligand library expressed in Xenopus oocytes (Chen et al., (1995) *J. Biol. Chem.* 270:23398-23401) was also assayed using these cell lines (data not shown). Peptide MMWLL was active on both receptors but had greater activity on FPR1-expressing cells than on FPRL-1-expressing cells (Table 1). Formylation of MMWLL (SEQ ID NO: 7) also increased its relative activity against both receptors (data not shown). These results indicate that the FPRL-1 receptor, like FPR1, can be activated by formylated peptides but formylation is not required for receptor activation. Finally, lipoxin A4 failed to induce a calcium response in HEK293 cells expressing FPRL-1, even though, as previously reported (Romano, et al. (1996). *J. Immunol.* 157: 2149-2154), lipoxin A4 promotes a detectable increase in adhesion of monocytic THP-I cells to laminin (data not shown). Thus, while lipoxin A4 has been shown to bind selectively and avidly to FPRL-1, its association with the receptor does not stimulate the same cellular response as do the surrogate ligands of the invention, which appear to function as agonists of the receptor. These results bring into question the assumption that lipoxin A4 is the sole natural agonist of FPRL-1-.

Activity of a Surrogate Ligand on Endogenously-expressed Receptor.

Figure 8:
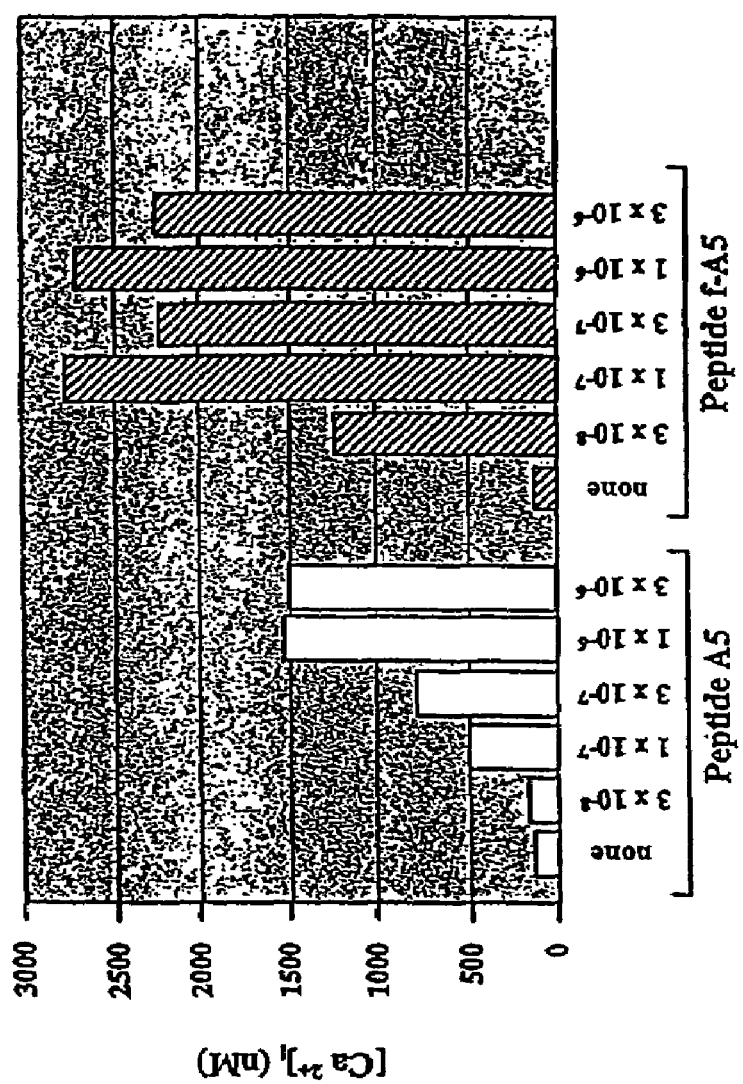
FIG. 8 is a graph depicting intracellular calcium concentration in human neutrophils exposed to synthetic peptide A5 and formylated A5 (f-A5).

The availability of a selective and potent agonist of the FPRL-1 receptor allowed evaluation of the physiological role of the receptor. Since the FPRL-1 receptor gene is transcribed in human neutrophils (Durstin, et al. (1994) *Biochem. Biophys. Res. Comm.* 201:174-179), peptide A5 was used to assess whether functional receptor was present on these cells and, if so, to determine the physiological response of human neutrophils to activation of FPRL-1. The calcium mobilization in indo-1 loaded human neutrophils was measured following addition of various concentrations of non-formylated or formylated peptide A5 (FIG. 8). Stimulation with peptide A5 resulted in a dose-dependent increase in calcium mobilization with an EC$_{50}$ of approximately $3 \times 10^{-7}$ M. Formylated A5 was more potent than A5 in mobilizing calcium with a 10-fold lower EC$_{50}$ value, consistent with the results observed with HEK293 cells. Peptide fMLP gave a similar induction of calcium mobilization in neutrophils with an EC$_{50}$ value of $<2 \times 10^{-10}$ M (data not shown). The difference in absolute EC$_{50}$ values in the response of neutrophils versus HEK cells to A5 and fA5 may reflect differences in receptor numbers and/or coupling in the two cell types. The specificity of peptide A5 for FPRL-1 suggests that functional receptor is present on neutrophils and that its activation yields a similar physiological response as does activation of FPR1. Thus, FPRL-1 agonists may induce a chemotactic response and subsequent degranulation of neutrophils and this receptor may play a significant role in leukocyte infiltration and activation.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A recombinant cell which comprises:

a heterologous formyl peptide receptor like-1 (FPRL-1) receptor expressed in the cell membrane of said cell such that signal transduction activity via said receptor is modulated by interaction of an extracellular region of the receptor with an extracellular signal; and a polypeptide, or analog thereof, that is a ligand agonist of said FPRL-1 receptor, wherein said ligand agonist is transported to a location allowing interaction with the extracellular region of said FPRL-1 receptor expressed in the cell membrane, and is expressed at a level sufficient for said ligand agonist to bind to and activate said FPRL-1 receptor, thereby causing a detectable signal to be generated.

2. The cell of claim 1, wherein said heterologous FPRL-1 receptor is coupled to a signal transduction pathway.

3. The cell of claim 1, wherein said heterologous FPRL-1 receptor acts as a surrogate for an endogenous cell receptor in a signal transduction pathway of the cell and wherein binding of said ligand agonist to said receptor activates the signal transduction activity of said receptor thereby generating a detectable signal.

4. The cell of claim 3 further comprising a reporter construct that is activated by the signal transduction pathway, wherein the detectable signal provided by said ligand agonist is mediated by the reporter construct.

5. The cell of claim 4, wherein said detectable signal is selected from the group consisting of a growth signal, intracellular calcium mobilization, an optical signal, second messenger production, changes in GTP hydrolysis, and phospholipid hydrolysis.

6. The cell of claim 1, wherein said ligand agonist has an $EC_{50}$ of $2 \times 10^{-5}$ M or less and comprises a polypeptide comprising from 3 to 80 amino acid residues.

7. The cell of claim 6, wherein said polypeptide comprises from 3 to 40 amino acid residues.

8. The cell of claim 7, wherein said ligand agonist comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, and analogs thereof.

9. The cell of claim 1, wherein said FPRL-1 receptor is associated with an indicator molecule which provides a detectable signal upon binding of said ligand agonist to said receptor.

10. The cell of claim 9, wherein said indicator molecule comprises GFP or a β-arrestin-GFP conjugate.

11. The cell of claim 1 further comprising a heterologous test polypeptide, wherein the heterologous test polypeptide is transported to a location allowing interaction with the extracellular region of said FPRL-1 receptor expressed in the cell membrane; and wherein the heterologous test polypeptide is expressed at a sufficient level such that modulation of the signal transduction activity of the receptor by the heterologous test polypeptide alters said detectable signal.

12. The cell of claim 11, wherein said heterologous test polypeptide includes a signal sequence that facilitates transport of the polypeptide to a location allowing interaction with the extracellular region of the receptor.

13. The cell of claim 1, wherein said heterologous FPRL-1 is human FPRL-1.

14. The cell of claims 1 or 3, wherein said cell is a eukaryotic cell.

15. The cell of claim 14, wherein said eukaryotic cell is a yeast cell, and wherein said heterologous FPRL-1 receptor acts as a surrogate for an endogenous yeast pheromone receptor in a pheromone response pathway of said yeast cell.

16. The cell of claim 15, which belongs to the species *Saccharomyces cerevisiae*.

17. A recombinant yeast cell which comprises:
a heterologous formyl peptide receptor like-1 (FPRL-1) receptor expressed in the cell membrane of said yeast cell such that signal transduction activity via said receptor is modulated by interaction of an extracellular region of the receptor with an extracellular signal; and
a polypeptide, or analog thereof, that is a ligand agonist of said FPRL-1 receptor, wherein said ligand agonist is transported to a location allowing interaction with the extracellular region of said FPRL-1 receptor expressed in the cell membrane, and is expressed at a level sufficient for said ligand agonist to bind to and activate said FPRL-1 receptor, thereby causing a detectable signal to be generated.

18. The yeast cell of claim 17, wherein said heterologous FPRL-1 receptor is coupled to a signal transduction pathway.

19. The yeast cell of claim 17, wherein said heterologous FPRL-1 receptor acts as a surrogate for an endogenous yeast pheromone receptor in a pheromone response pathway of the cell and wherein binding of said ligand agonist to said receptor activates the signal transduction activity of said receptor thereby generating a detectable signal.

20. The yeast cell of claim 19 further comprising a reporter construct that is activated by the signal transduction pathway, wherein the detectable signal provided by said ligand agonist is mediated by the reporter construct.

21. The yeast cell of claim 20, wherein said reporter construct comprises a pheromone-responsive promoter operably linked to a selectable gene.

22. The yeast cell of claim 21, wherein said pheromone-responsive promoter is the FUS1 promoter.

23. The yeast cell of claim 21, wherein said selectable gene is selected from the group consisting of URA3, LYS2, HIS3, LEU2, TRP1, ADE1, ADE2, ADE3, ADE4, ADE5, ADE7, ADE8, ARG1, ARG3, ARG4, ARG5, ARG6, ARG8, HIS1, HIS4, HIS5 ILV1, ILV2, ILV5, THR1, THR4, TRP2, TRP3, TRP4, TRP5, LACZ, LEU1, LEU4, MET2, MET3, MET4, MET8, MET9, MET14, MET16, MET19, URA1, URA2, URA4, URA5, URA10, H0M3, H0M6, ASP3, CHO1, ARO2, ARO7, CYS3, OLE1, IN01, IN02, IN04, PRO1, and PRO3.

24. The yeast cell of claim 19 further comprising a heterologous test polypeptide, wherein the heterologous test polypeptide is transported to a location allowing interaction with the extracellular region of said FPRL-1 receptor expressed in the cell membrane; and wherein the heterologous test polypeptide is expressed at a sufficient level such that modulation of the signal transduction activity of the receptor by the heterologous test polypeptide alters said detectable signal.

25. The yeast cell of claim 24, wherein said heterologous test polypeptide includes a signal sequence that facilitates transport of the polypeptide to a location allowing interaction with the extracellular region of the receptor.

26. The yeast cell of claim 24, wherein said signal sequence corresponds to a leader peptide of the *Saccharomyces cerevisiae* α factor or a-factor.

27. The yeast cell of claim 19, which belongs to the species *Saccharomyces cerevisiae*, and wherein said yeast cell further comprises a mutation in at least one gene selected from the group consisting of STP22, VPS1, KRE1, CAV1, STE50, SGV1, PIK1, AFR1, FAR1, SST2, BAR1, STE2, STE3, STE14, MFa1, and MFa2.

28. The yeast cell of claim 19, which is a mutant strain of a yeast cell having a pheromone system pathway that is desensitized at slower rate than a wild type strain under the same conditions of continuous stimulation of the pheromone system pathway.

29. The yeast cell of claim 19, which belongs to the species *Saccharomyces cerevisiae*, and wherein said yeast cell has a ste14 mutation.

30. The yeast cell of claim 19, which belongs to the species *Saccharomyces cerevisiae*, and wherein said yeast cell has a ste2 or ste3 mutation.

31. The yeast cell of claim 19, which belongs to the species *Saccharomyces cerevisiae*.

32. The yeast cell of claim 17, wherein said ligand has an $EC_{50}$ of $2\times10^{-5}M$ or less and comprises a polypeptide comprising from 3 to 80 amino acid residues.

33. The yeast cell of claim 32, wherein said polypeptide comprises from 3 to 40 amino acid residues.

34. The yeast cell of claim 33, wherein said ligand agonist comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, and analogs thereof.

35. The yeast cell of claim 17, wherein said FPRL-1 receptor is associated with an indicator molecule which provides a detectable signal upon binding of said ligand agonist to said receptor.

36. The yeast cell of claim 35, wherein said indicator molecule comprises GFP or a β-arrestin-GFP conjugate.

37. The yeast cell of claim 17, wherein said ligand agonist is associated with an indicator molecule which provides a detectable signal upon binding of said ligand agonist to said receptor.

38. The yeast cell of claim 17, wherein said FPRL-1 receptor is human FPRL-1.

* * * * *

```
                        SEQUENCE LISTING

<160> NUMBER OF SEQ ID NOS: 47

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: synthetic
      construct

<400> SEQUENCE: 1

Ser Leu Leu Trp Leu Thr Cys Arg Pro Trp Glu Ala Met
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: synthetic
      construct

<400> SEQUENCE: 2

Leu Glu Ser Ile Phe Arg Ser Leu Leu Phe Arg Val Met
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: synthetic
      construct

<400> SEQUENCE: 3

Cys Pro Ala Ala Val Leu Trp Arg Trp Val Pro Met
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: synthetic
      construct

<400> SEQUENCE: 4

Ser Met Cys Pro Thr Ala Ser Ala Trp Val Trp Leu Met
 1               5                  10

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: synthetic
      construct
```

```
<400> SEQUENCE: 5

Arg Phe Pro Lys Asn Cys His Leu Arg Pro Pro Arg Met Ile Leu Phe
 1               5                  10                  15

Thr Ala Leu Val
            20

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: synthetic
      construct

<400> SEQUENCE: 6

Pro Pro Phe Phe Phe Arg Pro Val Gly Met Phe
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: synthetic
      construct

<400> SEQUENCE: 7

Met Met Trp Leu Leu
 1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: (1)
<223> OTHER INFORMATION: The Ser residue is modified with a
      formyl group

<400> SEQUENCE: 8

Ser Leu Leu Trp Leu Thr Cys Arg Pro Trp Glu Ala Met
 1               5                  10

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: synthetic
      construct

<400> SEQUENCE: 9
gttaagaacc atatactagt atcaaaaatg tctg                              34

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: synthetic
      construct

<400> SEQUENCE: 10
```
tgatcaaaat ttactagttt gaaaaagtaa tttcg                35

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: synthetic
      construct

<400> SEQUENCE: 11
ggcaaaatac tagtaaaatt ttcatgtc                28

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: synthetic
      construct

<400> SEQUENCE: 12
ggcccttaac acactagtgt cgcattatat ttac                34

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: synthetic
      construct

<400> SEQUENCE: 13
ctaaagaaga agggtatct ttgcttaagc tcgagatctc gactgataac aacagtgtag                60

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: synthetic
      construct

<400> SEQUENCE: 14
catacacaat ataaagcttt aaaagaatga g                31

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: synthetic
      construct

<400> SEQUENCE: 15
ttaagcgtga ggcagaagct tatcgata                28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: synthetic
      construct

<400> SEQUENCE: 16

```
cgcactccgt cttcgaatag ctatctag                                          28
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: synthetic
      construct

<400> SEQUENCE: 17

```
gctacttaag cgtgaggcag aagct                                             25
```

<210> SEQ ID NO 18
<211> LENGTH: 74
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: (11)..(49)
<223> OTHER INFORMATION: n = any nucleotide
<220> FEATURE:
<221> NAME/KEY: misc_feature
<222> LOCATION: (11)..(49)
<223> OTHER INFORMATION: The sequence "nnn" occurs at least once or any
      integer number to a maximum of 13

<400> SEQUENCE: 18

```
cggatgatca nnnnnnnnnn nnnnnnnnnn nnnnnnnnnn nnnnnnnnna gcttctgcct       60
cacgcttaag tagc                                                         74
```

<210> SEQ ID NO 19
<211> LENGTH: 71
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: 19-20,22-23,25-26,28-29,31-32,34-35,37-38,40-41,
      43-44,46-47,49-50,52-53
<223> OTHER INFORMATION: n=any nucleotide

<400> SEQUENCE: 19

```
ctggatgcga agacagctnn knnknnknnk nnknnknnkn nknnknnknn knnktgatca       60
gtctgtgacg c                                                            71
```

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: synthetic
      construct

<400> SEQUENCE: 20

```
gcgtcacaga ctgatca                                                      17
```

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: synthetic construct

<400> SEQUENCE: 21
tgatcagtct gtgacgc                                               17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: synthetic
      construct

<400> SEQUENCE: 22
actagtcaga cactgcg                                               17

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: synthetic
      construct

<400> SEQUENCE: 23
ccaaaataag tacaaagctt tcgaatagaa atgcaaccat c                    41

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: synthetic
      construct

<400> SEQUENCE: 24
gccgctccaa aagaaaagac ctcgagctcg cttaagttct gcgtacaaaa acgttgttc   59

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: synthetic
      construct

<400> SEQUENCE: 25
ggtactcgag tgaaagaag gacaac                                      26

<210> SEQ ID NO 26
<211> LENGTH: 85
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: (21)..(56)
<223> OTHER INFORMATION: n=any nucleotide
<220> FEATURE:
<221> NAME/KEY: misc_feature
<222> LOCATION: (21)..(59)
<223> OTHER INFORMATION: The sequence "nnn" occurs at least once or any
      integer number of times to a maximum of 13

<400> SEQUENCE: 26
cgtacttaag caataacaca nnnnnnnnnn nnnnnnnnnn nnnnnnnnnn nnnnnnnng   60 ttgtccttct tttcactcga gtacc                                    85

<210> SEQ ID NO 27
<211> LENGTH: 77
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: 29-30,32-33,35-36,38-39,41-42,44-45,47-48,50-51,
      53-54,56-57,59-60,62-63,65-66
<223> OTHER INFORMATION: n=any nucleotide
<220> FEATURE:
<221> NAME/KEY: misc_feature
<222> LOCATION: (29)..(67)
<223> OTHER INFORMATION: The sequence "nnk" occurs at least once or any
      integer number to a maximum of 13

<400> SEQUENCE: 27
cgtgaagctt aagcgtgagg cagaagctnn knnknnknnk nnknnknnkn nknnknnknn    60
knnknnktga tcatccg                                                  77

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: synthetic
      construct

<400> SEQUENCE: 28
cgtgaagctt aagcgtgagg cagaagct                                      28

<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: 12-13,15-16,18-19,21-22,24-25,27-28,30-31,33-34,
      36-37,39-40,42-43,45-46,48-49
<223> OTHER INFORMATION: n=any nucleotide
<220> FEATURE:
<221> NAME/KEY: misc_feature
<222> LOCATION: (11)..(49)
<223> OTHER INFORMATION: The sequence "mnn" occurs at least once or any
      integer number to a maximum of 13

<400> SEQUENCE: 29
cggatgatca mnnmnnmnnm nnmnnmnnmn nmnnmnnmnn mnnmnnmnna gcttctg      57

<210> SEQ ID NO 30
<211> LENGTH: 79
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: 27-28,30-31,33-34,36-37,39-40,42-43,45-46,48-49,
      51-52,54-55,57-58
<223> OTHER INFORMATION: n=any nucleotide
<220> FEATURE:
<221> NAME/KEY: misc_feature

```
<222> LOCATION: (27)..(58)
<223> OTHER INFORMATION: The sequence "nnk" occurs at least once or any
      integer number to a maximum of 11

<400> SEQUENCE: 30
ggtactcgag tgaaaagaag gacaacnnkn nknnknnknn knnknnknnk nnknnknnkt      60
gtgttattgc ttaagtacg                                                  79

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: synthetic
      construct

<400> SEQUENCE: 31
ggtactcgag tgaaaagaag gacaac                                          26

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: misc_feature
<222> LOCATION: 22-23,25-26,28-29,31-32,34-35,37-38,40-41,43-44,
      46-47,49-50,52-53
<223> OTHER INFORMATION: n=any nucleotide
<220> FEATURE:
<221> NAME/KEY: misc_feature
<222> LOCATION: (21)..(53)
<223> OTHER INFORMATION: The sequence "mnn" occurs at least once or any
      integer number to a maximum of 11

<400> SEQUENCE: 32
cgtacttaag caataacaca mnnmnnmnnm nnmnnmnnmn nmnnmnnmnn mnngttgtcc      60

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: synthetic
      construct

<400> SEQUENCE: 33
tatgctctgt tgttcatttt ttttgatatt ccg                                  33

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: synthetic
      construct

<400> SEQUENCE: 34

Tyr Ala Leu Phe Val His Phe Phe Asp Ile Pro
 1               5                  10

<210> SEQ ID NO 35
<211> LENGTH: 33
<212> TYPE: DNA
<213> ORGANISM: Artificial Sequence
<220> FEATURE:
```

<223> OTHER INFORMATION: Description of Artificial Sequence: synthetic
      construct

<400> SEQUENCE: 35
tttaagggtc aggtgcgttt tgtggttctt gct                                    33

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: synthetic
      construct

<400> SEQUENCE: 36

Phe Lys Gly Gln Val Arg Phe Val Val Leu Ala
 1               5                  10

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: synthetic
      construct

<400> SEQUENCE: 37
cttatgtctc cgtctttttt tttttttgcct gcg                                   33

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: synthetic
      construct

<400> SEQUENCE: 38

Leu Met Ser Pro Ser Phe Phe Phe Leu Pro Ala
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: synthetic
      construct

<400> SEQUENCE: 39

Tyr Ile Ile Lys Gly Val Phe Trp Asp Pro Ala
 1               5                  10

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: synthetic
      construct

<400> SEQUENCE: 40
ggcgcccggt ctcccatgga aaccaacttc tccact                                 36

<210> SEQ ID NO 41
<211> LENGTH: 40
<212> TYPE: DNA

```
<213> ORGANISM: Artificial Sequence
<220> FEATURE:
<223> OTHER INFORMATION: Description of Artificial Sequence: synthetic
      construct

<400> SEQUENCE: 41
ggcgcccggt ctccgatccc attgcctgta actcagtctc                              40

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: synthetic
      construct

<400> SEQUENCE: 42
tctctgcttt ggctgacttg tcggccttgg gaggcgatg                               39

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: (1)..(5)
<223> OTHER INFORMATION: Xaa=any amino acid

<400> SEQUENCE: 43

Xaa Xaa Xaa Xaa Xaa Thr Cys Arg Pro Trp Glu Ala Met
 1               5                  10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: (6)..(9)
<223> OTHER INFORMATION: Xaa=any amino acid

<400> SEQUENCE: 44

Ser Leu Leu Trp Leu Xaa Xaa Xaa Xaa Trp Glu Ala Met
 1               5                  10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: (10)..(13)
<223> OTHER INFORMATION: Xaa=any amino acid

<400> SEQUENCE: 45

Ser Leu Leu Trp Leu Thr Cys Arg Pro Xaa Xaa Xaa Xaa
 1               5                  10

<210> SEQ ID NO 46
<211> LENGTH: 13
```

```
-continued

<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: 1,3,5,7,9,11,13
<223> OTHER INFORMATION: Xaa=any amino acid

<400> SEQUENCE: 46

Xaa Leu Xaa Trp Xaa Thr Xaa Arg Xaa Trp Xaa Ala Xaa
 1               5                  10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: synthetic
      construct
<220> FEATURE:
<221> NAME/KEY: VARIANT
<222> LOCATION: 2,4,6,8,10,12
<223> OTHER INFORMATION: Xaa=any amino acid

<400> SEQUENCE: 47

Ser Xaa Leu Xaa Leu Xaa Cys Xaa Pro Xaa Glu Xaa Met
 1               5                  10
```